US012264191B2

(12) United States Patent
Winterling et al.

(10) Patent No.: US 12,264,191 B2
(45) Date of Patent: Apr. 1, 2025

(54) DE-IMMUNIZED FACTOR VIII MOLECULE AND PHARMACEUTICAL COMPOSITIONS COMPRISING THE SAME

(71) Applicant: Biotest AG, Dreieich (DE)

(72) Inventors: Karina Winterling, Darmstadt (DE); Steffen Kistner, Frankfurt am Main (DE); Jens Daufenbach, Mainz (DE); Annie de Groot, Providence, RI (US); William Martin, Providence, RI (US); Christopher Ungerer, Langen (DE)

(73) Assignee: Biotest AG, Dreieich (DE)

( * ) Notice: Subject to any disclaimer, the term of this patent is extended or adjusted under 35 U.S.C. 154(b) by 233 days.

(21) Appl. No.: 17/046,601

(22) PCT Filed: Apr. 11, 2019

(86) PCT No.: PCT/EP2019/059233
§ 371 (c)(1),
(2) Date: Oct. 9, 2020

(87) PCT Pub. No.: WO2019/197524
PCT Pub. Date: Oct. 17, 2019

(65) Prior Publication Data

US 2024/0010707 A1 Jan. 11, 2024

(30) Foreign Application Priority Data

Apr. 12, 2018 (EP) .................................... 18166982

(51) Int. Cl.

| | |
|---|---|
| ***C07K 14/755*** | (2006.01) |
| ***A61K 31/573*** | (2006.01) |
| ***A61K 31/675*** | (2006.01) |
| ***A61K 38/37*** | (2006.01) |
| ***A61K 39/395*** | (2006.01) |
| ***C07K 16/28*** | (2006.01) |
| ***G01N 33/50*** | (2006.01) |

(52) U.S. Cl.
CPC .......... *C07K 14/755* (2013.01); *A61K 31/573* (2013.01); *A61K 31/675* (2013.01); *A61K 38/37* (2013.01); *A61K 39/39541* (2013.01); *C07K 16/2887* (2013.01); *G01N 33/5047* (2013.01); *G01N 33/505* (2013.01)

(58) Field of Classification Search
CPC .............. C07K 14/755; C07K 16/2887; A61K 31/573; A61K 31/675; A61K 38/37; A61K 39/39541; G01N 33/5047; G01N 33/505
See application file for complete search history.

(56) References Cited

U.S. PATENT DOCUMENTS

| | | | | |
|---|---|---|---|---|
| 2003/0166536 A1* | 9/2003 | Lollar | .................... | A61K 38/37 435/69.6 |
| 2012/0065136 A1 | 3/2012 | Fay et al. | | |

FOREIGN PATENT DOCUMENTS

| | | | |
|---|---|---|---|
| EP | 1136553 | A1 | 9/2001 |
| WO | 03087161 | A1 | 10/2003 |

OTHER PUBLICATIONS

C. Kamate et al. (2007). Depletion of CD4+/CD25-high regulatory T cells may enhance or uncover factor VIII-specific T-cell responses in healthy individuals. Journal of Thrombosis and Haemostasis 5: 611-651. (Year: 2007).*
W.H. Brondyk. (2009). Chapter 11: "Selecting an appropriate method for expressing a recombinant protein." Methods in Enzymology, vol. 463: 131-147. (Year: 2009).*
Shetty et al. (2011) "Acquired hemophilia A: Diagnosis, aetiology, clinical spectrum and treatment options." Autoimmunity Reviews 10(6): 311-316. (Year: 2011).*
C.R. Kleiveland. (2015). Peripheral Blood Mononuclear Cells. In: Verhoeckx, K., et al. The Impact of Food Bioactives on Health. Springer, Cham (Year: 2015).*
Herbener, Peter and Kistner, Steffen. U.S. Appl. No. 17/800,453 (Unpublished). Subcutaneous Administration of Factor VIII. (Year: 2022).*
Kistner, Steffen et al. U.S. Appl. No. 17/639,710 (Unpublished). Factor VIII Protein With Increased Half-Life. (Year: 2022).*
International Search Report for PCT/EP2019/059233, mailed Jul. 31, 2019.

(Continued)

*Primary Examiner* — Julie Wu
*Assistant Examiner* — Elizabeth A Shupe
(74) *Attorney, Agent, or Firm* — Thomas | Horstemeyer, LLP

(57) ABSTRACT

The present invention relates to the field of therapeutic proteins, in particular, to recombinant coagulation factors. It provides a recombinant Factor VIII (FVIII) protein comprising specific point mutations at defined positions, which serve to reduce the immunogenicity of said FVIII protein, wherein the Factor VIII protein substantially retains its coagulant activity. It further provides nucleic acids encoding said de-immunized protein, cell lines and methods of recombinant preparation as well as pharmaceutical compositions comprising the recombinant FVIII of the invention, which are advantageous for use in treatment of patients with Hemophilia A, particularly those who have not yet been treated with a FVIII product. Additionally, it can be a safe alternative for previously treated patients and even for patients who have developed an immune-response to FVIII, e.g., for immune-tolerance-induction therapy (ITI/ITT) or rescue ITI. The invention also provides an assay for determining immunogenicity of a protein.

29 Claims, 12 Drawing Sheets

Figure 2:
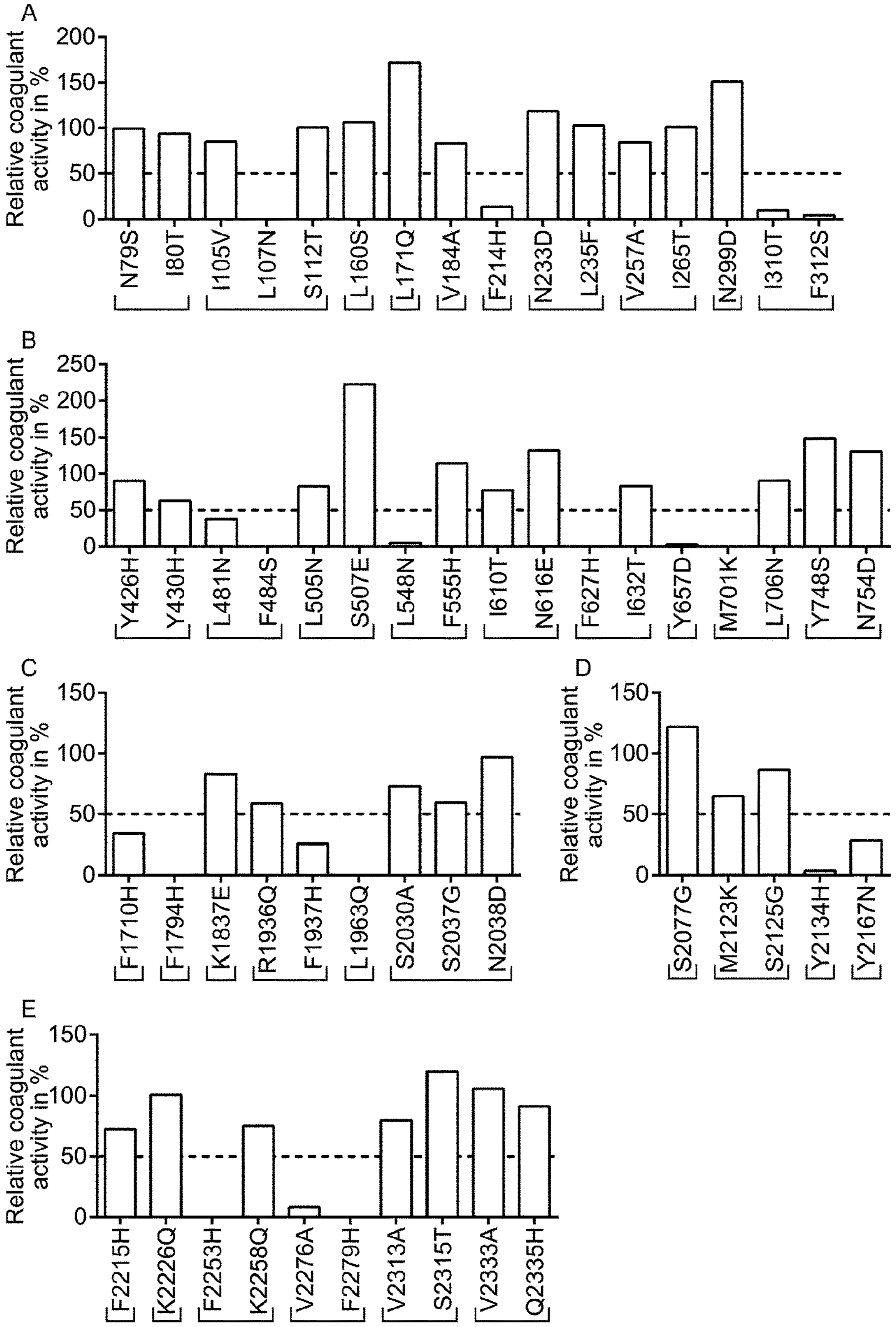

Specification includes a Sequence Listing.

(56) References Cited

OTHER PUBLICATIONS

Jones et al., Identification and removal of a promiscuous CD4+ T cell epitope from the C1 domain of factor VIII, Journal of Thrombosis and Haemostasis, vol. 3, No. 5m p. 1538-7933, 2005.
Parker et al., Optimization of therapeutic proteins to delete T-cell epitopes while maintaining beneficial residue Interactions, retrieved from the Internet: www.ncbi.nlm.nih.gov/pubmed/21523929, abstract; figures 10, 13 Section 3.3.
Ettinger et al., FVIII proteins with a modified immunodominant T-cell epitope exhibit reduced immunogenicity and normal FVIIl activity, Blood Advances, No. 4, p. 309-322, 2018.
Pratt et al., Engineering less immunogenic and antigenic FVIII proteins, Cellular Immunology, vol. 301, p. 12-17, 2015.
European Search Report issued for EP18166982, dated Jun. 28, 2018.
Carcao et al., Recombinant factor VIII Fc fusion protein for immune tolerance induction in patients with severe haemophilia A with inhibitors—A retrospective analysis. Haemophilia 2018:1-8.
EMA/CHMP/699390/2016—Assessment report AFSTYLA.
De Groot et al., Prediction of immunogenicity: in silico paradigms, ex vivo and in vivo correlates. Current Opinion in Pharmacology 8, 620-626, 2008.
De Groot et al., Reducing risk, improving outcomes: Bioengineering less immunogenic protein therapeutics. Clinical Immunology 131, 189-201, 2009.
De Groot et al., Prediction of immunognicity for therapeutic proteins: State of the art. Current Opinion in Drug Discovery & Development 10, 1-9, 2007.
Kamate et al., Depletion of CD4+/CD25high regulatory T cells may enhance or uncover factor VIII-specific T-cell responses in healthy individuals. Journal of Thrombosis and Haemostasis 5, 611-613, 2007.
Kemball-Cook et al., The Factor VIII Structure and Mutation Resource Site: Hamsters Version 4. Nucleic Acids Research 26, 216-219, 1998.
Krishnamoorthy et al., Recombinant factor VIII Fc (rFVIIIFc) fusion protein reduces immunogenicity and induces tolerance in hemophilia A mice, Cell. Immunol. 2016, http://dx.doi.org/10.1016/j.cellimm, 2008.
Moise et al., Effect of HLA DR epitope de-immunization of Factor VIII in vitro and in vivo. Clinical Immunology 142, 320-331, 2012.
Quah et al., Monitoring lymphocyte proliferation in vitro and in vivo with the intracellular fluorescent dye carboxyfluorescein diacetate succinimidyl ester, Nature Protocols, 2007.
Schubert et al., Population-specific design of de-immunized protein biotherapeutics, PLoS Comput Biol 14(3):e1005983, 2018.
Scott, Inhibitors—cellular aspects and novel approaches for tolerance, Haemophilia 20 (01):80-86, 2014.
Smith et al., Identification of Common Molecular Subsequences, J Mol Biol. 147: 195-197, 1981.
Southwood et al., Several Common HLA-DR Types Share Largely Overlapping Peptide Binding Repertoires, J. Immunol., 160;3363-3373, 1998.
Tangri et al., Rationally Engineered Therapeutic Proteins with Reduced Immunogenicity, J Immunol. 174:3187-3196, 2005.
Weber et al., T cell epitope: Friend or Foe? Immunogenicity of biologics in context. Advanced Drug Delivery Reviews 61, 965-976, 2009.
Cousens, Leslie P., et al., "Regulating Immune Responses to Biologics: Validation of Screening, Deimmunization and Tolerization Approaches," poster at 2014 AAPS National Biotechnology Conference, Sheraton San Diego Hotel & Marina, San Diego, California, May 19-21, 2024.

* cited by examiner

Fig. 1A

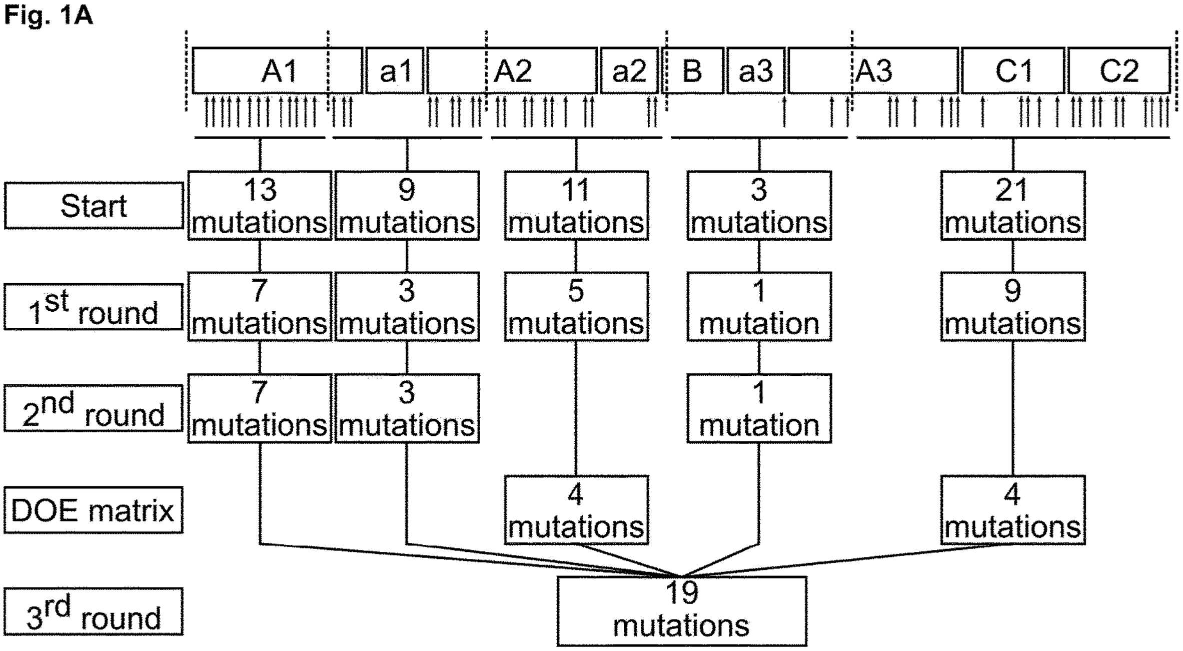

*B*

*MQIELSTCFFLCLLRFCFS*ATRRYYLGAVELSWDYMQSDLGELPVDARFPPRVPKSFPFNTSVVY
KKTLFVEFTDHLF*S*IAKPRPPWMGLLGPTIQAEVYDTVVITLKNMA*T*HPVSLHAVGVSYWKASEG
AEYDDQTSQREKEDDKVFPGGSHTYVWQV*S*KENGPMASDP*Q*CLTYSYLSHVDL*A*KDLNSGLIG
ALLVCREGSLAKEKTQTLHKFILLFAVFDEGKSWHSETK*D*SLMQDRDAASARAWPKMHTVNGYV
NRSLPGL*T*GCHRKSVYWHVIGMGTTPEVHSIFLEGHTFLVR*D*HRQASLEISPITFLTAQTLLMDLG
QFLLFCHISSHQHDGMEAYVKVDSCPEEPQLRMKNNEEAEDYDDDLTDSEMDVVRFDDDNSPSF
IQIRSVAKKHPKTWVHYIAAEEEDWDYAPLVLAPDDRS*H*KSQYLNNGPQRIGRKYKKVRFMAYTD
ETFKTREAIQHESGILGPLLYGEVGDTLLIIFKNQASRPYNIYPHGITDVRPLY*E*RRLPKGVKHLKDF
PILPGEIFKYKWTVTVEDGPTKSDPRCLTRYYSS*H*VNMERDLASGLIGPLLICYKESVDQRGNQIM
SDKRNVILFSVFDENRSWYLTENIQRFLP*E*PAGVQLEDPEFQASNIMHSINGYVFDSLQLSVCLHE
VAYWYILSIGAQTDFLSVFFSGYTFKHKMVYEDTLTLFPFSGETVFMSMENPG*N*WILGCHNSDFR
NRGMTALLKVSSCDKNTGDYYEDSYEDISA*S*LLSKNNAIEPRSFSQDPLAWDNHYGTQIPKEEWK
SQEKSPEKTAFKKKDTILSLNACESNHAIAAINEGQNKPEIEVTWAKQGRTERLCSQNPPVLKRHQ
REITRTTLQSDQEEIDYDDTISVEMKKEDFDIYDEDENQSPRSFQKKTRHYFIAAVERLWDYGMSS
SPHVLRNRAQSGSVPQFKKVVFQEFTDGSFTQPLYRGELNEHLGLLGPYIRAEVEDNIMVTFRNQ
ASRPYSFYSSLISYEEDQRQGAEPRKNFVKPNETKTYFW*E*VQHHMAPTKDEFDCKAWAYFSDVD
LEKDVHSGLIGPLLVCHTNTLNPAHGRQVTVQEFALFFTIFDETKSWYFTENMERNCRAPCNIQME
DPTFKENYRFHAINGYIMDTLPGLVMAQDQRIRWYLLSMGSNENIHSIHFSGHVFTVRKKEEYKMA
LYNLYPGVFETVEMLPSKAGIWRVECLIGEHLHAGMSTLFLVYS*D*KCQTPLGMASGHIRDFQITAS
GQYGQWAPKLARLHYSG*G*INAWSTKEPFSWIKVDLLAPMIIHGIKTQGARQKFSSLYISQFIIMYSL
DGKKWQTYRGNSTGTLMVFFGNVDSSGIKHNIFNPPIIARYIRLHPTHYSIRSTLRMELMGCDLNS
CSMPLGMESKAISDAQITASSYFTNMFATWSPSKARLHLQGRSNAWRPQVNNPKEWLQVDFQKT
MKVTGVTTQGVKSLLTSMYVKEFLISSSQDGHQWTLFFQNGKVKVFQGNQDSFTPVVN*T*LDPPL
LTRYLRIHPQSW*A*HQIALRMEVLGCEAQDLY

Fig. 7A

| Variants | A1 | | | | | | | A1A2 | | | A2 | | | | | BA3 | A3C2 | | | | Coagulant activity chrom. (%) | Coagulant activity clotting (%) | Specific coagulant Activity (%) |
|---|---|---|---|---|---|---|---|---|---|---|---|---|---|---|---|---|---|---|---|---|---|---|---|
| FVIII-19M | N79S | S112 T | L160 S | L171 Q | V184 A | N233 D | I265T | N299 D | Y426 H | S507 E | F555 H | N616 E | L706 N | Y748 S | | K1837 E | N2038 D | S2077 G | S2315 T | V2333 A | 106.2 | 62.5 | 139.4 |
| FVIII-18M | N79S | S112 T | L160 S | L171 Q | V184 A | N233 D | I265T | N299 D | Y426 H | S507 E | F555 H | N616 E | L706 N | Y748 S | | | N2038 D | S2077 G | S2315 T | V2333 A | 156.2 | 108.3 | 139.7 |
| FVIII-15M | N79S | S112 T | L160 S | L171 Q | V184 A | N233 D | I265T | N299 D | Y426 H | S507 E | F555 H | N616 E | L706 N | Y748 S | | K1837 E | | | | | 139.2 | 87.5 | 96.3 |
| FVIII-A1-7M | N79S | S112 T | L160 S | L171 Q | V184 A | N233 D | I265T | | | | | | | | | | | | | | 133.1 | 105.7 | 137.5 |
| FVIII-A1A2-3M | | | | | | | | N299 D | Y426 H | S507 E | | | | | | | | | | | 218.2 | 207.4 | 163.6 |
| FVIII-A2-4M | | | | | | | | | | | F555 H | N616 E | L706 N | Y748 S | | | | | | | 102.7 | 83.2 | 111.6 |
| FVIII-BA3-1M | | | | | | | | | | | | | | | | K1837 E | | | | | 83.0 | x | 78.4 |
| FVIII-A3C2-4M | | | | | | | | | | | | | | | | | N2038 D | S2077 G | S2315 T | V2333 A | 99.5 | 101.6 | 153.3 |
| FVIII-GOF1 | | | | L171 Q | | | | | | S507 E | | | | Y748 S | | | | | | V2333 A | 495.0 | 495.1 | 176.4 |
| FVIII-GOF2 | | | | L171 Q | | | | N299 D | | | | N616 E | | | | | | | | V2333 A | 227.6 | 236.1 | 190.7 |
| FVIII-LS1 | | S112 T | | | | | | | | S507 E | | | | Y748 S | | K1837 E | N2038 D | | | | 199.4 | 165.6 | 119.1 |
| FVIII-LS2 | | S112 T | | | | | | | Y426 H | | | | | | N754 D | K1837 E | N2038 D | | | | 71.8 | 104.9 | 92.1 |

| Vari-ants | A2 | | | | | A3C2 | | | | | Coagulant activity chrom. (%) | Coagulant activity clotting (%) | Specific coagulant Activity (%) |
|---|---|---|---|---|---|---|---|---|---|---|---|---|---|
| V1 | F555H | | I632T | | Y748S | | | | | | 109.4 | 93.6 | 161.5 |
| V2 | F555H | | | L706N | Y748S | | | | | | 113.8 | 90.6 | 123.9 |
| V3 | F555H | N616E | | L706N | | | | | | | 89.0 | 104.4 | 100.9 |
| V4 | F555H | N616E | | | Y748S | | | | | | 143.3 | 118.1 | 148.0 |
| V5 | | N616E | I632T | | Y748S | | | | | | 88.2 | 62.3 | 130.2 |
| V6 | | N616E | | L706N | Y748S | | | | | | 103.9 | 98.6 | 146.7 |
| V7 | | | | | | N2038D | S2077G | | S2315T | | 127.11 | 146.4 | 157.1 |
| V8 | | | | | | | S2077G | K2258Q | S2315T | | 85.37 | 55.8 | 111.1 |
| V9 | | | | | | | S2077G | | S2315T | V2333A | 132.6 | 119.8 | 174.3 |

SEQUENCE LISTING

```
<160> NUMBER OF SEQ ID NOS: 54

<210> SEQ ID NO 1
<211> LENGTH: 2351
<212> TYPE: PRT
<213> ORGANISM: Homo sapiens
<220> FEATURE:
<221> NAME/KEY: SIGNAL
<222> LOCATION: 1..19
<223> OTHER INFORMATION: Signal sequence
<220> FEATURE:
<223> OTHER INFORMATION: FVIII wt full length
```

-continued

<400> SEQUENCE: 1

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415
```

-continued

```
Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830
```

-continued

```
Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser Asn
    1010                1015                1020

Asn Ser Ala Thr Asn Arg Lys Thr His Ile Asp Gly Pro Ser Leu Leu
1025                1030                1035                1040

Ile Glu Asn Ser Pro Ser Val Trp Gln Asn Ile Leu Glu Ser Asp Thr
                1045                1050                1055

Glu Phe Lys Lys Val Thr Pro Leu Ile His Asp Arg Met Leu Met Asp
            1060                1065                1070

Lys Asn Ala Thr Ala Leu Arg Leu Asn His Met Ser Asn Lys Thr Thr
        1075                1080                1085

Ser Ser Lys Asn Met Glu Met Val Gln Gln Lys Lys Glu Gly Pro Ile
    1090                1095                1100

Pro Pro Asp Ala Gln Asn Pro Asp Met Ser Phe Phe Lys Met Leu Phe
1105                1110                1115                1120

Leu Pro Glu Ser Ala Arg Trp Ile Gln Arg Thr His Gly Lys Asn Ser
                1125                1130                1135

Leu Asn Ser Gly Gln Gly Pro Ser Pro Lys Gln Leu Val Ser Leu Gly
            1140                1145                1150

Pro Glu Lys Ser Val Glu Gly Gln Asn Phe Leu Ser Glu Lys Asn Lys
        1155                1160                1165

Val Val Val Gly Lys Gly Glu Phe Thr Lys Asp Val Gly Leu Lys Glu
    1170                1175                1180

Met Val Phe Pro Ser Ser Arg Asn Leu Phe Leu Thr Asn Leu Asp Asn
1185                1190                1195                1200

Leu His Glu Asn Asn Thr His Asn Gln Glu Lys Lys Ile Gln Glu Glu
                1205                1210                1215

Ile Glu Lys Lys Glu Thr Leu Ile Gln Glu Asn Val Val Leu Pro Gln
            1220                1225                1230

Ile His Thr Val Thr Gly Thr Lys Asn Phe Met Lys Asn Leu Phe Leu
        1235                1240                1245

Leu Ser Thr Arg Gln Asn Val Glu Gly Ser Tyr Asp Gly Ala Tyr Ala
```

```
    1250                1255                1260

Pro Val Leu Gln Asp Phe Arg Ser Leu Asn Asp Ser Thr Asn Arg Thr
1265                1270                1275                1280

Lys Lys His Thr Ala His Phe Ser Lys Lys Gly Glu Glu Glu Asn Leu
                1285                1290                1295

Glu Gly Leu Gly Asn Gln Thr Lys Gln Ile Val Glu Lys Tyr Ala Cys
            1300                1305                1310

Thr Thr Arg Ile Ser Pro Asn Thr Ser Gln Gln Asn Phe Val Thr Gln
        1315                1320                1325

Arg Ser Lys Arg Ala Leu Lys Gln Phe Arg Leu Pro Leu Glu Glu Thr
    1330                1335                1340

Glu Leu Glu Lys Arg Ile Ile Val Asp Asp Thr Ser Thr Gln Trp Ser
1345                1350                1355                1360

Lys Asn Met Lys His Leu Thr Pro Ser Thr Leu Thr Gln Ile Asp Tyr
                1365                1370                1375

Asn Glu Lys Glu Lys Gly Ala Ile Thr Gln Ser Pro Leu Ser Asp Cys
            1380                1385                1390

Leu Thr Arg Ser His Ser Ile Pro Gln Ala Asn Arg Ser Pro Leu Pro
        1395                1400                1405

Ile Ala Lys Val Ser Ser Phe Pro Ser Ile Arg Pro Ile Tyr Leu Thr
    1410                1415                1420

Arg Val Leu Phe Gln Asp Asn Ser Ser His Leu Pro Ala Ala Ser Tyr
1425                1430                1435                1440

Arg Lys Lys Asp Ser Gly Val Gln Glu Ser Ser His Phe Leu Gln Gly
                1445                1450                1455

Ala Lys Lys Asn Asn Leu Ser Leu Ala Ile Leu Thr Leu Glu Met Thr
            1460                1465                1470

Gly Asp Gln Arg Glu Val Gly Ser Leu Gly Thr Ser Ala Thr Asn Ser
        1475                1480                1485

Val Thr Tyr Lys Lys Val Glu Asn Thr Val Leu Pro Lys Pro Asp Leu
    1490                1495                1500

Pro Lys Thr Ser Gly Lys Val Glu Leu Leu Pro Lys Val His Ile Tyr
1505                1510                1515                1520

Gln Lys Asp Leu Phe Pro Thr Glu Thr Ser Asn Gly Ser Pro Gly His
                1525                1530                1535

Leu Asp Leu Val Glu Gly Ser Leu Leu Gln Gly Thr Glu Gly Ala Ile
            1540                1545                1550

Lys Trp Asn Glu Ala Asn Arg Pro Gly Lys Val Pro Phe Leu Arg Val
        1555                1560                1565

Ala Thr Glu Ser Ser Ala Lys Thr Pro Ser Lys Leu Leu Asp Pro Leu
    1570                1575                1580

Ala Trp Asp Asn His Tyr Gly Thr Gln Ile Pro Lys Glu Glu Trp Lys
1585                1590                1595                1600

Ser Gln Glu Lys Ser Pro Glu Lys Thr Ala Phe Lys Lys Lys Asp Thr
                1605                1610                1615

Ile Leu Ser Leu Asn Ala Cys Glu Ser Asn His Ala Ile Ala Ala Ile
            1620                1625                1630

Asn Glu Gly Gln Asn Lys Pro Glu Ile Glu Val Thr Trp Ala Lys Gln
        1635                1640                1645

Gly Arg Thr Glu Arg Leu Cys Ser Gln Asn Pro Pro Val Leu Lys Arg
    1650                1655                1660

His Gln Arg Glu Ile Thr Arg Thr Thr Leu Gln Ser Asp Gln Glu Glu
1665                1670                1675                1680
```

```
Ile Asp Tyr Asp Asp Thr Ile Ser Val Glu Met Lys Lys Glu Asp Phe
                1685                1690                1695

Asp Ile Tyr Asp Glu Asp Glu Asn Gln Ser Pro Arg Ser Phe Gln Lys
            1700                1705                1710

Lys Thr Arg His Tyr Phe Ile Ala Ala Val Glu Arg Leu Trp Asp Tyr
        1715                1720                1725

Gly Met Ser Ser Ser Pro His Val Leu Arg Asn Arg Ala Gln Ser Gly
    1730                1735                1740

Ser Val Pro Gln Phe Lys Lys Val Val Phe Gln Glu Phe Thr Asp Gly
1745                1750                1755                1760

Ser Phe Thr Gln Pro Leu Tyr Arg Gly Glu Leu Asn Glu His Leu Gly
                1765                1770                1775

Leu Leu Gly Pro Tyr Ile Arg Ala Glu Val Glu Asp Asn Ile Met Val
            1780                1785                1790

Thr Phe Arg Asn Gln Ala Ser Arg Pro Tyr Ser Phe Tyr Ser Ser Leu
        1795                1800                1805

Ile Ser Tyr Glu Glu Asp Gln Arg Gln Gly Ala Glu Pro Arg Lys Asn
    1810                1815                1820

Phe Val Lys Pro Asn Glu Thr Lys Thr Tyr Phe Trp Lys Val Gln His
1825                1830                1835                1840

His Met Ala Pro Thr Lys Asp Glu Phe Asp Cys Lys Ala Trp Ala Tyr
                1845                1850                1855

Phe Ser Asp Val Asp Leu Glu Lys Asp Val His Ser Gly Leu Ile Gly
            1860                1865                1870

Pro Leu Leu Val Cys His Thr Asn Thr Leu Asn Pro Ala His Gly Arg
        1875                1880                1885

Gln Val Thr Val Gln Glu Phe Ala Leu Phe Phe Thr Ile Phe Asp Glu
    1890                1895                1900

Thr Lys Ser Trp Tyr Phe Thr Glu Asn Met Glu Arg Asn Cys Arg Ala
1905                1910                1915                1920

Pro Cys Asn Ile Gln Met Glu Asp Pro Thr Phe Lys Glu Asn Tyr Arg
                1925                1930                1935

Phe His Ala Ile Asn Gly Tyr Ile Met Asp Thr Leu Pro Gly Leu Val
            1940                1945                1950

Met Ala Gln Asp Gln Arg Ile Arg Trp Tyr Leu Leu Ser Met Gly Ser
        1955                1960                1965

Asn Glu Asn Ile His Ser Ile His Phe Ser Gly His Val Phe Thr Val
    1970                1975                1980

Arg Lys Lys Glu Glu Tyr Lys Met Ala Leu Tyr Asn Leu Tyr Pro Gly
1985                1990                1995                2000

Val Phe Glu Thr Val Glu Met Leu Pro Ser Lys Ala Gly Ile Trp Arg
                2005                2010                2015

Val Glu Cys Leu Ile Gly Glu His Leu His Ala Gly Met Ser Thr Leu
            2020                2025                2030

Phe Leu Val Tyr Ser Asn Lys Cys Gln Thr Pro Leu Gly Met Ala Ser
        2035                2040                2045

Gly His Ile Arg Asp Phe Gln Ile Thr Ala Ser Gly Gln Tyr Gly Gln
    2050                2055                2060

Trp Ala Pro Lys Leu Ala Arg Leu His Tyr Ser Gly Ser Ile Asn Ala
2065                2070                2075                2080

Trp Ser Thr Lys Glu Pro Phe Ser Trp Ile Lys Val Asp Leu Leu Ala
                2085                2090                2095
```

-continued

```
Pro Met Ile Ile His Gly Ile Lys Thr Gln Gly Ala Arg Gln Lys Phe
            2100                2105                2110

Ser Ser Leu Tyr Ile Ser Gln Phe Ile Ile Met Tyr Ser Leu Asp Gly
        2115                2120                2125

Lys Lys Trp Gln Thr Tyr Arg Gly Asn Ser Thr Gly Thr Leu Met Val
    2130                2135                2140

Phe Phe Gly Asn Val Asp Ser Ser Gly Ile Lys His Asn Ile Phe Asn
2145                2150                2155                2160

Pro Pro Ile Ile Ala Arg Tyr Ile Arg Leu His Pro Thr His Tyr Ser
                2165                2170                2175

Ile Arg Ser Thr Leu Arg Met Glu Leu Met Gly Cys Asp Leu Asn Ser
            2180                2185                2190

Cys Ser Met Pro Leu Gly Met Glu Ser Lys Ala Ile Ser Asp Ala Gln
        2195                2200                2205

Ile Thr Ala Ser Ser Tyr Phe Thr Asn Met Phe Ala Thr Trp Ser Pro
    2210                2215                2220

Ser Lys Ala Arg Leu His Leu Gln Gly Arg Ser Asn Ala Trp Arg Pro
2225                2230                2235                2240

Gln Val Asn Asn Pro Lys Glu Trp Leu Gln Val Asp Phe Gln Lys Thr
                2245                2250                2255

Met Lys Val Thr Gly Val Thr Thr Gln Gly Val Lys Ser Leu Leu Thr
            2260                2265                2270

Ser Met Tyr Val Lys Glu Phe Leu Ile Ser Ser Ser Gln Asp Gly His
        2275                2280                2285

Gln Trp Thr Leu Phe Phe Gln Asn Gly Lys Val Lys Val Phe Gln Gly
    2290                2295                2300

Asn Gln Asp Ser Phe Thr Pro Val Val Asn Ser Leu Asp Pro Pro Leu
2305                2310                2315                2320

Leu Thr Arg Tyr Leu Arg Ile His Pro Gln Ser Trp Val His Gln Ile
                2325                2330                2335

Ala Leu Arg Met Glu Val Leu Gly Cys Glu Ala Gln Asp Leu Tyr
            2340                2345                2350


<210> SEQ ID NO 2
<211> LENGTH: 1533
<212> TYPE: PRT
<213> ORGANISM: Artificial Sequence
<220> FEATURE:
<221> NAME/KEY: SIGNAL
<222> LOCATION: 1..19
<223> OTHER INFORMATION: Signal sequence
<220> FEATURE:
<223> OTHER INFORMATION: FVIII-6rs - human FVIII B-domain deleted
<220> FEATURE:
<221> NAME/KEY: DOMAIN
<222> LOCATION: 20..348
<223> OTHER INFORMATION: A1
<220> FEATURE:
<221> NAME/KEY: DOMAIN
<222> LOCATION: 349..398
<223> OTHER INFORMATION: a1
<220> FEATURE:
<221> NAME/KEY: DOMAIN
<222> LOCATION: 399..730
<223> OTHER INFORMATION: A2
<220> FEATURE:
<221> NAME/KEY: DOMAIN
<222> LOCATION: 731..759
<223> OTHER INFORMATION: a2
<220> FEATURE:
<221> NAME/KEY: DOMAIN
<222> LOCATION: 760..849
<223> OTHER INFORMATION: truncated B-domain
```

<220> FEATURE:
<221> NAME/KEY: DOMAIN
<222> LOCATION: 850..894
<223> OTHER INFORMATION: a3
<220> FEATURE:
<221> NAME/KEY: DOMAIN
<222> LOCATION: 895..1221
<223> OTHER INFORMATION: A3
<220> FEATURE:
<221> NAME/KEY: DOMAIN
<222> LOCATION: 1222..1374
<223> OTHER INFORMATION: C1
<220> FEATURE:
<221> NAME/KEY: DOMAIN
<222> LOCATION: 1375..1533
<223> OTHER INFORMATION: C2

<400> SEQUENCE: 2

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320
```

-continued

```
Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
```

-continued

```
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Lys Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165
```

```
Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asn Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Ser Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340

Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420

Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Ser Leu Asp Pro Pro Leu Leu Thr
    1490                1495                1500

Arg Tyr Leu Arg Ile His Pro Gln Ser Trp Val His Gln Ile Ala Leu
1505                1510                1515                1520

Arg Met Glu Val Leu Gly Cys Glu Ala Gln Asp Leu Tyr
                1525                1530
```

<210> SEQ ID NO 3
<211> LENGTH: 1457
<212> TYPE: PRT
<213> ORGANISM: Artificial Sequence
<220> FEATURE:
<223> OTHER INFORMATION: Refacto - human FVIII B-domain deleted

<400> SEQUENCE: 3

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415
```

-continued

```
Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
```

-continued

```
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn Cys
    1010                1015                1020

Arg Ala Pro Cys Asn Ile Gln Met Glu Asp Pro Thr Phe Lys Glu Asn
1025                1030                1035                1040

Tyr Arg Phe His Ala Ile Asn Gly Tyr Ile Met Asp Thr Leu Pro Gly
                1045                1050                1055

Leu Val Met Ala Gln Asp Gln Arg Ile Arg Trp Tyr Leu Leu Ser Met
            1060                1065                1070

Gly Ser Asn Glu Asn Ile His Ser Ile His Phe Ser Gly His Val Phe
        1075                1080                1085

Thr Val Arg Lys Lys Glu Glu Tyr Lys Met Ala Leu Tyr Asn Leu Tyr
    1090                1095                1100

Pro Gly Val Phe Glu Thr Val Glu Met Leu Pro Ser Lys Ala Gly Ile
1105                1110                1115                1120

Trp Arg Val Glu Cys Leu Ile Gly Glu His Leu His Ala Gly Met Ser
                1125                1130                1135

Thr Leu Phe Leu Val Tyr Ser Asn Lys Cys Gln Thr Pro Leu Gly Met
            1140                1145                1150

Ala Ser Gly His Ile Arg Asp Phe Gln Ile Thr Ala Ser Gly Gln Tyr
        1155                1160                1165

Gly Gln Trp Ala Pro Lys Leu Ala Arg Leu His Tyr Ser Gly Ser Ile
    1170                1175                1180

Asn Ala Trp Ser Thr Lys Glu Pro Phe Ser Trp Ile Lys Val Asp Leu
1185                1190                1195                1200

Leu Ala Pro Met Ile Ile His Gly Ile Lys Thr Gln Gly Ala Arg Gln
                1205                1210                1215

Lys Phe Ser Ser Leu Tyr Ile Ser Gln Phe Ile Ile Met Tyr Ser Leu
            1220                1225                1230

Asp Gly Lys Lys Trp Gln Thr Tyr Arg Gly Asn Ser Thr Gly Thr Leu
        1235                1240                1245

Met Val Phe Phe Gly Asn Val Asp Ser Ser Gly Ile Lys His Asn Ile
    1250                1255                1260
```

Phe Asn Pro Pro Ile Ile Ala Arg Tyr Ile Arg Leu His Pro Thr His
1265 1270 1275 1280

Tyr Ser Ile Arg Ser Thr Leu Arg Met Glu Leu Met Gly Cys Asp Leu
1285 1290 1295

Asn Ser Cys Ser Met Pro Leu Gly Met Glu Ser Lys Ala Ile Ser Asp
1300 1305 1310

Ala Gln Ile Thr Ala Ser Ser Tyr Phe Thr Asn Met Phe Ala Thr Trp
1315 1320 1325

Ser Pro Ser Lys Ala Arg Leu His Leu Gln Gly Arg Ser Asn Ala Trp
1330 1335 1340

Arg Pro Gln Val Asn Asn Pro Lys Glu Trp Leu Gln Val Asp Phe Gln
1345 1350 1355 1360

Lys Thr Met Lys Val Thr Gly Val Thr Thr Gln Gly Val Lys Ser Leu
1365 1370 1375

Leu Thr Ser Met Tyr Val Lys Glu Phe Leu Ile Ser Ser Ser Gln Asp
1380 1385 1390

Gly His Gln Trp Thr Leu Phe Phe Gln Asn Gly Lys Val Lys Val Phe
1395 1400 1405

Gln Gly Asn Gln Asp Ser Phe Thr Pro Val Val Asn Ser Leu Asp Pro
1410 1415 1420

Pro Leu Leu Thr Arg Tyr Leu Arg Ile His Pro Gln Ser Trp Val His
1425 1430 1435 1440

Gln Ile Ala Leu Arg Met Glu Val Leu Gly Cys Glu Ala Gln Asp Leu
1445 1450 1455

Tyr

<210> SEQ ID NO 4
<211> LENGTH: 1463
<212> TYPE: PRT
<213> ORGANISM: Artificial Sequence
<220> FEATURE:
<223> OTHER INFORMATION: Afstyla - human FVIII B-domain deleted single chain
<220> FEATURE:
<221> NAME/KEY: SIGNAL
<222> LOCATION: 1..19
<223> OTHER INFORMATION: signal sequence

<400> SEQUENCE: 4

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Ser
100 105 110

His Pro Val Ser Leu His Ala Val Gly Val Ser Tyr Trp Lys Ala Ser
115 120 125

Glu Gly Ala Glu Tyr Asp Asp Gln Thr Ser Gln Arg Glu Lys Glu Asp

-continued

```
            130                 135                 140
Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560
```

-continued

```
Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Thr
    770                 775                 780

Thr Leu Gln Ser Asp Gln Glu Glu Ile Asp Tyr Asp Asp Thr Ile Ser
785                 790                 795                 800

Val Glu Met Lys Lys Glu Asp Phe Asp Ile Tyr Asp Glu Asp Glu Asn
                805                 810                 815

Gln Ser Pro Arg Ser Phe Gln Lys Lys Thr Arg His Tyr Phe Ile Ala
            820                 825                 830

Ala Val Glu Arg Leu Trp Asp Tyr Gly Met Ser Ser Ser Pro His Val
        835                 840                 845

Leu Arg Asn Arg Ala Gln Ser Gly Ser Val Pro Gln Phe Lys Lys Val
    850                 855                 860

Val Phe Gln Glu Phe Thr Asp Gly Ser Phe Thr Gln Pro Leu Tyr Arg
865                 870                 875                 880

Gly Glu Leu Asn Glu His Leu Gly Leu Leu Gly Pro Tyr Ile Arg Ala
                885                 890                 895

Glu Val Glu Asp Asn Ile Met Val Thr Phe Arg Asn Gln Ala Ser Arg
            900                 905                 910

Pro Tyr Ser Phe Tyr Ser Ser Leu Ile Ser Tyr Glu Glu Asp Gln Arg
        915                 920                 925

Gln Gly Ala Glu Pro Arg Lys Asn Phe Val Lys Pro Asn Glu Thr Lys
    930                 935                 940

Thr Tyr Phe Trp Lys Val Gln His His Met Ala Pro Thr Lys Asp Glu
945                 950                 955                 960

Phe Asp Cys Lys Ala Trp Ala Tyr Phe Ser Asp Val Asp Leu Glu Lys
                965                 970                 975
```

-continued

```
Asp Val His Ser Gly Leu Ile Gly Pro Leu Leu Val Cys His Thr Asn
            980                 985                 990

Thr Leu Asn Pro Ala His Gly Arg Gln Val Thr Val Gln Glu Phe Ala
        995                 1000                1005

Leu Phe Phe Thr Ile Phe Asp Glu Thr Lys Ser Trp Tyr Phe Thr Glu
    1010                1015                1020

Asn Met Glu Arg Asn Cys Arg Ala Pro Cys Asn Ile Gln Met Glu Asp
1025                1030                1035                1040

Pro Thr Phe Lys Glu Asn Tyr Arg Phe His Ala Ile Asn Gly Tyr Ile
                1045                1050                1055

Met Asp Thr Leu Pro Gly Leu Val Met Ala Gln Asp Gln Arg Ile Arg
            1060                1065                1070

Trp Tyr Leu Leu Ser Met Gly Ser Asn Glu Asn Ile His Ser Ile His
        1075                1080                1085

Phe Ser Gly His Val Phe Thr Val Arg Lys Lys Glu Glu Tyr Lys Met
    1090                1095                1100

Ala Leu Tyr Asn Leu Tyr Pro Gly Val Phe Glu Thr Val Glu Met Leu
1105                1110                1115                1120

Pro Ser Lys Ala Gly Ile Trp Arg Val Glu Cys Leu Ile Gly Glu His
                1125                1130                1135

Leu His Ala Gly Met Ser Thr Leu Phe Leu Val Tyr Ser Asn Lys Cys
            1140                1145                1150

Gln Thr Pro Leu Gly Met Ala Ser Gly His Ile Arg Asp Phe Gln Ile
        1155                1160                1165

Thr Ala Ser Gly Gln Tyr Gly Gln Trp Ala Pro Lys Leu Ala Arg Leu
    1170                1175                1180

His Tyr Ser Gly Ser Ile Asn Ala Trp Ser Thr Lys Glu Pro Phe Ser
1185                1190                1195                1200

Trp Ile Lys Val Asp Leu Leu Ala Pro Met Ile Ile His Gly Ile Lys
                1205                1210                1215

Thr Gln Gly Ala Arg Gln Lys Phe Ser Ser Leu Tyr Ile Ser Gln Phe
            1220                1225                1230

Ile Ile Met Tyr Ser Leu Asp Gly Lys Lys Trp Gln Thr Tyr Arg Gly
        1235                1240                1245

Asn Ser Thr Gly Thr Leu Met Val Phe Phe Gly Asn Val Asp Ser Ser
    1250                1255                1260

Gly Ile Lys His Asn Ile Phe Asn Pro Pro Ile Ile Ala Arg Tyr Ile
1265                1270                1275                1280

Arg Leu His Pro Thr His Tyr Ser Ile Arg Ser Thr Leu Arg Met Glu
                1285                1290                1295

Leu Met Gly Cys Asp Leu Asn Ser Cys Ser Met Pro Leu Gly Met Glu
            1300                1305                1310

Ser Lys Ala Ile Ser Asp Ala Gln Ile Thr Ala Ser Ser Tyr Phe Thr
        1315                1320                1325

Asn Met Phe Ala Thr Trp Ser Pro Ser Lys Ala Arg Leu His Leu Gln
    1330                1335                1340

Gly Arg Ser Asn Ala Trp Arg Pro Gln Val Asn Asn Pro Lys Glu Trp
1345                1350                1355                1360

Leu Gln Val Asp Phe Gln Lys Thr Met Lys Val Thr Gly Val Thr Thr
                1365                1370                1375

Gln Gly Val Lys Ser Leu Leu Thr Ser Met Tyr Val Lys Glu Phe Leu
            1380                1385                1390

Ile Ser Ser Ser Gln Asp Gly His Gln Trp Thr Leu Phe Phe Gln Asn
```

```
        1395                1400                1405

Gly Lys Val Lys Val Phe Gln Gly Asn Gln Asp Ser Phe Thr Pro Val
    1410                1415                1420

Val Asn Ser Leu Asp Pro Pro Leu Leu Thr Arg Tyr Leu Arg Ile His
1425                1430                1435                1440

Pro Gln Ser Trp Val His Gln Ile Ala Leu Arg Met Glu Val Leu Gly
                1445                1450                1455

Cys Glu Ala Gln Asp Leu Tyr
            1460


<210> SEQ ID NO 5
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-19M
<220> FEATURE:
<221> NAME/KEY: DOMAIN
<222> LOCATION: 20..348
<223> OTHER INFORMATION: A1
<220> FEATURE:
<221> NAME/KEY: MUTAGEN
<222> LOCATION: 79
<223> OTHER INFORMATION: N79S
<220> FEATURE:
<221> NAME/KEY: MUTAGEN
<222> LOCATION: 112
<223> OTHER INFORMATION: S112T
<220> FEATURE:
<221> NAME/KEY: MUTAGEN
<222> LOCATION: 160
<223> OTHER INFORMATION: L160S
<220> FEATURE:
<221> NAME/KEY: MUTAGEN
<222> LOCATION: 171
<223> OTHER INFORMATION: L171Q
<220> FEATURE:
<221> NAME/KEY: MUTAGEN
<222> LOCATION: 184
<223> OTHER INFORMATION: V184A
<220> FEATURE:
<221> NAME/KEY: MUTAGEN
<222> LOCATION: 223
<223> OTHER INFORMATION: N233D
<220> FEATURE:
<221> NAME/KEY: MUTAGEN
<222> LOCATION: 265
<223> OTHER INFORMATION: I265T
<220> FEATURE:
<221> NAME/KEY: MUTAGEN
<222> LOCATION: 299
<223> OTHER INFORMATION: N299D
<220> FEATURE:
<221> NAME/KEY: DOMAIN
<222> LOCATION: 349..398
<223> OTHER INFORMATION: a1
<220> FEATURE:
<221> NAME/KEY: DOMAIN
<222> LOCATION: 399..730
<223> OTHER INFORMATION: A2
<220> FEATURE:
<221> NAME/KEY: MUTAGEN
<222> LOCATION: 426
<223> OTHER INFORMATION: Y426H
<220> FEATURE:
<221> NAME/KEY: MUTAGEN
<222> LOCATION: 507
<223> OTHER INFORMATION: S507E
<220> FEATURE:
<221> NAME/KEY: MUTAGEN
<222> LOCATION: 555
```

<223> OTHER INFORMATION: F555H
<220> FEATURE:
<221> NAME/KEY: MUTAGEN
<222> LOCATION: 616
<223> OTHER INFORMATION: N616E
<220> FEATURE:
<221> NAME/KEY: MUTAGEN
<222> LOCATION: 706
<223> OTHER INFORMATION: L706N
<220> FEATURE:
<221> NAME/KEY: DOMAIN
<222> LOCATION: 731..759
<223> OTHER INFORMATION: a2
<220> FEATURE:
<221> NAME/KEY: MUTAGEN
<222> LOCATION: 748
<223> OTHER INFORMATION: Y748S
<220> FEATURE:
<221> NAME/KEY: DOMAIN
<222> LOCATION: 760..849
<223> OTHER INFORMATION: truncated B-domain
<220> FEATURE:
<221> NAME/KEY: DOMAIN
<222> LOCATION: 850..894
<223> OTHER INFORMATION: a3
<220> FEATURE:
<221> NAME/KEY: DOMAIN
<222> LOCATION: 895..1221
<223> OTHER INFORMATION: A3
<220> FEATURE:
<221> NAME/KEY: MUTAGEN
<222> LOCATION: 1019
<223> OTHER INFORMATION: K1837E
<220> FEATURE:
<221> NAME/KEY: MUTAGEN
<222> LOCATION: 1220
<223> OTHER INFORMATION: N2038D
<220> FEATURE:
<221> NAME/KEY: DOMAIN
<222> LOCATION: 1222..1374
<223> OTHER INFORMATION: C1
<220> FEATURE:
<221> NAME/KEY: MUTAGEN
<222> LOCATION: 1259
<223> OTHER INFORMATION: S2077G
<220> FEATURE:
<221> NAME/KEY: DOMAIN
<222> LOCATION: 1375..1533
<223> OTHER INFORMATION: C2
<220> FEATURE:
<221> NAME/KEY: MUTAGEN
<222> LOCATION: 1497
<223> OTHER INFORMATION: S2315T
<220> FEATURE:
<221> NAME/KEY: MUTAGEN
<222> LOCATION: 1515
<223> OTHER INFORMATION: V2333A

<400> SEQUENCE: 5

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Ser Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Thr
```

-continued

```
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Ser
145                 150                 155                 160

Lys Glu Asn Gly Pro Met Ala Ser Asp Pro Gln Cys Leu Thr Tyr Ser
                165                 170                 175

Tyr Leu Ser His Val Asp Leu Ala Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asp Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Thr Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asp His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser His Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Glu Arg Arg Leu Pro Lys
            500                 505                 510

Gly Val Lys His Leu Lys Asp Phe Pro Ile Leu Pro Gly Glu Ile Phe
        515                 520                 525
```

-continued

```
Lys Tyr Lys Trp Thr Val Thr Val Glu Asp Gly Pro Thr Lys Ser Asp
    530                 535                 540

Pro Arg Cys Leu Thr Arg Tyr Tyr Ser Ser His Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Glu Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Asn Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Ser Leu Leu Ser Lys
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940
```

-continued

```
Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Glu Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165

Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asp Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Gly Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340

Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
```

```
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420

Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Thr Leu Asp Pro Pro Leu Leu Thr
    1490                1495                1500

Arg Tyr Leu Arg Ile His Pro Gln Ser Trp Ala His Gln Ile Ala Leu
1505                1510                1515                1520

Arg Met Glu Val Leu Gly Cys Glu Ala Gln Asp Leu Tyr
                1525                1530


<210> SEQ ID NO 6
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-18M

<400> SEQUENCE: 6

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Ser Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Thr
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Ser
145                 150                 155                 160

Lys Glu Asn Gly Pro Met Ala Ser Asp Pro Gln Cys Leu Thr Tyr Ser
                165                 170                 175

Tyr Leu Ser His Val Asp Leu Ala Lys Asp Leu Asn Ser Gly Leu Ile
```

-continued

```
        180                 185                 190

Gly Ala Leu Leu Val Cys Arg Glu Gly Ser Leu Ala Lys Glu Lys Thr
    195                 200                 205

Gln Thr Leu His Lys Phe Ile Leu Leu Phe Ala Val Phe Asp Glu Gly
    210                 215                 220

Lys Ser Trp His Ser Glu Thr Lys Asp Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Thr Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asp His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser His Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Glu Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser His Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605
```

-continued

```
Asn Ile Gln Arg Phe Leu Pro Glu Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Asn Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Ser Leu Leu Ser Lys
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Lys Val Gln His His Met
    1010                1015                1020
```

-continued

Ala Pro Thr Lys Asp Glu Phe Asp Cys Lys Ala Trp Ala Tyr Phe Ser
1025 1030 1035 1040

Asp Val Asp Leu Glu Lys Asp Val His Ser Gly Leu Ile Gly Pro Leu
1045 1050 1055

Leu Val Cys His Thr Asn Thr Leu Asn Pro Ala His Gly Arg Gln Val
1060 1065 1070

Thr Val Gln Glu Phe Ala Leu Phe Phe Thr Ile Phe Asp Glu Thr Lys
1075 1080 1085

Ser Trp Tyr Phe Thr Glu Asn Met Glu Arg Asn Cys Arg Ala Pro Cys
1090 1095 1100

Asn Ile Gln Met Glu Asp Pro Thr Phe Lys Glu Asn Tyr Arg Phe His
1105 1110 1115 1120

Ala Ile Asn Gly Tyr Ile Met Asp Thr Leu Pro Gly Leu Val Met Ala
1125 1130 1135

Gln Asp Gln Arg Ile Arg Trp Tyr Leu Leu Ser Met Gly Ser Asn Glu
1140 1145 1150

Asn Ile His Ser Ile His Phe Ser Gly His Val Phe Thr Val Arg Lys
1155 1160 1165

Lys Glu Glu Tyr Lys Met Ala Leu Tyr Asn Leu Tyr Pro Gly Val Phe
1170 1175 1180

Glu Thr Val Glu Met Leu Pro Ser Lys Ala Gly Ile Trp Arg Val Glu
1185 1190 1195 1200

Cys Leu Ile Gly Glu His Leu His Ala Gly Met Ser Thr Leu Phe Leu
1205 1210 1215

Val Tyr Ser Asp Lys Cys Gln Thr Pro Leu Gly Met Ala Ser Gly His
1220 1225 1230

Ile Arg Asp Phe Gln Ile Thr Ala Ser Gly Gln Tyr Gly Gln Trp Ala
1235 1240 1245

Pro Lys Leu Ala Arg Leu His Tyr Ser Gly Gly Ile Asn Ala Trp Ser
1250 1255 1260

Thr Lys Glu Pro Phe Ser Trp Ile Lys Val Asp Leu Leu Ala Pro Met
1265 1270 1275 1280

Ile Ile His Gly Ile Lys Thr Gln Gly Ala Arg Gln Lys Phe Ser Ser
1285 1290 1295

Leu Tyr Ile Ser Gln Phe Ile Ile Met Tyr Ser Leu Asp Gly Lys Lys
1300 1305 1310

Trp Gln Thr Tyr Arg Gly Asn Ser Thr Gly Thr Leu Met Val Phe Phe
1315 1320 1325

Gly Asn Val Asp Ser Ser Gly Ile Lys His Asn Ile Phe Asn Pro Pro
1330 1335 1340

Ile Ile Ala Arg Tyr Ile Arg Leu His Pro Thr His Tyr Ser Ile Arg
1345 1350 1355 1360

Ser Thr Leu Arg Met Glu Leu Met Gly Cys Asp Leu Asn Ser Cys Ser
1365 1370 1375

Met Pro Leu Gly Met Glu Ser Lys Ala Ile Ser Asp Ala Gln Ile Thr
1380 1385 1390

Ala Ser Ser Tyr Phe Thr Asn Met Phe Ala Thr Trp Ser Pro Ser Lys
1395 1400 1405

Ala Arg Leu His Leu Gln Gly Arg Ser Asn Ala Trp Arg Pro Gln Val
1410 1415 1420

Asn Asn Pro Lys Glu Trp Leu Gln Val Asp Phe Gln Lys Thr Met Lys
1425 1430 1435 1440

Val Thr Gly Val Thr Thr Gln Gly Val Lys Ser Leu Leu Thr Ser Met

```
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Thr Leu Asp Pro Pro Leu Leu Thr
    1490                1495                1500

Arg Tyr Leu Arg Ile His Pro Gln Ser Trp Ala His Gln Ile Ala Leu
1505                1510                1515                1520

Arg Met Glu Val Leu Gly Cys Glu Ala Gln Asp Leu Tyr
                1525                1530


<210> SEQ ID NO 7
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-15M

<400> SEQUENCE: 7

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Ser Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Thr
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Ser
145                 150                 155                 160

Lys Glu Asn Gly Pro Met Ala Ser Asp Pro Gln Cys Leu Thr Tyr Ser
                165                 170                 175

Tyr Leu Ser His Val Asp Leu Ala Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asp Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Thr Gly Cys His Arg Lys Ser Val
```

```
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asp His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser His Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Glu Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser His Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Glu Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685
```

```
Leu Phe Pro Phe Ser Gly Glu Thr Val Phe Met Ser Met Glu Asn Pro
    690                 695                 700

Gly Asn Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Ser Leu Leu Ser Lys
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Glu Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100
```

```
Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165

Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asn Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Ser Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340

Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420

Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Ser Leu Asp Pro Pro Leu Leu Thr
    1490                1495                1500

Arg Tyr Leu Arg Ile His Pro Gln Ser Trp Val His Gln Ile Ala Leu
1505                1510                1515                1520

Arg Met Glu Val Leu Gly Cys Glu Ala Gln Asp Leu Tyr
```

1525 1530

<210> SEQ ID NO 8
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-A1-7M

<400> SEQUENCE: 8

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Ser Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Thr
100 105 110

His Pro Val Ser Leu His Ala Val Gly Val Ser Tyr Trp Lys Ala Ser
115 120 125

Glu Gly Ala Glu Tyr Asp Asp Gln Thr Ser Gln Arg Glu Lys Glu Asp
130 135 140

Asp Lys Val Phe Pro Gly Gly Ser His Thr Tyr Val Trp Gln Val Ser
145 150 155 160

Lys Glu Asn Gly Pro Met Ala Ser Asp Pro Gln Cys Leu Thr Tyr Ser
165 170 175

Tyr Leu Ser His Val Asp Leu Ala Lys Asp Leu Asn Ser Gly Leu Ile
180 185 190

Gly Ala Leu Leu Val Cys Arg Glu Gly Ser Leu Ala Lys Glu Lys Thr
195 200 205

Gln Thr Leu His Lys Phe Ile Leu Leu Phe Ala Val Phe Asp Glu Gly
210 215 220

Lys Ser Trp His Ser Glu Thr Lys Asp Ser Leu Met Gln Asp Arg Asp
225 230 235 240

Ala Ala Ser Ala Arg Ala Trp Pro Lys Met His Thr Val Asn Gly Tyr
245 250 255

Val Asn Arg Ser Leu Pro Gly Leu Thr Gly Cys His Arg Lys Ser Val
260 265 270

Tyr Trp His Val Ile Gly Met Gly Thr Thr Pro Glu Val His Ser Ile
275 280 285

Phe Leu Glu Gly His Thr Phe Leu Val Arg Asn His Arg Gln Ala Ser
290 295 300

Leu Glu Ile Ser Pro Ile Thr Phe Leu Thr Ala Gln Thr Leu Leu Met
305 310 315 320

Asp Leu Gly Gln Phe Leu Leu Phe Cys His Ile Ser Ser His Gln His
325 330 335

Asp Gly Met Glu Ala Tyr Val Lys Val Asp Ser Cys Pro Glu Glu Pro

-continued

```
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asp Pro Leu Ala Trp
        755                 760                 765
```

-continued

```
Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Lys Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165

Lys Glu Glu Tyr Lys Met Ala Leu Tyr Asn Leu Tyr Pro Gly Val Phe
    1170                1175                1180
```

```
Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asn Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Ser Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340

Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420

Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Ser Leu Asp Pro Pro Leu Leu Thr
    1490                1495                1500

Arg Tyr Leu Arg Ile His Pro Gln Ser Trp Val His Gln Ile Ala Leu
1505                1510                1515                1520

Arg Met Glu Val Leu Gly Cys Glu Ala Gln Asp Leu Tyr
                1525                1530
```

<210> SEQ ID NO 9
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-A2-4M

<400> SEQUENCE: 9

-continued

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
```

```
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser His Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Glu Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Asn Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Ser Leu Leu Ser Lys
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845
```

```
Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Lys Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165

Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asn Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Ser Ile Asn Ala Trp Ser
    1250                1255                1260
```

Thr Lys Glu Pro Phe Ser Trp Ile Lys Val Asp Leu Leu Ala Pro Met
1265 1270 1275 1280

Ile Ile His Gly Ile Lys Thr Gln Gly Ala Arg Gln Lys Phe Ser Ser
1285 1290 1295

Leu Tyr Ile Ser Gln Phe Ile Ile Met Tyr Ser Leu Asp Gly Lys Lys
1300 1305 1310

Trp Gln Thr Tyr Arg Gly Asn Ser Thr Gly Thr Leu Met Val Phe Phe
1315 1320 1325

Gly Asn Val Asp Ser Ser Gly Ile Lys His Asn Ile Phe Asn Pro Pro
1330 1335 1340

Ile Ile Ala Arg Tyr Ile Arg Leu His Pro Thr His Tyr Ser Ile Arg
1345 1350 1355 1360

Ser Thr Leu Arg Met Glu Leu Met Gly Cys Asp Leu Asn Ser Cys Ser
1365 1370 1375

Met Pro Leu Gly Met Glu Ser Lys Ala Ile Ser Asp Ala Gln Ile Thr
1380 1385 1390

Ala Ser Ser Tyr Phe Thr Asn Met Phe Ala Thr Trp Ser Pro Ser Lys
1395 1400 1405

Ala Arg Leu His Leu Gln Gly Arg Ser Asn Ala Trp Arg Pro Gln Val
1410 1415 1420

Asn Asn Pro Lys Glu Trp Leu Gln Val Asp Phe Gln Lys Thr Met Lys
1425 1430 1435 1440

Val Thr Gly Val Thr Thr Gln Gly Val Lys Ser Leu Leu Thr Ser Met
1445 1450 1455

Tyr Val Lys Glu Phe Leu Ile Ser Ser Ser Gln Asp Gly His Gln Trp
1460 1465 1470

Thr Leu Phe Phe Gln Asn Gly Lys Val Lys Val Phe Gln Gly Asn Gln
1475 1480 1485

Asp Ser Phe Thr Pro Val Val Asn Ser Leu Asp Pro Pro Leu Leu Thr
1490 1495 1500

Arg Tyr Leu Arg Ile His Pro Gln Ser Trp Val His Gln Ile Ala Leu
1505 1510 1515 1520

Arg Met Glu Val Leu Gly Cys Glu Ala Gln Asp Leu Tyr
1525 1530

<210> SEQ ID NO 10
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-BA3-1M

<400> SEQUENCE: 10

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

-continued

```
Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
```

-continued

```
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925
```

-continued

```
Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Glu Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165

Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asn Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Ser Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340
```

```
Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420

Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Ser Leu Asp Pro Pro Leu Leu Thr
    1490                1495                1500

Arg Tyr Leu Arg Ile His Pro Gln Ser Trp Val His Gln Ile Ala Leu
1505                1510                1515                1520

Arg Met Glu Val Leu Gly Cys Glu Ala Gln Asp Leu Tyr
                1525                1530


<210> SEQ ID NO 11
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-A3C2-4M

<400> SEQUENCE: 11

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160
```

-continued

```
Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
```

-continued

```
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005
```

```
Lys Pro Asn Glu Thr Lys Thr Tyr Phe Trp Lys Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165

Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asp Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Gly Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340

Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420
```

```
Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Thr Leu Asp Pro Pro Leu Leu Thr
    1490                1495                1500

Arg Tyr Leu Arg Ile His Pro Gln Ser Trp Ala His Gln Ile Ala Leu
1505                1510                1515                1520

Arg Met Glu Val Leu Gly Cys Glu Ala Gln Asp Leu Tyr
                1525                1530


<210> SEQ ID NO 12
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-GOF1

<400> SEQUENCE: 12

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Gln Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240
```

-continued

```
Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Glu Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
```

```
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Ser Leu Leu Ser Lys
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Lys Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085
```

```
Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165

Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asn Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Ser Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340

Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420

Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Ser Leu Asp Pro Pro Leu Leu Thr
    1490                1495                1500
```

```
Arg Tyr Leu Arg Ile His Pro Gln Ser Trp Ala His Gln Ile Ala Leu
1505                1510                1515                1520

Arg Met Glu Val Leu Gly Cys Glu Ala Gln Asp Leu Tyr
                1525                1530


<210> SEQ ID NO 13
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-GOF2

<400> SEQUENCE: 13

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Gln Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asp His Arg Gln Ala Ser
    290                 295                 300

Leu Glu Ile Ser Pro Ile Thr Phe Leu Thr Ala Gln Thr Leu Leu Met
305                 310                 315                 320
```

```
Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Glu Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
```

```
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Lys Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165
```

```
Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asn Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Ser Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340

Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420

Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Ser Leu Asp Pro Pro Leu Leu Thr
    1490                1495                1500

Arg Tyr Leu Arg Ile His Pro Gln Ser Trp Ala His Gln Ile Ala Leu
1505                1510                1515                1520

Arg Met Glu Val Leu Gly Cys Glu Ala Gln Asp Leu Tyr
                1525                1530
```

<210> SEQ ID NO 14
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:

<223> OTHER INFORMATION: FVIII-LS1

<400> SEQUENCE: 14

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Thr
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400
```

-continued

```
Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Glu Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Ser Leu Leu Ser Lys
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
```

-continued

```
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Glu Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165

Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asp Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245
```

```
Pro Lys Leu Ala Arg Leu His Tyr Ser Gly Ser Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340

Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420

Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Ser Leu Asp Pro Pro Leu Leu Thr
    1490                1495                1500

Arg Tyr Leu Arg Ile His Pro Gln Ser Trp Val His Gln Ile Ala Leu
1505                1510                1515                1520

Arg Met Glu Val Leu Gly Cys Glu Ala Gln Asp Leu Tyr
                1525                1530


<210> SEQ ID NO 15
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-LS2
<220> FEATURE:
<221> NAME/KEY: MUTAGEN
<222> LOCATION: 112
<223> OTHER INFORMATION: S112T
<220> FEATURE:
<221> NAME/KEY: MUTAGEN
<222> LOCATION: 426
<223> OTHER INFORMATION: Y426H
<220> FEATURE:
<221> NAME/KEY: MUTAGEN
<222> LOCATION: 754
<223> OTHER INFORMATION: N754D
<220> FEATURE:
<221> NAME/KEY: MUTAGEN
```

```
<222> LOCATION: 1019
<223> OTHER INFORMATION: K1837E
<220> FEATURE:
<221> NAME/KEY: MUTAGEN
<222> LOCATION: 1220
<223> OTHER INFORMATION: N2038D

<400> SEQUENCE: 15

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Thr
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
```

```
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser His Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asp Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800
```

```
Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Glu Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
            1140                1145                1150

Asn Ile His Ser Ile His Phe Ser Gly His Val Phe Thr Val Arg Lys
        1155                1160                1165

Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215
```

```
Val Tyr Ser Asp Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Ser Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340

Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420

Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Ser Leu Asp Pro Pro Leu Leu Thr
    1490                1495                1500

Arg Tyr Leu Arg Ile His Pro Gln Ser Trp Val His Gln Ile Ala Leu
1505                1510                1515                1520

Arg Met Glu Val Leu Gly Cys Glu Ala Gln Asp Leu Tyr
                1525                1530
```

<210> SEQ ID NO 16
<211> LENGTH: 15
<212> TYPE: PRT
<213> ORGANISM: Homo sapiens
<220> FEATURE:
<223> OTHER INFORMATION: Immunogenic cluster identified in FVIII

<400> SEQUENCE: 16

```
Asp His Leu Phe Asn Ile Ala Lys Pro Arg Pro Pro Trp Met Gly
1               5                   10                  15
```

<210> SEQ ID NO 17
<211> LENGTH: 18
<212> TYPE: PRT
<213> ORGANISM: Homo sapiens
<220> FEATURE:

<223> OTHER INFORMATION: Immunogenic cluster identified in FVIII

<400> SEQUENCE: 17

Tyr Asp Thr Val Val Ile Thr Leu Lys Asn Met Ala Ser His Pro Val
1 5 10 15

Ser Leu

<210> SEQ ID NO 18
<211> LENGTH: 16
<212> TYPE: PRT
<213> ORGANISM: Homo sapiens
<220> FEATURE:
<223> OTHER INFORMATION: Immunogenic cluster identified in FVIII

<400> SEQUENCE: 18

Val Trp Gln Val Leu Lys Glu Asn Gly Pro Met Ala Ser Asp Pro Leu
1 5 10 15

<210> SEQ ID NO 19
<211> LENGTH: 18
<212> TYPE: PRT
<213> ORGANISM: Homo sapiens
<220> FEATURE:
<223> OTHER INFORMATION: Immunogenic cluster identified in FVIII

<400> SEQUENCE: 19

Ser Asp Pro Leu Cys Leu Thr Tyr Ser Tyr Leu Ser His Val Asp Leu
1 5 10 15

Val Lys

<210> SEQ ID NO 20
<211> LENGTH: 16
<212> TYPE: PRT
<213> ORGANISM: Homo sapiens
<220> FEATURE:
<223> OTHER INFORMATION: Immunogenic cluster identified in FVIII

<400> SEQUENCE: 20

His Val Asp Leu Val Lys Asp Leu Asn Ser Gly Leu Ile Gly Ala Leu
1 5 10 15

<210> SEQ ID NO 21
<211> LENGTH: 18
<212> TYPE: PRT
<213> ORGANISM: Homo sapiens
<220> FEATURE:
<223> OTHER INFORMATION: Immunogenic cluster identified in FVIII

<400> SEQUENCE: 21

Thr Gln Thr Leu His Lys Phe Ile Leu Leu Phe Ala Val Phe Asp Glu
1 5 10 15

Gly Lys

<210> SEQ ID NO 22
<211> LENGTH: 15
<212> TYPE: PRT
<213> ORGANISM: Homo sapiens
<220> FEATURE:
<223> OTHER INFORMATION: Immunogenic cluster identified in FVIII

<400> SEQUENCE: 22

Gly Lys Ser Trp His Ser Glu Thr Lys Asn Ser Leu Met Gln Asp
1 5 10 15

<210> SEQ ID NO 23
<211> LENGTH: 17
<212> TYPE: PRT
<213> ORGANISM: Homo sapiens
<220> FEATURE:
<223> OTHER INFORMATION: Immunogenic cluster identified in FVIII

<400> SEQUENCE: 23

Met His Thr Val Asn Gly Tyr Val Asn Arg Ser Leu Pro Gly Leu Ile
1 5 10 15

Gly

<210> SEQ ID NO 24
<211> LENGTH: 17
<212> TYPE: PRT
<213> ORGANISM: Homo sapiens
<220> FEATURE:
<223> OTHER INFORMATION: Immunogenic cluster identified in FVIII

<400> SEQUENCE: 24

Gly His Thr Phe Leu Val Arg Asn His Arg Gln Ala Ser Leu Glu Ile
1 5 10 15

Ser

<210> SEQ ID NO 25
<211> LENGTH: 17
<212> TYPE: PRT
<213> ORGANISM: Homo sapiens
<220> FEATURE:
<223> OTHER INFORMATION: Immunogenic cluster identified in FVIII

<400> SEQUENCE: 25

Ile Ser Pro Ile Thr Phe Leu Thr Ala Gln Thr Leu Leu Met Asp Leu
1 5 10 15

Gly

<210> SEQ ID NO 26
<211> LENGTH: 19
<212> TYPE: PRT
<213> ORGANISM: Homo sapiens
<220> FEATURE:
<223> OTHER INFORMATION: Immunogenic cluster identified in FVIII

<400> SEQUENCE: 26

Asp Arg Ser Tyr Lys Ser Gln Tyr Leu Asn Asn Gly Pro Gln Arg Ile
1 5 10 15

Gly Arg Lys

<210> SEQ ID NO 27
<211> LENGTH: 19
<212> TYPE: PRT
<213> ORGANISM: Homo sapiens
<220> FEATURE:
<223> OTHER INFORMATION: Immunogenic cluster identified in FVIII

<400> SEQUENCE: 27

Gly Asp Thr Leu Leu Ile Ile Phe Lys Asn Gln Ala Ser Arg Pro Tyr
1 5 10 15

Asn Ile Tyr

<210> SEQ ID NO 28
<211> LENGTH: 19
<212> TYPE: PRT
<213> ORGANISM: Homo sapiens
<220> FEATURE:
<223> OTHER INFORMATION: Immunogenic cluster identified in FVIII

<400> SEQUENCE: 28

Ile Thr Asp Val Arg Pro Leu Tyr Ser Arg Arg Leu Pro Lys Gly Val
1               5                   10                  15

Lys His Leu

<210> SEQ ID NO 29
<211> LENGTH: 22
<212> TYPE: PRT
<213> ORGANISM: Homo sapiens
<220> FEATURE:
<223> OTHER INFORMATION: Immunogenic cluster identified in FVIII

<400> SEQUENCE: 29

Pro Arg Cys Leu Thr Arg Tyr Tyr Ser Ser Phe Val Asn Met Glu Arg
1               5                   10                  15

Asp Leu Ala Ser Gly Leu
            20

<210> SEQ ID NO 30
<211> LENGTH: 18
<212> TYPE: PRT
<213> ORGANISM: Homo sapiens
<220> FEATURE:
<223> OTHER INFORMATION: Immunogenic cluster identified in FVIII

<400> SEQUENCE: 30

Thr Glu Asn Ile Gln Arg Phe Leu Pro Asn Pro Ala Gly Val Gln Leu
1               5                   10                  15

Glu Asp

<210> SEQ ID NO 31
<211> LENGTH: 19
<212> TYPE: PRT
<213> ORGANISM: Homo sapiens
<220> FEATURE:
<223> OTHER INFORMATION: Immunogenic cluster identified in FVIII

<400> SEQUENCE: 31

Pro Glu Phe Gln Ala Ser Asn Ile Met His Ser Ile Asn Gly Tyr Val
1               5                   10                  15

Phe Asp Ser

<210> SEQ ID NO 32
<211> LENGTH: 17
<212> TYPE: PRT
<213> ORGANISM: Homo sapiens
<220> FEATURE:
<223> OTHER INFORMATION: Immunogenic cluster identified in FVIII

<400> SEQUENCE: 32

Glu Val Ala Tyr Trp Tyr Ile Leu Ser Ile Gly Ala Gln Thr Asp Phe
1               5                   10                  15

Leu

<210> SEQ ID NO 33
<211> LENGTH: 15
<212> TYPE: PRT
<213> ORGANISM: Homo sapiens
<220> FEATURE:
<223> OTHER INFORMATION: Immunogenic cluster identified in FVIII

<400> SEQUENCE: 33

Glu Thr Val Phe Met Ser Met Glu Asn Pro Gly Leu Trp Ile Leu
1 5 10 15

<210> SEQ ID NO 34
<211> LENGTH: 16
<212> TYPE: PRT
<213> ORGANISM: Homo sapiens
<220> FEATURE:
<223> OTHER INFORMATION: Immunogenic cluster identified in FVIII

<400> SEQUENCE: 34

Ile Ser Ala Tyr Leu Leu Ser Lys Asn Asn Ala Ile Glu Pro Arg Ser
1 5 10 15

<210> SEQ ID NO 35
<211> LENGTH: 15
<212> TYPE: PRT
<213> ORGANISM: Homo sapiens
<220> FEATURE:
<223> OTHER INFORMATION: Immunogenic cluster identified in FVIII

<400> SEQUENCE: 35

Pro Arg Ser Phe Gln Lys Lys Thr Arg His Tyr Phe Ile Ala Ala
1 5 10 15

<210> SEQ ID NO 36
<211> LENGTH: 16
<212> TYPE: PRT
<213> ORGANISM: Homo sapiens
<220> FEATURE:
<223> OTHER INFORMATION: Immunogenic cluster identified in FVIII

<400> SEQUENCE: 36

Met Val Thr Phe Arg Asn Gln Ala Ser Arg Pro Tyr Ser Phe Tyr Ser
1 5 10 15

<210> SEQ ID NO 37
<211> LENGTH: 16
<212> TYPE: PRT
<213> ORGANISM: Homo sapiens
<220> FEATURE:
<223> OTHER INFORMATION: Immunogenic cluster identified in FVIII

<400> SEQUENCE: 37

Lys Thr Tyr Phe Trp Lys Val Gln His His Met Ala Pro Thr Lys Asp
1 5 10 15

<210> SEQ ID NO 38
<211> LENGTH: 21
<212> TYPE: PRT
<213> ORGANISM: Homo sapiens
<220> FEATURE:
<223> OTHER INFORMATION: Immunogenic cluster identified in FVIII

<400> SEQUENCE: 38

Asp Pro Thr Phe Lys Glu Asn Tyr Arg Phe His Ala Ile Asn Gly Tyr
1 5 10 15

Ile Met Asp Thr Leu
20

<210> SEQ ID NO 39
<211> LENGTH: 19
<212> TYPE: PRT
<213> ORGANISM: Homo sapiens
<220> FEATURE:

<223> OTHER INFORMATION: Immunogenic cluster identified in FVIII

<400> SEQUENCE: 39

Asp Gln Arg Ile Arg Trp Tyr Leu Leu Ser Met Gly Ser Asn Glu Asn
1 5 10 15

Ile His Ser

<210> SEQ ID NO 40
<211> LENGTH: 16
<212> TYPE: PRT
<213> ORGANISM: Homo sapiens
<220> FEATURE:
<223> OTHER INFORMATION: Immunogenic cluster identified in FVIII

<400> SEQUENCE: 40

Met Ser Thr Leu Phe Leu Val Tyr Ser Asn Lys Cys Gln Thr Pro Leu
1 5 10 15

<210> SEQ ID NO 41
<211> LENGTH: 19
<212> TYPE: PRT
<213> ORGANISM: Homo sapiens
<220> FEATURE:
<223> OTHER INFORMATION: Immunogenic cluster identified in FVIII

<400> SEQUENCE: 41

Pro Lys Leu Ala Arg Leu His Tyr Ser Gly Ser Ile Asn Ala Trp Ser
1 5 10 15

Thr Lys Glu

<210> SEQ ID NO 42
<211> LENGTH: 19
<212> TYPE: PRT
<213> ORGANISM: Homo sapiens
<220> FEATURE:
<223> OTHER INFORMATION: Immunogenic cluster identified in FVIII

<400> SEQUENCE: 42

Ser Ser Leu Tyr Ile Ser Gln Phe Ile Ile Met Tyr Ser Leu Asp Gly
1 5 10 15

Lys Lys Trp

<210> SEQ ID NO 43
<211> LENGTH: 18
<212> TYPE: PRT
<213> ORGANISM: Homo sapiens
<220> FEATURE:
<223> OTHER INFORMATION: Immunogenic cluster identified in FVIII

<400> SEQUENCE: 43

Gly Lys Lys Trp Gln Thr Tyr Arg Gly Asn Ser Thr Gly Thr Leu Met
1 5 10 15

Val Phe

<210> SEQ ID NO 44
<211> LENGTH: 17
<212> TYPE: PRT
<213> ORGANISM: Homo sapiens
<220> FEATURE:
<223> OTHER INFORMATION: Immunogenic cluster identified in FVIII

<400> SEQUENCE: 44

Ile Ala Arg Tyr Ile Arg Leu His Pro Thr His Tyr Ser Ile Arg Ser
1 5 10 15

Thr

<210> SEQ ID NO 45
<211> LENGTH: 15
<212> TYPE: PRT
<213> ORGANISM: Homo sapiens
<220> FEATURE:
<223> OTHER INFORMATION: Immunogenic cluster identified in FVIII

<400> SEQUENCE: 45

Ser Ser Tyr Phe Thr Asn Met Phe Ala Thr Trp Ser Pro Ser Lys
1 5 10 15

<210> SEQ ID NO 46
<211> LENGTH: 17
<212> TYPE: PRT
<213> ORGANISM: Homo sapiens
<220> FEATURE:
<223> OTHER INFORMATION: Immunogenic cluster identified in FVIII

<400> SEQUENCE: 46

Lys Ala Arg Leu His Leu Gln Gly Arg Ser Asn Ala Trp Arg Pro Gln
1 5 10 15

Val

<210> SEQ ID NO 47
<211> LENGTH: 17
<212> TYPE: PRT
<213> ORGANISM: Homo sapiens
<220> FEATURE:
<223> OTHER INFORMATION: Immunogenic cluster identified in FVIII

<400> SEQUENCE: 47

Trp Leu Gln Val Asp Phe Gln Lys Thr Met Lys Val Thr Gly Val Thr
1 5 10 15

Thr

<210> SEQ ID NO 48
<211> LENGTH: 19
<212> TYPE: PRT
<213> ORGANISM: Homo sapiens
<220> FEATURE:
<223> OTHER INFORMATION: Immunogenic cluster identified in FVIII

<400> SEQUENCE: 48

Thr Ser Met Tyr Val Lys Glu Phe Leu Ile Ser Ser Ser Gln Asp Gly
1 5 10 15

His Gln Trp

<210> SEQ ID NO 49
<211> LENGTH: 19
<212> TYPE: PRT
<213> ORGANISM: Homo sapiens
<220> FEATURE:
<223> OTHER INFORMATION: Immunogenic cluster identified in FVIII

<400> SEQUENCE: 49

Gln Asp Ser Phe Thr Pro Val Val Asn Ser Leu Asp Pro Pro Leu Leu
1 5 10 15

Thr Arg Tyr

<210> SEQ ID NO 50
<211> LENGTH: 15

```
<212> TYPE: PRT
<213> ORGANISM: Homo sapiens
<220> FEATURE:
<223> OTHER INFORMATION: Immunogenic cluster identified in FVIII

<400> SEQUENCE: 50

Pro Gln Ser Trp Val His Gln Ile Ala Leu Arg Met Glu Val Leu
1               5                   10                  15


<210> SEQ ID NO 51
<211> LENGTH: 1533
<212> TYPE: PRT
<213> ORGANISM: Artificial Sequence
<220> FEATURE:
<221> NAME/KEY: SIGNAL
<222> LOCATION: 1..19
<220> FEATURE:
<223> OTHER INFORMATION: FVIII-A1A2-3M

<400> SEQUENCE: 51

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asp His Arg Gln Ala Ser
    290                 295                 300
```

```
Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser His Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Glu Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720
```

```
Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asp Pro Leu Ala Trp
        755                 760                 765

Asp Asn His Tyr Gly Thr Gln Ile Pro Lys Glu Glu Trp Lys Ser Gln
    770                 775                 780

Glu Lys Ser Pro Glu Lys Thr Ala Phe Lys Lys Lys Asp Thr Ile Leu
785                 790                 795                 800

Ser Leu Asn Ala Cys Glu Ser Asn His Ala Ile Ala Ala Ile Asn Glu
                805                 810                 815

Gly Gln Asn Lys Pro Glu Ile Glu Val Thr Trp Ala Lys Gln Gly Arg
            820                 825                 830

Thr Glu Arg Leu Cys Ser Gln Asn Pro Pro Val Leu Lys Arg His Gln
        835                 840                 845

Arg Glu Ile Thr Arg Thr Thr Leu Gln Ser Asp Gln Glu Glu Ile Asp
    850                 855                 860

Tyr Asp Asp Thr Ile Ser Val Glu Met Lys Lys Glu Asp Phe Asp Ile
865                 870                 875                 880

Tyr Asp Glu Asp Glu Asn Gln Ser Pro Arg Ser Phe Gln Lys Lys Thr
                885                 890                 895

Arg His Tyr Phe Ile Ala Ala Val Glu Arg Leu Trp Asp Tyr Gly Met
            900                 905                 910

Ser Ser Ser Pro His Val Leu Arg Asn Arg Ala Gln Ser Gly Ser Val
        915                 920                 925

Pro Gln Phe Lys Lys Val Val Phe Gln Glu Phe Thr Asp Gly Ser Phe
    930                 935                 940

Thr Gln Pro Leu Tyr Arg Gly Glu Leu Asn Glu His Leu Gly Leu Leu
945                 950                 955                 960

Gly Pro Tyr Ile Arg Ala Glu Val Glu Asp Asn Ile Met Val Thr Phe
                965                 970                 975

Arg Asn Gln Ala Ser Arg Pro Tyr Ser Phe Tyr Ser Ser Leu Ile Ser
            980                 985                 990

Tyr Glu Glu Asp Gln Arg Gln Gly Ala Glu Pro Arg Lys Asn Phe Val
        995                 1000                1005

Lys Pro Asn Glu Thr Lys Thr Tyr Phe Trp Lys Val Gln His His Met
    1010                1015                1020

Ala Pro Thr Lys Asp Glu Phe Asp Cys Lys Ala Trp Ala Tyr Phe Ser
1025                1030                1035                1040

Asp Val Asp Leu Glu Lys Asp Val His Ser Gly Leu Ile Gly Pro Leu
                1045                1050                1055

Leu Val Cys His Thr Asn Thr Leu Asn Pro Ala His Gly Arg Gln Val
            1060                1065                1070

Thr Val Gln Glu Phe Ala Leu Phe Phe Thr Ile Phe Asp Glu Thr Lys
        1075                1080                1085

Ser Trp Tyr Phe Thr Glu Asn Met Glu Arg Asn Cys Arg Ala Pro Cys
    1090                1095                1100

Asn Ile Gln Met Glu Asp Pro Thr Phe Lys Glu Asn Tyr Arg Phe His
1105                1110                1115                1120

Ala Ile Asn Gly Tyr Ile Met Asp Thr Leu Pro Gly Leu Val Met Ala
                1125                1130                1135

Gln Asp Gln Arg Ile Arg Trp Tyr Leu Leu Ser Met Gly Ser Asn Glu
```

```
        1140                1145                1150

Asn Ile His Ser Ile His Phe Ser Gly His Val Phe Thr Val Arg Lys
    1155                1160                1165

Lys Glu Glu Tyr Lys Met Ala Leu Tyr Asn Leu Tyr Pro Gly Val Phe
    1170                1175                1180

Glu Thr Val Glu Met Leu Pro Ser Lys Ala Gly Ile Trp Arg Val Glu
1185                1190                1195                1200

Cys Leu Ile Gly Glu His Leu His Ala Gly Met Ser Thr Leu Phe Leu
                1205                1210                1215

Val Tyr Ser Asn Lys Cys Gln Thr Pro Leu Gly Met Ala Ser Gly His
            1220                1225                1230

Ile Arg Asp Phe Gln Ile Thr Ala Ser Gly Gln Tyr Gly Gln Trp Ala
        1235                1240                1245

Pro Lys Leu Ala Arg Leu His Tyr Ser Gly Ser Ile Asn Ala Trp Ser
    1250                1255                1260

Thr Lys Glu Pro Phe Ser Trp Ile Lys Val Asp Leu Leu Ala Pro Met
1265                1270                1275                1280

Ile Ile His Gly Ile Lys Thr Gln Gly Ala Arg Gln Lys Phe Ser Ser
                1285                1290                1295

Leu Tyr Ile Ser Gln Phe Ile Ile Met Tyr Ser Leu Asp Gly Lys Lys
            1300                1305                1310

Trp Gln Thr Tyr Arg Gly Asn Ser Thr Gly Thr Leu Met Val Phe Phe
        1315                1320                1325

Gly Asn Val Asp Ser Ser Gly Ile Lys His Asn Ile Phe Asn Pro Pro
    1330                1335                1340

Ile Ile Ala Arg Tyr Ile Arg Leu His Pro Thr His Tyr Ser Ile Arg
1345                1350                1355                1360

Ser Thr Leu Arg Met Glu Leu Met Gly Cys Asp Leu Asn Ser Cys Ser
                1365                1370                1375

Met Pro Leu Gly Met Glu Ser Lys Ala Ile Ser Asp Ala Gln Ile Thr
            1380                1385                1390

Ala Ser Ser Tyr Phe Thr Asn Met Phe Ala Thr Trp Ser Pro Ser Lys
        1395                1400                1405

Ala Arg Leu His Leu Gln Gly Arg Ser Asn Ala Trp Arg Pro Gln Val
    1410                1415                1420

Asn Asn Pro Lys Glu Trp Leu Gln Val Asp Phe Gln Lys Thr Met Lys
1425                1430                1435                1440

Val Thr Gly Val Thr Thr Gln Gly Val Lys Ser Leu Leu Thr Ser Met
                1445                1450                1455

Tyr Val Lys Glu Phe Leu Ile Ser Ser Ser Gln Asp Gly His Gln Trp
            1460                1465                1470

Thr Leu Phe Phe Gln Asn Gly Lys Val Lys Val Phe Gln Gly Asn Gln
        1475                1480                1485

Asp Ser Phe Thr Pro Val Val Asn Ser Leu Asp Pro Pro Leu Leu Thr
    1490                1495                1500

Arg Tyr Leu Arg Ile His Pro Gln Ser Trp Val His Gln Ile Ala Leu
1505                1510                1515                1520

Arg Met Glu Val Leu Gly Cys Glu Ala Gln Asp Leu Tyr
                1525                1530
```

<210> SEQ ID NO 52
<211> LENGTH: 4605
<212> TYPE: DNA
<213> ORGANISM: Artificial Sequence
<220> FEATURE:
<223> OTHER INFORMATION: FVIII-19M na

<400> SEQUENCE: 52
atgcagatcg agctgtctac ctgcttcttc ctgtgcctgc tgcggttctg cttcagcgcc 60
acccggcggt actacctggg cgccgtggaa ctgagctggg actacatgca gagcgacctg 120
ggcgagctgc ccgtggacgc cagattcccc ccaagagtgc ccaagagctt ccccttcaac 180
acctccgtgg tgtacaagaa aaccctgttc gtcgagttca ccgaccacct gttctccatc 240
gccaagccca gacccccctg gatgggcctg ctgggcccta caatccaggc cgaggtgtac 300
gacaccgtgg tcatcaccct gaagaacatg gccacccacc ccgtgtccct gcacgccgtg 360
ggcgtgtcct actggaaggc cagcgagggc gccgagtacg acgaccagac cagccagcgc 420
gagaaagagg acgacaaagt ctttcctggc ggcagccata cctacgtgtg gcaggtctcc 480
aaagaaaacg gccccatggc ctccgacccc cagtgcctga cctacagcta cctgagccac 540
gtggacctgg ccaaggacct gaacagcggc ctgatcggcg ccctgctcgt gtgcagagag 600
ggcagcctgg ccaaagagaa aacccagacc ctgcacaagt tcatcctgct gttcgccgtg 660
ttcgacgagg gcaagagctg gcacagcgag acaaaggaca gcctgatgca ggaccgggac 720
gccgcctctg ccagagcctg gcctaagatg cacaccgtga acggctacgt gaacagaagc 780
ctgcccggac tgaccggctg ccaccggaag tccgtgtact ggcacgtgat cggcatgggt 840
accacccccg aggtgcacag catctttctg gaaggacaca ccttcctcgt gcgggaccac 900
cggcaggcca gcctggaaat cagccctatc accttcctga ccgcccagac actgctgatg 960
gacctgggcc agttcctgct gttttgccac atcagcagcc accagcacga cggcatggaa 1020
gcctacgtga aggtggacag ctgccccgag gaaccccagc tgcggatgaa gaacaacgag 1080
gaagccgagg actacgacga cgacctgacc gacagcgaga tggacgtcgt cagattcgat 1140
gacgacaaca gccccagctt catccagatc agaagcgtgg ccaagaagca ccccaagacc 1200
tgggtgcact atatcgccgc cgaggaagag gactgggact acgcccctct ggtgctggcc 1260
cccgacgaca gaagccacaa gagccagtac ctgaacaatg gcccccagcg gatcggccgg 1320
aagtacaaga aagtgcggtt catggcctac accgacgaga cattcaagac cagagaggcc 1380
atccagcacg agagcggcat cctgggcccc ctgctgtacg gcgaagtggg cgacaccctg 1440
ctgattatct tcaagaacca ggccagccgg ccctacaaca tctaccccca cggcatcacc 1500
gacgtgcggc ccctgtacga gagacggctg cccaagggcg tgaagcacct gaaggacttc 1560
cccatcctgc ccggggagat cttcaagtac aagtggaccg tgaccgtgga agatggcccc 1620
accaagagcg accccagatg cctgacccgg tactacagca gccacgtgaa catggaacgg 1680
gacctggcct ccgggctgat cggccctctg ctgatctgct acaaagaaag cgtggaccag 1740
cggggcaacc agatcatgag cgacaagcgg aacgtgatcc tgttcagcgt gttcgatgag 1800
aacagaagct ggtatctgac cgagaatatc cagcggttcc tgcccgagcc tgccggcgtg 1860
cagctggaag atcccgagtt ccaggccagc aacatcatgc actccatcaa tggctacgtg 1920
ttcgacagcc tgcagctgag cgtgtgcctg cacgaggtgg cctactggta catcctgagc 1980
atcggcgccc agaccgactt cctgagcgtg ttcttcagcg gctacacctt caagcacaag 2040
atggtgtacg aggataccct gaccctgttc cccttctccg gcgaaaccgt gttcatgagc 2100
atggaaaacc ccggcaactg gattctgggc tgccacaaca gcgacttccg gaaccggggc 2160
atgaccgccc tgctgaaggt gtccagctgc gacaagaaca ccggcgacta ctacgaggac 2220

```
agctacgagg atatcagcgc cagcctgctg agcaagaaca acgccatcga gcctcggagc   2280
ttctcccagg atcctctggc ctgggacaac cactacggca cccagatccc caaagaggaa   2340
tggaagtccc aggaaaagag ccccgagaaa accgccttca agaagaagga caccatcctg   2400
agcctgaacg cctgcgagag caaccacgcc attgccgcca tcaacgaggg ccagaacaag   2460
cccgagatcg aagtgacctg ggctaagcag ggccggaccg agagactgtg cagccagaac   2520
ccccccgtgc tgaagcggca ccagagagag atcacccgga ccaccctgca gagcgaccag   2580
gaagagatcg actacgacga caccatcagc gtcgagatga agaaagagga cttcgacatc   2640
tacgacgagg acgagaacca gagcccccgg tccttccaga agaaaacccg gcactacttt   2700
atcgccgccg tggaacggct gtgggactac ggcatgagca gcagccccca cgtgctgcgg   2760
aatagagccc agagcggcag cgtgccccag ttcaagaaag tggtgttcca ggagttcacc   2820
gacggcagct tcacccagcc tctgtaccgg ggcgagctga acgagcacct gggcctgctg   2880
ggcccctaca tccgggccga ggtggaagat aacatcatgg tcaccttccg gaaccaggcc   2940
agccggccct acagcttcta cagcagcctg atctcctacg aagaggacca gcggcagggc   3000
gccgagcccc ggaagaactt cgtgaagccc aacgagacaa agacctactt ctgggaggtg   3060
cagcaccaca tggcccccac caaggacgaa ttcgactgca aggcctgggc ctacttcagc   3120
gacgtggacc tggaaaagga cgtgcacagc ggcctgatcg gcccccctgct cgtgtgccac   3180
accaacaccc tgaaccccgc ccacggccgg caggtcacag tgcaggaatt tgccctgttc   3240
ttcaccatct tcgacgagac taagagctgg tacttcaccg agaacatgga acggaactgc   3300
agagccccct gcaacatcca gatggaagat cccaccttca aagagaacta ccggttccac   3360
gccatcaatg gctacatcat ggacaccctg cccggcctgg tcatggccca ggaccagaga   3420
atccggtggt atctgctgag catgggcagc aacgagaaca tccacagcat ccacttcagc   3480
ggccacgtgt tcaccgtgcg gaagaaagaa gagtacaaga tggccctgta caacctgtac   3540
cccggcgtgt tcgagacagt ggaaatgctg cccagcaagg ccggcatctg gcgggtggaa   3600
tgtctgatcg gcgagcatct gcacgccggc atgtccaccc tgtttctggt gtacagcgac   3660
aagtgccaga accccctggg catggccagc ggccacatcc gggatttcca gatcaccgcc   3720
tccggccagt acggccagtg ggcccctaaa ctggcccggc tgcactacag cggcggcatc   3780
aacgcctggt ccaccaaaga gcccttcagc tggatcaagg tggacctgct ggcccccatg   3840
attatccacg gcatcaagac acagggcgcc agacagaagt tcagcagcct gtacatcagc   3900
cagttcatca tcatgtacag cctggatggc aagaagtggc agacctaccg gggcaacagc   3960
accggcaccc tgatggtgtt cttcggcaac gtggacagca gcggcatcaa gcacaacatc   4020
ttcaaccccc ccatcattgc ccggtacatc cggctgcacc ccacccacta cagcatccgg   4080
tccaccctgc ggatggaact gatgggctgc gacctgaaca gctgctccat gcctctgggc   4140
atggaaagca aggccatcag cgacgcccag atcacagcca gcagctactt caccaacatg   4200
ttcgccacct ggtccccatc caaggccaga ctgcatctgc agggcagaag caatgcctgg   4260
cggcctcagg tcaacaaccc caaagaatgg ctccaggtgg acttccagaa aaccatgaag   4320
gtcacaggcg tgaccaccca gggcgtgaag tccctgctga cctctatgta cgtgaaagag   4380
ttcctgatct ccagcagcca ggacggccac cagtggaccc tgttctttca gaacggcaaa   4440
gtgaaagtgt tccagggcaa ccaggactcc ttcacccccg tggtcaacac cctggacccc   4500
ccactgctga ccagatacct gagaatccac ccccagagct gggcccacca gatcgccctg   4560
agaatggaag tgctgggatg cgaggcccag gatctgtact gatag                   4605
```

<210> SEQ ID NO 53
<211> LENGTH: 4605
<212> TYPE: DNA
<213> ORGANISM: Artificial Sequence
<220> FEATURE:
<223> OTHER INFORMATION: FVIII-6rs na

<400> SEQUENCE: 53
atgcagatcg agctgtctac ctgcttcttc ctgtgcctgc tgcggttctg cttcagcgcc 60
acccggcggt actacctggg cgccgtggaa ctgagctggg actacatgca gagcgacctg 120
ggcgagctgc ccgtggacgc cagattcccc ccaagagtgc ccaagagctt ccccttcaac 180
acctccgtgg tgtacaagaa aaccctgttc gtcgagttca ccgaccacct gttcaatatc 240
gccaagccca gacccccctg gatgggcctg ctgggcccta caatccaggc cgaggtgtac 300
gacaccgtgg tcatcaccct gaagaacatg gccagccacc ccgtgtccct gcacgccgtg 360
ggcgtgtcct actggaaggc cagcgagggc gccgagtacg acgaccagac cagccagcgc 420
gagaaagagg acgacaaagt ctttcctggc ggcagccata cctacgtgtg gcaggtcctg 480
aaagaaaacg gccccatggc ctccgacccc ctgtgcctga cctacagcta cctgagccac 540
gtggacctgg tcaaggacct gaacagcggc ctgatcggcg ccctgctcgt gtgcagagag 600
ggcagcctgg ccaaagagaa aacccagacc ctgcacaagt tcatcctgct gttcgccgtg 660
ttcgacgagg gcaagagctg gcacagcgag acaaagaaca gcctgatgca ggaccgggac 720
gccgcctctg ccagagcctg gcctaagatg cacaccgtga acggctacgt gaacagaagc 780
ctgcccggac tgatcggctg ccaccggaag tccgtgtact ggcacgtgat cggcatgggt 840
accacccccg aggtgcacag catctttctg gaaggacaca ccttcctcgt gcggaaccac 900
cggcaggcca gcctggaaat cagccctatc accttcctga ccgcccagac actgctgatg 960
gacctgggcc agttcctgct gttttgccac atcagcagcc accagcacga cggcatggaa 1020
gcctacgtga aggtggacag ctgccccgag gaaccccagc tgcggatgaa gaacaacgag 1080
gaagccgagg actacgacga cgacctgacc gacagcgaga tggacgtcgt cagattcgat 1140
gacgacaaca gccccagctt catccagatc agaagcgtgg ccaagaagca ccccaagacc 1200
tgggtgcact atatcgccgc cgaggaagag gactgggact acgcccctct ggtgctggcc 1260
cccgacgaca gaagctacaa gagccagtac ctgaacaatg gcccccagcg gatcggccgg 1320
aagtacaaga aagtgcggtt catggcctac accgacgaga cattcaagac cagagaggcc 1380
atccagcacg agagcggcat cctgggcccc ctgctgtacg gcgaagtggg cgacaccctg 1440
ctgattatct tcaagaacca ggccagccgg ccctacaaca tctaccccca cggcatcacc 1500
gacgtgcggc ccctgtacag cagacggctg cccaagggcg tgaagcacct gaaggacttc 1560
cccatcctgc ccggggagat cttcaagtac aagtggaccg tgaccgtgga agatggcccc 1620
accaagagcg accccagatg cctgacccgg tactacagca gcttcgtgaa catggaacgg 1680
gacctggcct ccgggctgat cggccctctg ctgatctgct acaaagaaag cgtggaccag 1740
cggggcaacc agatcatgag cgacaagcgg aacgtgatcc tgttcagcgt gttcgatgag 1800
aacagaagct ggtatctgac cgagaatatc cagcggttcc tgcccaaccc tgccggcgtg 1860
cagctggaag atcccgagtt ccaggccagc aacatcatgc actccatcaa tggctacgtg 1920
ttcgacagcc tgcagctgag cgtgtgcctg cacgaggtgg cctactggta catcctgagc 1980
atcggcgccc agaccgactt cctgagcgtg ttcttcagcg gctacacctt caagcacaag 2040

-continued

```
atggtgtacg aggataccct gaccctgttc cccttctccg gcgaaaccgt gttcatgagc   2100
atggaaaacc ccggcctgtg gattctgggc tgccacaaca gcgacttccg gaaccggggc   2160
atgaccgccc tgctgaaggt gtccagctgc gacaagaaca ccggcgacta ctacgaggac   2220
agctacgagg atatcagcgc ctacctgctg agcaagaaca acgccatcga gcctcggagc   2280
ttctcccagg atcctctggc ctgggacaac cactacggca cccagatccc caaagaggaa   2340
tggaagtccc aggaaaagag ccccgagaaa accgccttca agaagaagga caccatcctg   2400
agcctgaacg cctgcgagag caaccacgcc attgccgcca tcaacgaggg ccagaacaag   2460
cccgagatcg aagtgacctg ggctaagcag ggccggaccg agagactgtg cagccagaac   2520
ccccccgtgc tgaagcggca ccagagagag atcacccgga ccaccctgca gagcgaccag   2580
gaagagatcg actacgacga caccatcagc gtcgagatga agaaagagga cttcgacatc   2640
tacgacgagg acgagaacca gagcccccgg tccttccaga agaaaacccg gcactacttt   2700
atcgccgccg tggaacggct gtgggactac ggcatgagca gcagccccca cgtgctgcgg   2760
aatagagccc agagcggcag cgtgccccag ttcaagaaag tggtgttcca ggagttcacc   2820
gacggcagct tcacccagcc tctgtaccgg ggcgagctga acgagcacct gggcctgctg   2880
ggcccctaca tccgggccga ggtggaagat aacatcatgg tcaccttccg gaaccaggcc   2940
agccggccct acagcttcta cagcagcctg atctcctacg aagaggacca gcggcagggc   3000
gccgagcccc ggaagaactt cgtgaagccc aacgagacaa agacctactt ctggaaggtg   3060
cagcaccaca tggcccccac caaggacgaa ttcgactgca aggcctgggc ctacttcagc   3120
gacgtggacc tggaaaagga cgtgcacagc ggcctgatcg gcccccctgct cgtgtgccac   3180
accaacaccc tgaaccccgc ccacggccgg caggtcacag tgcaggaatt tgccctgttc   3240
ttcaccatct tcgacgagac taagagctgg tacttcaccg agaacatgga acggaactgc   3300
agagcccccct gcaacatcca gatggaagat cccaccttca aagagaacta ccggttccac   3360
gccatcaatg gctacatcat ggacaccctg cccggcctgg tcatggccca ggaccagaga   3420
atccggtggt atctgctgag catgggcagc aacgagaaca tccacagcat ccacttcagc   3480
ggccacgtgt tcaccgtgcg gaagaaagaa gagtacaaga tggccctgta caacctgtac   3540
cccggcgtgt tcgagacagt ggaaatgctg cccagcaagg ccggcatctg gcgggtggaa   3600
tgtctgatcg gcgagcatct gcacgccggc atgtccaccc tgtttctggt gtacagcaac   3660
aagtgccaga ccccccctggg catggccagc ggccacatcc gggatttcca gatcaccgcc   3720
tccggccagt acggccagtg ggcccctaaa ctggcccggc tgcactacag cggcagcatc   3780
aacgcctggt ccaccaaaga gcccttcagc tggatcaagg tggacctgct ggcccccatg   3840
attatccacg gcatcaagac acagggcgcc agacagaagt tcagcagcct gtacatcagc   3900
cagttcatca tcatgtacag cctggatggc aagaagtggc agacctaccg gggcaacagc   3960
accggcaccc tgatggtgtt cttcggcaac gtggacagca gcggcatcaa gcacaacatc   4020
ttcaaccccc ccatcattgc ccggtacatc cggctgcacc ccacccacta cagcatccgg   4080
tccaccctgc ggatggaact gatgggctgc gacctgaaca gctgctccat gcctctgggc   4140
atggaaagca aggccatcag cgacgcccag atcacagcca gcagctactt caccaacatg   4200
ttcgccacct ggtccccatc caaggccaga ctgcatctgc agggcagaag caatgcctgg   4260
cggcctcagg tcaacaaccc caaagaatgg ctccaggtgg acttccagaa aaccatgaag   4320
gtcacaggcg tgaccaccca gggcgtgaag tccctgctga cctctatgta cgtgaaagag   4380
ttcctgatct ccagcagcca ggacggccac cagtggaccc tgttctttca gaacggcaaa   4440
```

-continued

```
gtgaaagtgt tccagggcaa ccaggactcc ttcacccccg tggtcaactc cctggacccc   4500

ccactgctga ccagatacct gagaatccac ccccagagct gggtgcacca gatcgccctg   4560

agaatggaag tgctgggatg cgaggcccag gatctgtact gatag                   4605


<210> SEQ ID NO 54
<211> LENGTH: 16
<212> TYPE: PRT
<213> ORGANISM: Artificial Sequence
<220> FEATURE:
<223> OTHER INFORMATION: Immunogenic cluster identified in FVIII

<400> SEQUENCE: 54

Gly Glu His Leu His Ala Gly Met Ser Thr Leu Phe Leu Val Tyr Ser
1               5                   10                  15
```

DE-IMMUNIZED FACTOR VIII MOLECULE AND PHARMACEUTICAL COMPOSITIONS COMPRISING THE SAME

This application contains a sequence listing filed in electronic form as an ASCII.txt file entitled "11573_WO_sequence listing.txt" created on Mar. 29, 2022, and having 234,645 bytes. The content of the sequence listing is incorporated herein in its entirety.

The present invention relates to the field of therapeutic proteins, in particular, to recombinant coagulation factors. It provides a recombinant Factor VIII (FVIII) protein comprising specific point mutations at defined positions, which serve to reduce the immunogenicity of said FVIII protein, wherein the Factor VIII protein substantially retains its coagulant activity. It further provides nucleic acids encoding said de-immunized protein, cell lines and methods of recombinant preparation as well as pharmaceutical compositions comprising the recombinant FVIII of the invention, which are advantageous for use in treatment of patients with Hemophilia A, particularly those who have not yet been treated with a FVIII product. Additionally, it can be a safe alternative for previously treated patients and even for patients who have developed an immune-response to FVIII, e.g., for immune-tolerance-induction therapy (ITI/ITT) or rescue ITI. The invention also provides an assay for determining immunogenicity of a protein.

FVIII is an important co-factor in the coagulation cascade. Wildtype human FVIII is synthesized as a single chain consisting of 2351 amino acids and comprises three A domains (A1-A3), one B domain and two C domains (C1 and C2), interrupted by short acidic sequences (a1-a3). The first 19 amino acids are the signal sequence, which is cleaved by intracellular proteases, leading to a FVIII molecule of 2332 amino acids. The resulting domain structure is A1-a1-A2-a2-B-a3-A3-C1-C2. During post-translational modification, FVIII becomes glycosylated, sulfated and proteolytically processed. The whole FVIII protein contains 25 potential N-glycosylation sites. Nineteen of these sites are located in the B domain and six further sites are spread along the rest of the protein. As not all of these sites become glycosylated, FVIII possesses only 21 N-glycosylations. Additionally, the B domain contains seven O-linked glycosylations. The glycosylation of FVIII plays a role in intracellular folding and transport. Sulfation is important for the extracellular interaction with different proteins, especially thrombin and von Willebrand factor (vWF). It takes place on six tyrosines in the acidic regions a1, a2 and a3. Intracellular cleavage, by the serine protease furin, divides FVIII into a heavy chain (A1-a1-A2-a2-B) and a light chain (a3-A3-C1-C2). During this cleavage, parts of the B domain can be lost. Therefore, the light chain has a molecular weight of 80 kDa, whereas the heavy chain can be slightly heterogeneous, with a molecular weight around 210 kDa. The binding between heavy and light chain is not covalent, but mediated by the divalent metal ion $Cu^{2+}$ between the A1 and A3 domain.

In the circulation, FVIII is bound to vWF via the a3, C1 and C2 domain, which protects FVIII from early activation as well as degradation.

Upon activation, FVIII is cleaved by thrombin at three positions, leading to a heterotrimer and loss of the B domain (heterotrimeric FVIIIa). The heterotrimer forms a complex with the activated coagulation Factor IXa and coagulation Factor X, and the light chain binds to a phospholipid bilayer, e.g., the cell membrane of (activated) platelets.

Hemophilia A mainly is a genetic bleeding disorder linked to the X-chromosome, occurring in 1 of 5000 newborn males. However, Hemophilia A can also occur spontaneously due to an auto-immune response against FVIII. Patients with Hemophilia A suffer from longer bleeding durations, spontaneous and internal bleedings, affecting their everyday life.

Hemophilia A patients are generally treated by administration of FVIII. Depending on the severity of the disease (mild, moderate or severe), treatment is on demand or prophylactic. Therapeutic FVIII products are either purified from human plasma (pFVIII) or the products are produced recombinantly in cell culture (rFVIII).

During the development of recombinant FVIII molecules for therapy, B-domain deleted FVIII molecules have been designed, because the B-domain is not important for the functionality of FVIII in clotting. This predominantly leads to a reduction in size. One of the most common B-domain deleted FVIII product is ReFacto® or ReFacto AF® produced by Pfizer. This FVIII variant lacks 894 amino acids of the B domain.

One issue with regard to FVIII substitution therapies is the relatively low in vivo half-life of the protein. Attempts to increase said half-life have been made, e.g., in WO 2015/023894 A1. The document provides recombinant FVIII proteins, in which one or more amino acids in at least one permissive loop or a3 domain are substituted or deleted, or replaced with heterologous moieties, while retaining the procoagulant FVIII activity. The generated FVIII proteins are supposed to have, e.g., increased in vivo stability.

Up to 30% of patients with severe Hemophilia A develop inhibitory anti-FVIII antibodies against therapeutic FVIII. This is due to the fact that the immune system of these patients recognizes the applied therapeutic FVIII as foreign, because the patients produce an altered endogenous FVIII variant, which can be mutated or truncated, or no FVIII at all. It is known that the inhibitory antibodies against FVIII have undergone class switching and affinity maturation. This hints towards a T cell-dependent activation of the B cells, which secrete the antibodies. This T cell-dependent B cell activation requires activated T helper cells, which derive from naive T helper cells through interaction with antigen presenting cells (APCs), which present the FVIII antigen and additional co-stimuli.

The fully human sequence of FVIII, which is administered as a therapeutic, could be considered a foreign protein by at least some hemophiliacs, because no central tolerance to the protein has developed. Depending on the HLA of the subject, the frequency of dosing and the location and nature of the mutations present in each subject's FVIII, immune responses to FVIII may be induced by treatment with FVIII. Those antibodies against FVIII, which interfere with the function of FVIII, are designated inhibitory antibodies or inhibitors. In the past, the development of FVIII inhibitors in subjects receiving FVIII therapy has been correlated with more severe mutations or non-expression of FVIII. It is expected that the more "foreign" the replacement therapy the more robust the resulting immune response. Indeed, in hemophiliacs, an anti-therapeutic immune response may be the normal and expected result of interaction between therapeutic FVIII and a healthy functioning immune system.

In the case of inhibitor formation, the patients mostly undergo an immune-tolerance-induction (ITI) therapy. During this therapy, which can take weeks, months or years, very high doses of FVIII are applied to the patients, in order to exhaust the immune system and, accordingly, to induce tolerance. This therapy is very cost-intensive as well as strenuous for the patients and their caregivers. During ITI, FVIII application occurs daily, in some cases even twice a day. In addition to the strenuous therapy, the number of bleeds are increased when inhibitors are present. The aim to protect the patient from disabilities resulting from joint bleeds impairs the social life of the patient as well as of the whole family. Furthermore, in a significant proportion of patients, ITI is not successful.

Recombinant porcine FVIII was approved by the FDA for the treatment of hemophilia A patients who have developed an autoimmune response to human FVIII. WO 99/46274 A1 discloses hybrid FVIII having human and animal FVIII sequences or human FVIII and non-FVIII sequences, including a modified factor VIII in which the amino acid sequence is changed by a substitution at one or more of specific loci, wherein the modified factor VIII is not inhibited by inhibitory antibodies against the A2 or C2 domain epitopes.

WO 2016/123200 A1 also describes recombinant or chimeric FVIII proteins wherein one or more protein domains comprise amino acid sequences that are derived from ancestrally reconstructed amino acid sequences, wherein the resulting FVIII shows reduced binding of inhibitors, i.e., wherein B cell epitopes have been deleted.

As T cells are believed to be involved in the generation of high affinity antibodies to FVIII, the development of recombinant FVIII molecules that do not contain common T cell epitopes and thus do not induce an immune response in patients has been suggested (Scott, 2014, Haemophilia 20 (01):80-86, Tangri et al., 2005, J Immunol. 174:3187-3196). Moise et al. (2012, Clin Immunol 142(3):329-331) published de-immunized FVIII peptides, wherein C2 domain T cell epitopes have been identified by in silico approaches, and modified. The modified peptides have been evaluated in an HLA binding assay and were used to immunize mice. Schubert et al. (2018, PLoS Comput Biol 14(3):e1005983) published a similar approach for population-specific design of de-immunized protein biotherapeutics, describing a computational approach for identifying mutations in the C2 domain of FVIII which lead to reduced immunogenicity whilst retaining pharmaceutical activity and protein function. For example, they teach de-immunization results for sequences with up to three simultaneous point mutations (e.g., V2333E, L2321F, Q2335H or V2313M/V2313T). As an experimental validation of the in silico calculations, they measure affinity of 15mer peptides to specific HLA alleles.

WO 2011/060371 A2 discloses a modified FVIII polypeptide comprising at least one amino acid modification within a specific region of the C2 domain of FVIII believed to form a B cell epitope for an inhibitor, and/or at least one amino acid modification within a specific region of the A2 domain of FVIII believed to form a relevant T cell epitope, for preventing or reducing an initial immune response to factor VIII in patients suffering from hemophilia A or for reducing the intensity of an immune response in patients having pre-formed inhibitor antibodies against factor VIII.

In light of the state of the art, the present inventors addressed the problem of providing a de-immunized recombinant FVIII protein, i.e., a protein with a reduced number of T cell epitopes relevant for a significant proportion of humans, wherein the FVIII has a coagulant activity. Advantageously, use of this FVIII protein for therapy of Hemophilia A patients prevents or reduces the generation of anti-FVIII antibodies including FVIII inhibitory antibodies.

SUMMARY OF THE INVENTION

The invention provides, as a first embodiment, a recombinant Factor VIII protein comprising at least three amino acid substitutions at positions selected from the group consisting of Y748, L171, S507, N79, I80, I105, S112, L160, V184, N233, L235, V257, I265, N299, Y426, Y430, L505, F555, I610, N616, I632, L706, N754, K1837, R1936, S2030, S2037, N2038, S2077, M2123, S2125, F2215, K2226, K2258, V2313, S2315, V2333 and Q2335;

wherein substitutions of N are independently selected from the group consisting of D, H, S and E; wherein substitution of I are independently selected from the group consisting of T and V; wherein substitutions of S are independently selected from the group consisting of A, N, G, T and E; wherein substitutions of L are independently selected from the group consisting of N, Q, F and S; wherein substitutions of V are independently selected from the group consisting of A and T; wherein substitutions of Y are independently selected from the group consisting of N, H and S; wherein substitutions of F are independently selected from the group consisting of H and S; wherein substitutions of K are independently selected from the group consisting of N, D, E, Q, S and T; wherein substitutions of R are independently selected from the group consisting of Q, H and S; wherein substitutions of M are selected from the group consisting of R, Q, K and T; and/or wherein substitutions of Q are selected from the group consisting of R, D, E, H and K;

wherein the positions are specified in relation to full length human Factor VIII molecule of SEQ ID NO: 1;

and wherein the recombinant Factor VIII protein retains at least 50% coagulant activity, as determined in a chromogenic assay, compared to a Factor VIII protein consisting of SEQ ID NO: 2, or a fusion protein of said recombinant Factor VIII protein.

The invention provides, as a second embodiment, a recombinant Factor VIII protein comprising at least one amino acid substitution at a position selected from the group consisting of Y748, L171, S507, N79, I80, I105, S112, L160, V184, N233, L235, V257, I265, N299, Y426, Y430, L505, F555, 1610, N616, I632, L706, N754, K1837, R1936, S2030, S2037, N2038, S2077, M2123, S2125, F2215, K2226, K2258, V2313, S2315, V2333 and Q2335;

wherein substitutions of N are independently selected from the group consisting of D, H, S and E; wherein substitution of I are independently selected from the group consisting of T and V; wherein substitutions of S are independently selected from the group consisting of A, N, G, T and E; wherein substitutions of L are independently selected from the group consisting of N, Q, F and S; wherein substitutions of V are independently selected from the group consisting of A and T; wherein substitutions of Y are independently selected from the group consisting of N, H and S; wherein substitutions of F are independently selected from the group consisting of H and S; wherein substitutions of K are independently selected from the group consisting of N, D, E, Q, S and T; wherein substitutions of R are independently selected from the group consisting of Q, H and S; wherein substitutions of M are selected from the group consisting of R, Q, K and T; and/or wherein substitutions of Q are selected from the group consisting of R, D, E, H and K;

wherein, if the mutation is at position S507, it is S507E, and if the mutation is at position N616, it is N616E, and if the mutation is at position F2215, it is F2215H;

wherein the positions are specified in relation to full length human Factor VIII molecule of SEQ ID NO: 1, and wherein the recombinant Factor VIII protein retains at least 50% coagulant activity, as determined in a chromogenic assay, compared to a Factor VIII protein consisting of SEQ ID NO: 2, or a fusion protein of said recombinant Factor VIII protein. Said protein optionally is a protein of embodiment 1.

In a third embodiment, the recombinant Factor VIII protein of any of the preceding embodiments may e.g. comprise amino acid substitutions selected from the group consisting of Y748S, L171Q, S507E, N79S, 180T, 1105V, S112T, L160S, V184A, N233D, L235F, V257A, I265T, N299D, Y426H, Y430H, L505N, F555H, I610T, N616E, I632T, L706N, N754D, K1837E, R1936Q, S2030A, S2037G, N2038D, S2077G, M2123K, S2125G, F2215H, K2226Q, K2258Q, V2313A, S2315T, V2333A and Q2335H.

In a fourth embodiment, the recombinant Factor VIII protein of any of the preceding embodiments may e.g. comprise 3-25 of said substitutions and the substitutions may be located within different immunogenic clusters.

In a fifth embodiment, the recombinant Factor VIII protein of any of the preceding embodiments may e.g. comprise at least three amino acid substitutions at positions selected from the group consisting of Y748, L171, S507, N79, S112, L160, V184, N233, I265, N299, Y426, F555, N616, I632, L706, K1837, R1936, N2038, S2077, S2125, F2215, K2226, K2258, S2315, and V2333;

wherein the at least three amino acid substitutions are preferably selected from the group consisting of Y748S, L171Q, S507E, N79S, S112T, L160S, V184A, N233D, I265T, N299D, Y426H, F555H, N616E, 1632T, L706N, K1837E, R1936Q, N2038D, S2077G, S2125G, F2215H, K2226Q, K2258Q, S2315T and V2333A.

In a 6$^{th}$ embodiment, the recombinant Factor VIII protein of any of the preceding embodiments may e.g. comprise amino acid substitutions at least at positions a. N79S, S112T, N233D, and I265T; and/or
b. N79S, S112T, L160S, L171Q, V184A, N233D, and I265T; and/or
c. N299D, Y426H, and S507E; and/or
d. F555H, N616E, L706N, Y748S; and/or
e. F555H, N616E, I632T, L706N, and Y748S; and/or
f. S2077G, S2315T, and V2333A; and/or
g. N2038D, S2077G, S2315T, and V2333A; and/or
h. S2077G, K2258Q, S2315T, and V2333A; and/or
i. N2038D, S2077G, K2258Q, S2315T, and V2333A; and/or
j. N2038D, S2077G, S2125G, K2258Q, S2315T, and V2333A; and/or
k. L171Q, S507E, Y748S and V2333A; and/or
l. L171Q, N299D, N616E and V2333A; and/or
m. S112T, S507E, Y748S, K1837E and N2038D; and/or
n. S112T, Y426H, N754D, K1837E and N2038D preferably, combining at least the substitutions specified under b and c, optionally further including substitutions selected from those specified under d or e and/or f, g, h, I or j and/or K1837E.

In a 7$^{th}$ embodiment, the recombinant Factor VIII protein of any of the preceding embodiments may e.g. comprise at least amino acid substitutions at positions N79, S112, L160, L171, V184, N233, I265, N299, Y426, S507, F555, N616, L706, and Y748, wherein preferably the substitutions are N79S, S112T, L160S, L171Q, V184A, N233D, I265T, N299D, Y426H, S507E, F555H, N616E, L706N, and Y748S, wherein optionally, the protein further includes K1837E and comprises the amino acid sequence according to aa 20-1533 of SEQ ID NO: 7.

In an 8$^{th}$ embodiment, the recombinant Factor VIII protein of any of the preceding embodiments may e.g. comprise at least amino acid substitutions at positions N79, S112, L160, L171, V184, N233, I265, N299, Y426, S507, F555, N616, L706, Y748, N2038, S2077, S2315 and V2333, wherein preferably the 18 substitutions are N79S, S112T, L160S, L171Q, V184A, N233D, I265T, N299D, Y426H, S507E, F555H, N616E, L706N, Y748S, N2038D, S2077G, S2315T and V2333A, wherein optionally, the protein comprises the amino acid sequence according to aa 20-1533 of SEQ ID NO: 6.

In a 9$^{th}$ embodiment, the recombinant Factor VIII protein of any of the preceding embodiments may e.g. comprise at least the amino acid substitution at position K1837, wherein preferably said substitution is K1837E, wherein, optionally, the protein comprises the amino acid sequence according to aa 20-1533 of SEQ ID NO: 5.

In a 10$^{th}$ embodiment, the recombinant Factor VIII protein of any of the preceding embodiments may e.g. have a reduced immunogenicity compared to a Factor VIII protein consisting of SEQ ID NO: 2 and preferably also compared to a Factor VIII protein consisting of SEQ ID NO: 3, wherein said immunogenicity is optionally determined by an immunogenicity score or an assay comprising co-cultivating dendritic cells incubated with said protein and regulatory T-cell-depleted $CD4^+$ T cells of a donor and testing activation of said T cells, preferably, by said assay.

In an 11$^{th}$ embodiment, the recombinant Factor VIII protein of any of the preceding embodiments may e.g. have at least 90% sequence identity to a Factor VIII protein of SEQ ID NO: 5, wherein only the A1, a1, A2, a2, a3, A3, C1 and C2 domains are considered for determination of sequence identity, or it may be a fusion protein of said recombinant Factor VIII protein.

In a 12$^{th}$ embodiment, the recombinant Factor VIII protein of any of the preceding embodiments may e.g. be a single chain Factor VIII protein or a heterodimeric Factor VIII protein, preferably, a single chain B-domain deleted Factor VIII protein.

In a 13$^{th}$ embodiment, the recombinant Factor VIII protein of any of the preceding embodiments may e.g. be a fusion protein, wherein the fusion partner is selected from the group comprising an Fc region, albumin, an albumin binding sequence, PAS polypeptides, HAP polypeptides, the C-terminal peptide of the beta subunit of chorionic gonadotropin, albumin-binding small molecules, polyethylenglycol, hydroxyethyl starch, and combinations thereof.

In a 14$^{th}$ embodiment, the invention also provides a nucleic acid encoding the recombinant Factor VIII protein of any of the preceding embodiments, wherein the nucleic acid preferably is an expression vector suitable for expression of said recombinant Factor VIII protein in a mammalian cell selected from the group comprising a human cell.

In a 15$^{th}$ embodiment, the invention also provides a host cell comprising said nucleic acid of the 14$^{th}$ embodiment, wherein the host cell preferably is a mammalian cell comprising an expression vector suitable for expression of said recombinant Factor VIII protein in said cell.

In a 16$^{th}$ embodiment, the invention also provides a pharmaceutical composition comprising the recombinant Factor VIII protein of any of embodiments 1-13, the nucleic acid of embodiment 14 or the host cell of embodiment 15.

In a 17$^{th}$ embodiment, the pharmaceutical composition of the 16$^{th}$ embodiment further comprises an immunosuppressive agent selected from the group comprising methylprednisolone, prednisolone, cyclophosphamide, rituximab, and/or cyclosporin.

In an 18th embodiment, the pharmaceutical composition of the 16th or 17th embodiment is for use in treating a patient with Hemophilia A selected from the group comprising a patient not previously treated with any Factor VIII protein, a patient previously treated with a Factor VIII protein, a patient who has an antibody response including an inhibitory antibody response to a Factor VIII protein, and a patient who has had an antibody response including an inhibitory antibody response to a Factor VIII protein who has been treated by ITI.

The invention also provides a method for treating a patient in need thereof, e.g., a patient with Hemophilia A selected from the group comprising a patient not previously treated with any Factor VIII protein, a patient previously treated with a Factor VIII protein, a patient who has an antibody response including an inhibitory antibody response to a Factor VIII protein, and a patient who has had an antibody response including an inhibitory antibody response to a Factor VIII protein who has been treated by ITI with an effective amount of the pharmaceutical composition of any of embodiments 16 or 17.

In a 19th embodiment, the invention also provides an in vitro method for preparing a Factor VIII protein of any of embodiments 1-13, comprising culturing a host cell of embodiment 15 expressing said FVIII protein under suitable conditions and isolating said FVIII protein.

In a 20th embodiment, the invention also provides an in vitro method of embodiment 19 for preparing a Factor VIII protein having reduced immunogenicity, the method comprising a) analyzing a FVIII protein for the presence of T-cell epitopes relevant for a significant proportion of humans;
b) preparing a plurality of mutants of said protein comprising at least one, preferably only one, amino acid substitution in a position that eliminates one of the T cell epitopes identified in step a, and analyzing coagulant activity of said mutants;
c) preparing a plurality of mutants of said protein each comprising at least three of the substitutions identified in step b as leading to a protein having at least 50% of the coagulant activity of a Factor VIII protein of SEQ ID NO: 2 or of a FVIII protein having 80-120%, preferably 90-110%, of the coagulant activity of the Factor VIII protein of SEQ ID NO: 2, wherein the substitutions are located within different immunogenic clusters, and wherein each of said mutants comprises all substitutions identified in a contiguous region of said protein, and analyzing coagulant activity of said mutants;
d) if any of the mutants of step c have a coagulant activity of less than 50% of the coagulant activity of a Factor VIII protein of SEQ ID NO: 2 or of a FVIII protein having 80-120%, preferably 90-110%, of the coagulant activity of the Factor VIII protein of SEQ ID NO: 2, repeating preparing a plurality of mutants of said protein each comprising at least three of the substitutions identified in step b as leading to a protein having at least 50% of the coagulant activity of a Factor VIII protein of SEQ ID NO: 2 or of a FVIII protein having 80-120%, preferably 90-110%, of the coagulant activity of the Factor VIII protein of SEQ ID NO: 2, wherein the substitutions are located within different immunogenic clusters, and wherein different combinations of substitutions identified in said contiguous region of said protein are prepared, and analyzing coagulant activity of said mutants;
e) preparing a Factor VIII protein comprising at least three, preferably, at least 10 substitutions found not to reduce coagulant activity of said protein to less than 50% of the coagulant activity of a Factor VIII protein of SEQ ID NO: 2 or of a FVIII protein having 80-120%, preferably 90-110%, of the coagulant activity of the Factor VIII protein of SEQ ID NO: 2 in combination with other substitutions included; and optionally
f) formulating said protein as a pharmaceutical composition, wherein preferably, the coagulant activity is at least 80% of the coagulant activity of a Factor VIII protein of SEQ ID NO: 2 or of a FVIII protein having 80-120%, preferably 90-110%, of the coagulant activity of the Factor VIII protein of SEQ ID NO: 2.

In a 21st embodiment, the invention also provides an in vitro method for analyzing the immunogenicity of a protein, comprising co-cultivating dendritic cells incubated with said protein and regulatory T-cell-depleted $CD4^+$ T cells of a donor and testing activation of said T cells, wherein the protein preferably is a recombinant Factor VIII protein of any of embodiments 1-13.

LEGENDS

FIG. 1: (A) Structure of FVIII protein and generation of the FVIII-19M protein of the invention in several rounds of selection. (B) FVIII-19M amino acid sequence (SEQ ID NO:5) including the signal sequence. Signal sequence: italics, A1 domain: underline, A2 domain: double underline, B domain: fat underline, A3 domain: dotted underline, C1 domain: dashed underline, C2 domain: wavy underline, intermediate domains a1, a2, a3: not marked, mutations versus FVIII-6rs are marked by italics, fat and larger type.

FIG. 2: Relative coagulant activities of FVIII variants with single mutations. The FVIII coagulant activity of each single-mutation variant was calculated in relation to the FVIII coagulant activity of the control FVIII-6rs. The brackets indicate mutations, which belong to one cluster. (A) Mutations in the A1 domain. (B) Mutations in the A2 domain. (C) Mutations in the A3 domain. (D) Mutations in the C1 domain. (E) Mutations in the C2 domain.

Figure 3:
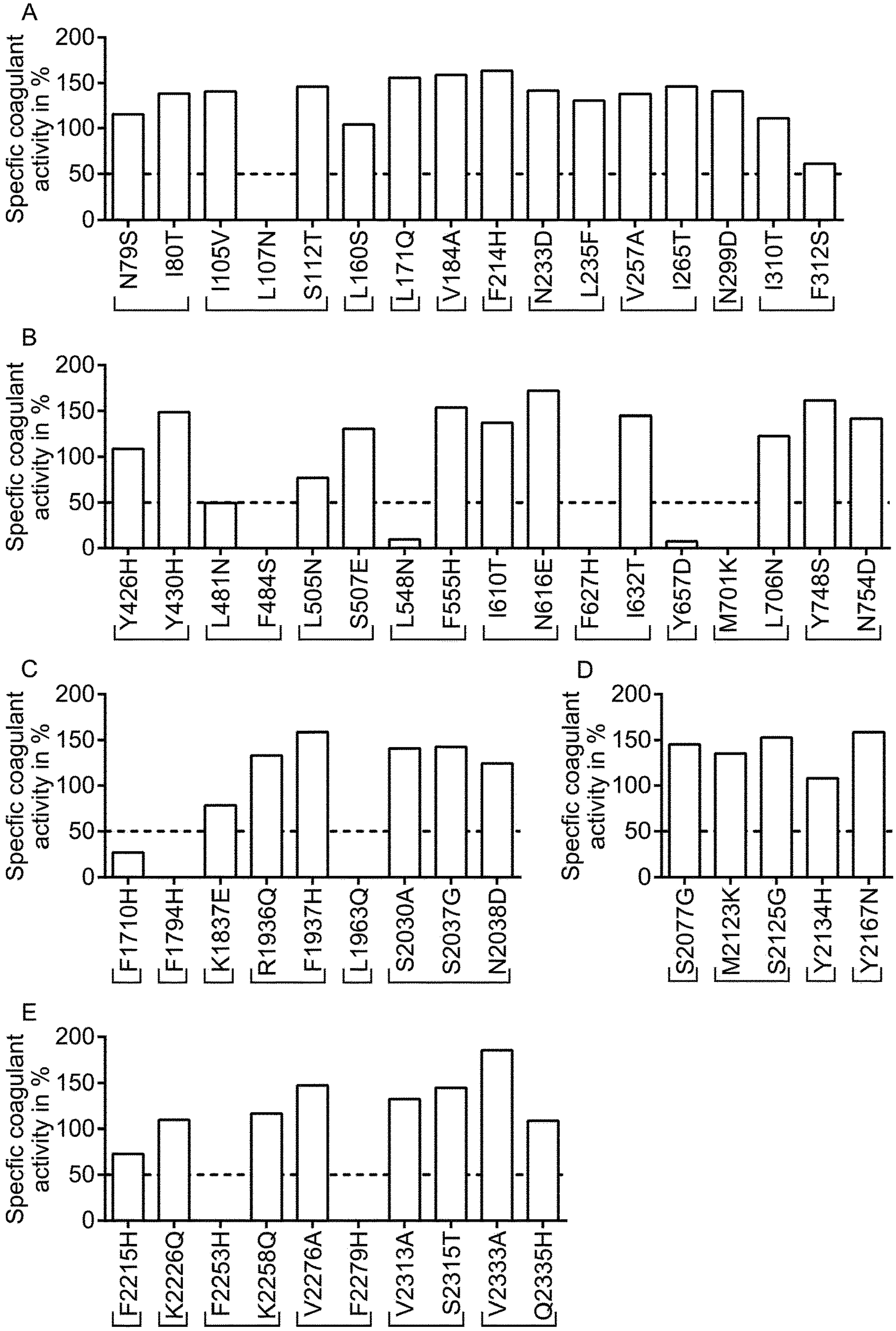

FIG. 3: Specific coagulant activities of FVIII variants with single mutations. The relation of FVIII coagulant activity to FVIII antigen was calculated for each single-mutation variant. The brackets indicate mutations, which belong to one cluster. (A) Mutations in the A1 domain. (B) Mutations in the A2 domain. (C) Mutations in the A3 domain. (D) Mutations in the C1 domain. (E) Mutations in the C2 domain.

FIG. 4: Results of the combined mutations in section A1, A1A2, A2 and A3C1C2. (A) Relative coagulant activities of the FVIII variants. The FVIII coagulant activity of each variant was calculated in relation to the FVIII coagulant activity of the control FVIII-6rs. (B) Specific coagulant activities of the FVIII variants. The relation of FVIII coagulant activity to FVIII antigen was calculated for each variant.

FIG. 5: Relative coagulant activities of FVIII variants comprising different mutations based on a DOE matrix. The FVIII coagulant activity of each variant was calculated in relation to the FVIII coagulant activity of the control FVIII-6rs. (A) Results for the variants in the A2 domain. (B) Results for the variants in the A3C1C2 domain.

Figure 6A:
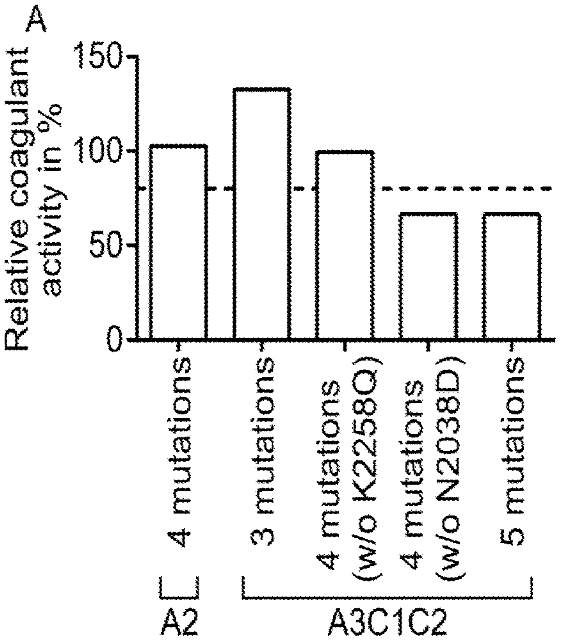
Figure 6B:
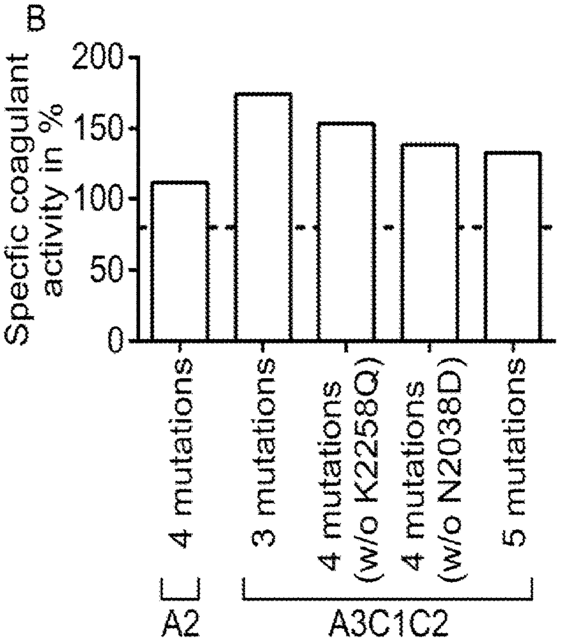

FIG. 6: Coagulant activities of FVIII with combined mutations in the sections A2 and A3C1C2 after the DOE matrix. (A) Relative coagulant activities of the FVIII variants. The FVIII coagulant activity of each variant was calculated in relation to the FVIII coagulant activity of the control FVIII-6rs. (B) Specific coagulant activities of the FVIII variants. The ratio of chromogenic FVIII coagulant activity to FVIII antigen was calculated for each variant.

FIG. 7: Relative and specific coagulant activities of FVIII variants with specific mutations (A, B). Relative coagulant activities are defined in comparison to coagulant activity of FVIII-6rs. Specific coagulant activity relates to the ratio of chromogenic coagulant activity to antigen. Coagulant activities of advantageous FVIII proteins having mutations in specific domains of FVIII (A) and FVIII proteins having three mutations (B). Clotting coagulant activity of FVIII-BA3-1M was not determined.

Figures 7B, 8:
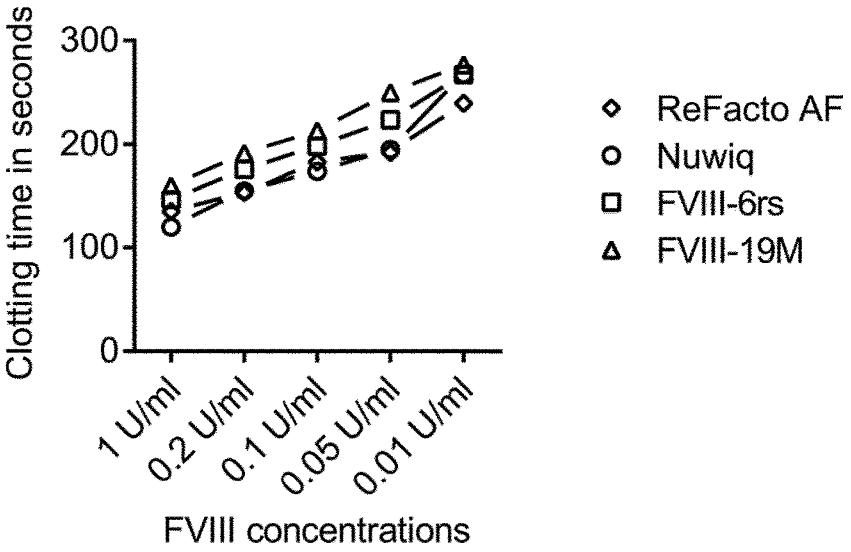

FIG. 8: ROTEM analysis of FVIII-19M, FVIII-6rs, ReFacto AF® and NUWIQ® analyzing clotting time. Different FVIII concentrations were analyzed. The measurements were performed in duplicates and the mean values are displayed.

Figure 9:
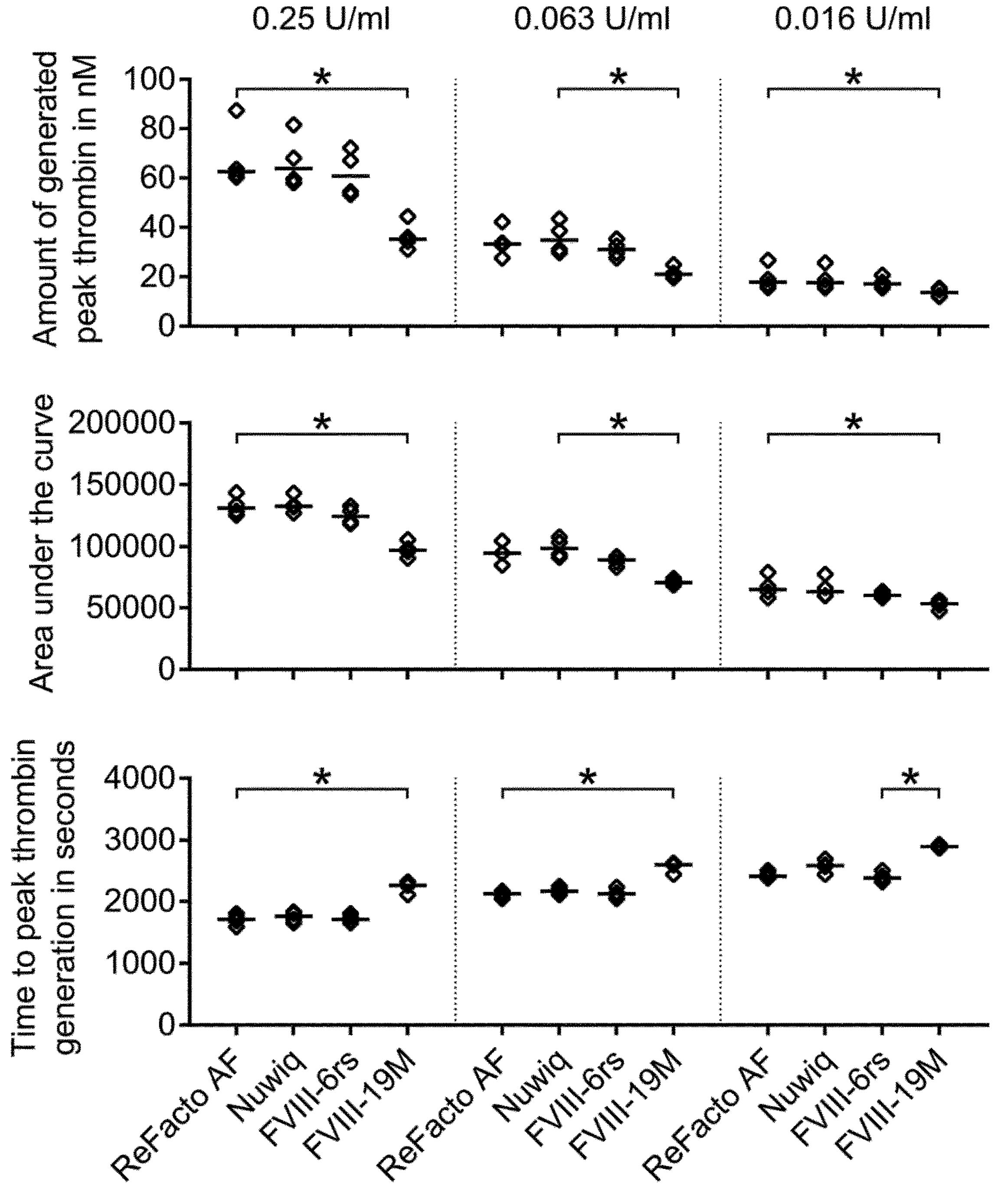

FIG. 9: Results of the TGA (Thrombin generation assay) for ReFacto AF®, NUWIQ®, FVIII-19M and FVIII-6rs. All products were diluted to 0.25 U/ml, 0.063 U/ml and 0.016 U/ml FVIII coagulant activity. Each point indicates the results from one TGA. The line indicates the median of the four performed assays. Statistical analysis was performed using the Friedman test. (A) Amount of generated peak thrombin for each product at the given concentration based on a thrombin standard. (B) Area under the curve for each product at the given concentration. (C) Time to peak thrombin generation for each product at the given concentration.

Figure 10:
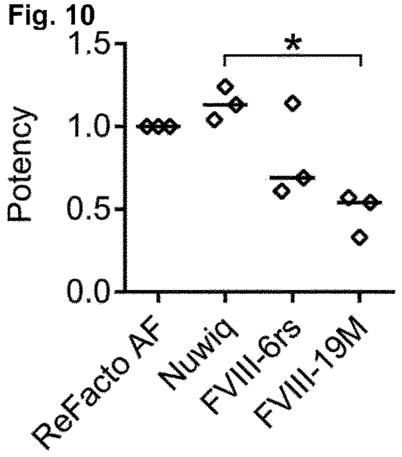

FIG. 10: Binding of the different FVIII products to vWF. The potency of ReFacto AF® binding to vWF was set to 1 and was the reference for the other products. Each point indicates the results from one ELISA. The line indicates the median of the three performed assays. Statistical analysis was performed using the Friedman test.

Figure 11:
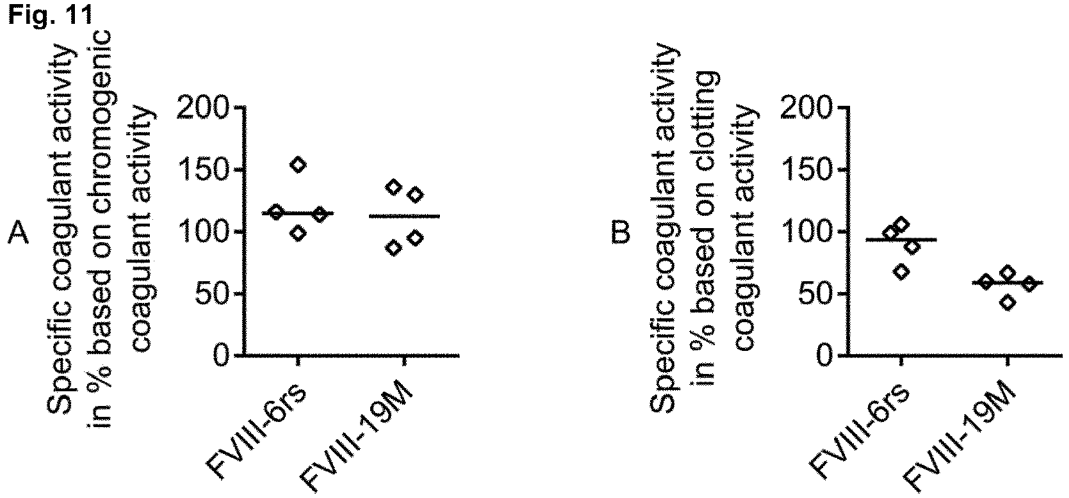

FIG. 11: Specific coagulant activities of four independent productions of FVIII-6rs and FVIII-19M based on purified protein. (A) Specific coagulant activities based on the chromogenic FVIII coagulant activity measurement. The line indicates the median of the four measurements. (B) Specific coagulant activities based on the clotting FVIII coagulant activity measurement. The line indicates the median of the four measurements.

Figure 12:
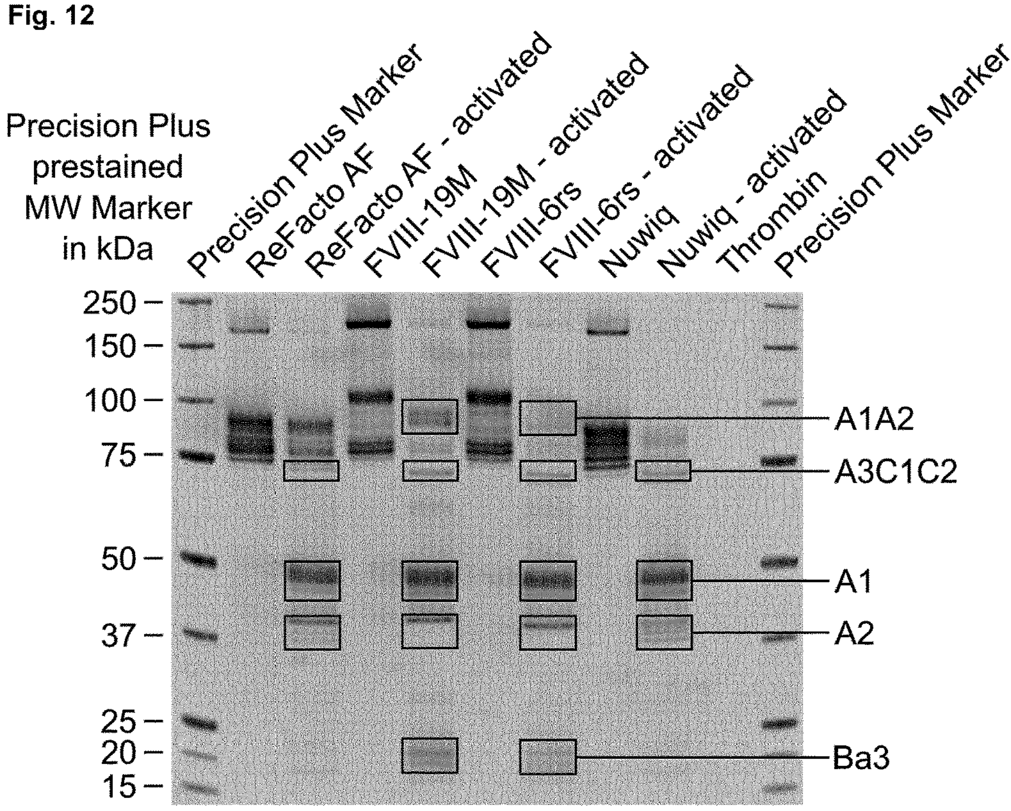

FIG. 12: Western Blot of FVIII activated by thrombin. Each product was applied in its non-activated and activated form. In the non-activated form, the typical bands for the single chain (≈200 kDa), heavy chain (≈95-110 kDa) and light chain (≈80-90 kDa) were detectable. After thrombin cleavage additional bands for A1A2 (≈90 kDa), A3C1C2 (≈75 kDa), A1 (≈50 kDa), A2 (≈40 kDa) and Ba3 (≈20 kDa) were detectable. FVIII was detected with the primary polyclonal sheep anti-human Factor VIII antibody and the secondary donkey anti-sheep IgG IRDye 800CW.

Figure 13:
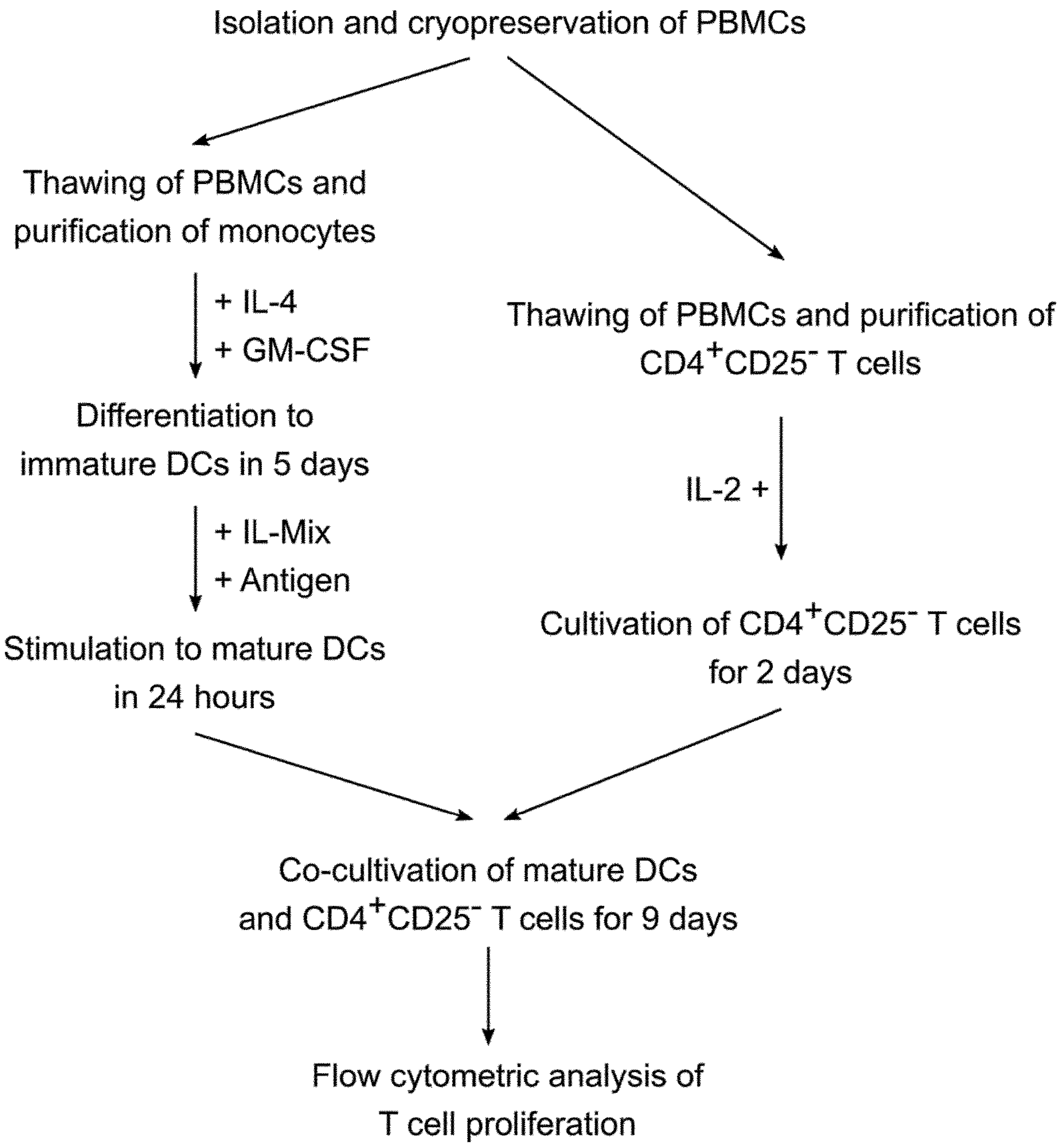

FIG. 13: In vitro immunogenicity assay. Monocytes are purified from PBMCs, differentiated to iDCs and finally stimulated to become mDCs and incubated with the antigen, i.e., the protein of interest. CD4+CD25-T cells are also purified from PBMCs and cultivated prior to co-cultivation, in order to regenerate. After co-culture, the T cells are analyzed for activation and/or proliferation by flow cytometry. Optionally, the supernatant is analyzed for cytokines.

Figure 14:
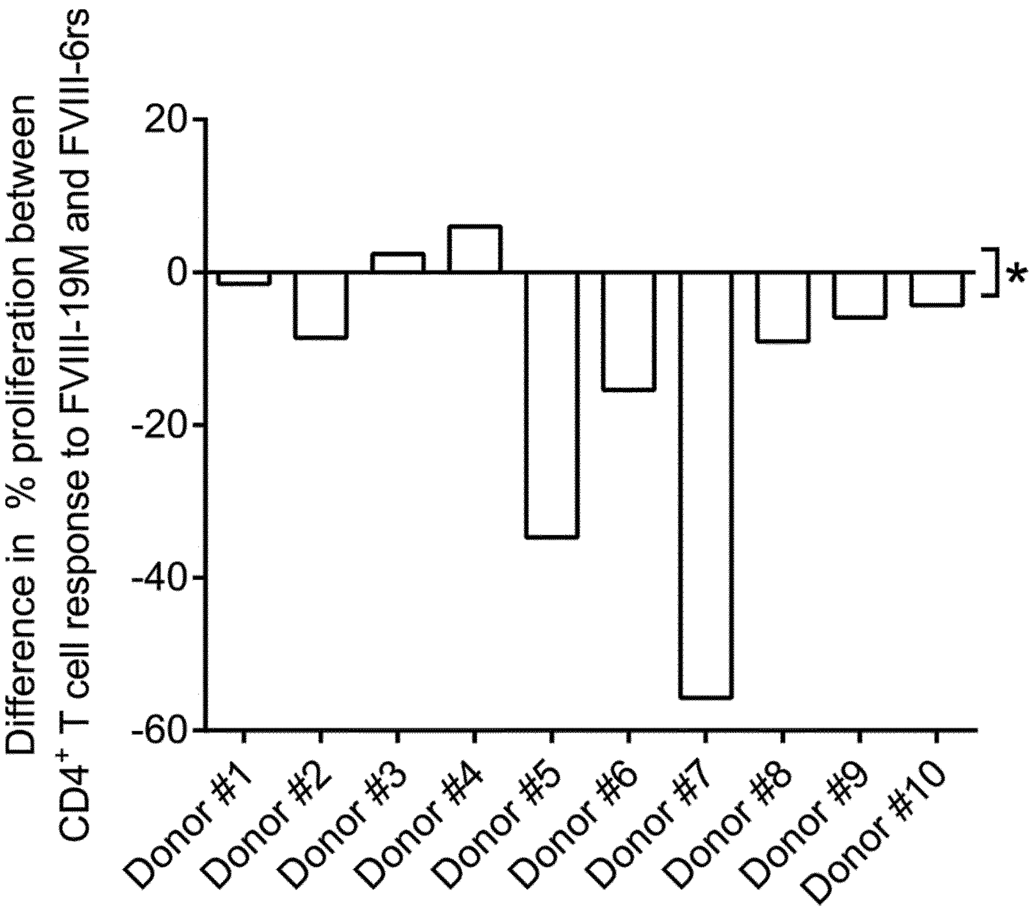

FIG. 14: Results of the in vitro immunogenicity assay. Difference between the $CD4^+$ T cell proliferation against DCs stimulated with IL-Mix plus FVIII-19M and DCs stimulated with IL-Mix plus FVIII-6rs. The bars below 0 indicate a reduced CD4+ T cell response to FVIII-19M. The lower T cell response to FVIII-19M compared to FVIII-6rs is significant using the Wilcoxon test (p=0.0371).

SEQUENCE LISTING

Sequences of the following FVIII proteins, including preferred signal sequences are provided in the sequence listing.

SEQ ID NO: 1 wt human FVIII
SEQ ID NO: 2 FVIII-6rs
SEQ ID NO: 3 ReFacto AF®
SEQ ID NO: 4 B-domain deleted scFVIII
SEQ ID NO: 5 FVIII-19M
SEQ ID NO: 6 FVIII-18M
SEQ ID NO: 7 FVIII-15M
SEQ ID NO: 8 FVIII-A1-7M
SEQ ID NO: 9 FVIII-A2-4M
SEQ ID NO: 10 FVIII-BA3-1M
SEQ ID NO: 11 FVIII-A3C2-4M
SEQ ID NO: 12 FVIII-GOF1
SEQ ID NO: 13 FVIII-GOF2
SEQ ID NO: 14 FVIII-LS1
SEQ ID NO: 15 FVIII-LS2
SEQ ID NO: 51 FVIII-A1A2-3M
SEQ ID NO: 52 provides a nucleic acid sequence encoding FVIII-19M.
SEQ ID NO: 53 provides a nucleic acid sequence encoding FVIII-6rs.

DETAILED DESCRIPTION OF THE INVENTION

The present invention provides a recombinant Factor VIII protein comprising at least three amino acid substitutions at positions selected from the group consisting of Y748, L171, S507, N79, I80, I105, S112, L160, V184, N233, L235, V257, I265, N299, Y426, Y430, L505, F555,I610, N616, I632, L706, N754, K1837, R1936, S2030, S2037, N2038, S2077, M2123, S2125, F2215, K2226, K2258, V2313, S2315, V2333 and Q2335;

wherein substitutions of N are independently selected from the group consisting of D, H, S and E; wherein substitution of I are independently selected from the group consisting of T and V; wherein substitutions of S are independently selected from the group consisting of A, N, G, T and E; wherein substitutions of L are independently selected from the group consisting of N, Q, F and S; wherein substitutions of V are independently selected from the group consisting of A and T; wherein substitutions of Y are independently selected from the group consisting of N, H and S; wherein substitutions of F are independently selected from the group consisting of H and S; wherein substitutions of K are independently selected from the group consisting of N, D, E, Q, S and T; wherein substitutions of R are independently selected from the group consisting of Q, H and S; wherein substitutions of M are selected from the group consisting of R, Q, K and T; and/or wherein substitutions of Q are selected from the group consisting of R, D, E, H and K;

wherein the positions are specified in relation to full length human Factor VIII molecule of SEQ ID NO: 1 including numbering of the signal sequence;

and wherein the recombinant Factor VIII protein retains at least 50% coagulant activity, as determined in a chromogenic assay, compared to a Factor VIII protein consisting of SEQ ID NO: 2 (FVIII-6rs).

The invention also provides a fusion protein of said recombinant Factor VIII protein.

The present invention further provides a recombinant Factor VIII protein comprising at least one amino acid substitution at a position selected from the group consisting of Y748, L171, S507, N79, I80, I105, S112, L160, V184, N233, L235, V257, I265, N299, Y426, Y430, L505, F555, I610, N616, I632, L706, N754, K1837, R1936, S2030, S2037, N2038, S2077, M2123, S2125, F2215, K2226, K2258, V2313, S2315, V2333 and Q2335;

- wherein substitutions of N are independently selected from the group consisting of D, H, S and E; wherein substitution of I are independently selected from the group consisting of T and V; wherein substitutions of S are independently selected from the group consisting of A, N, G, T and E; wherein substitutions of L are independently selected from the group consisting of N, Q, F and S; wherein substitutions of V are independently selected from the group consisting of A and T; wherein substitutions of Y are independently selected from the group consisting of N, H and S; wherein substitutions of F are independently selected from the group consisting of H and S; wherein substitutions of K are independently selected from the group consisting of N, D, E, Q, S and T; wherein substitutions of R are independently selected from the group consisting of Q, H and S; wherein substitutions of M are selected from the group consisting of R, Q, K and T; and/or wherein substitutions of Q are selected from the group consisting of R, D, E, H and K;
- wherein, if the substitution is at position S507, it is S507E, and if the substitution is at position N616, it is N616E, and if the substitution is at position F2215, it is F2215H;
- wherein the positions are specified in relation to full length human Factor VIII molecule of SEQ ID NO: 1 including numbering of the signal sequence,
- and wherein the recombinant Factor VIII protein retains at least 50% coagulant activity, as determined in a chromogenic assay, compared to a Factor VIII protein consisting of SEQ ID NO: 2 (FVIII-6rs),
- or a fusion protein of said recombinant Factor VIII protein. Said protein preferably also is a protein comprising at least three of the substitutions defined above.

Preferably, if the substitution is at position K2226, it is K2226Q, and if the substitution is at position Q2335, it is Q2335H. In one embodiment, there is no substitution of Q2335.

The inventors have found that a recombinant Factor VIII protein of the invention, as defined herein, has a significantly reduced immunogenicity while substantially maintaining coagulant activity. Accordingly, it is useful for treatment of hemophilia A, in particular, to avoid generation and/or further production of anti-FVIII antibodies including FVIII inhibitory antibodies.

The FVIII protein of the invention has been de-immunized on the level of T cell epitopes. Generally, antigens are presented to T cells as peptides bound to the MHC class II on the surface of APCs. As T cell epitopes relevant for the majority of the human population have been identified and eliminated in the protein of the invention, fewer immunogenic peptides will be presented by antigen-presenting cells (APCs), e.g., dendritic cells (DC) or B cells, to the T cells. This in turn prevents or reduces the activation of naive T cells. Without activated T helper cells, naive B cells are not activated and cannot differentiate into anti-FVIII antibody-secreting plasma and memory B cells.

By the approach of the present invention, the antibody formation is thus reduced or, optimally, prevented at the very beginning of the process, namely by reducing the stimulation of naive T helper cells in response to FVIII antigens. In addition to the reduction of naive T helper cell maturation, re-stimulation of memory T helper cells against FVIII, which are potentially already present, may also be prevented or reduced due to reduced presentation of the antigen according to the inventive approach.

The positions in the MHC class II binding groove required for peptide binding as well as the amino acids of the peptide important for the binding are known. As a first step, in silico analysis methods have been used to predict which FVIII peptides are most likely bound in common MHC class II complexes, and which of these only occur in FVIII, and not in other human proteins. These peptides are considered as immunogenic. Using further in silico tools and comparisons with both FVIII from other species and non-related human proteins, recommendations for amino acid mutations have been made to prevent FVIII peptide binding to MHC class II complex. Based on these predictions and experimental tests, mutated FVIII variants have been generated, which are still functional in coagulation, but are considered to no longer elicit the generation of inhibitory antibodies in hemophilia A patients to the same extent.

The FVIII proteins of the invention have at least 50% coagulant activity, as determined in a chromogenic assay, compared to a Factor VIII protein consisting of SEQ ID NO: 2 (FVIII-6rs). FVIII-6rs is a B-domain deleted FVIII protein containing no further mutations, which has substantially the same coagulant activity as wildtype human FVIII. Preferably, the FVIII proteins of the invention have at least 70%, at least 80%, at least 90%, or at least 100% coagulant activity compared to a Factor VIII protein consisting of SEQ ID NO: 2. The coagulant activity may also be higher, e.g., at least 110%, at least 120%, at least 130%, at least 140%, at least 150%, at least 190%, at least 200% or at least 400% of coagulant activity compared to a Factor VIII protein consisting of SEQ ID NO: 2.

Throughout the invention, if not specified otherwise, coagulant activity is determined in a chromogenic assay. The chromogenic assay is carried out according to standard procedures, e.g., as described in detail in the examples below. This assay is preferably carried out with the supernatant of human cells, e.g., HEK293-F cells, transfected with an expression vector, e.g., as described in the examples, and expressing the FVIII variant of interest, in comparison to supernatant of the same cells transfected with the same basic expression vector expressing FVIII-6rs under the same conditions. Accordingly, relative coagulant activities can be analyzed, wherein the chromogenic coagulant activities of the mutants are standardized to the chromogenic coagulant activities of the molecule without mutations, namely FVIII-6rs. This assay tests both the capability of the mutant protein to be synthesized and secreted by the cells and the coagulant activity of the secreted protein.

In addition, the FVIII of the invention preferably further has a high specific coagulant activity. The specific coagulant activity describes the ratio of FVIII chromogenic coagulant activity as defined above to FVIII antigen concentration, as determined by an FVIII-specific ELISA (e.g., as described herein). The specific coagulant activity of a FVIII protein of the invention may be, e.g., at least 50%, at least 70%, at least 80%, at least 90%, at least 100%, at least 110%, at least 120%, at least 130%, at least 150%, at least 170% or at least 190%.

Proteins having a low relative coagulant activity in the supernatant, but a high specific coagulant activity can be assumed to have problems with synthesis, folding and/or secretion. This can potentially be improved by expression in specific cells lines, e.g., with overexpression of chaperones.

Factor VIII proteins of the invention may have both a coagulant activity and a specific coagulant activity (both determined by the chromogenic method) of at least 50% compared to FVIII-6rs, preferably, of at least at least 70%, at least 80%, at least 90%, at least 100%, at least 110%, at least 120%, or at least 130%, respectively.

Coagulant activity can alternatively or additionally be assessed by the one stage clotting method, as also described in the experimental part herein. In a particularly preferred embodiment, both the coagulant activity as determined by the chromogenic method and as determined by the clotting method are at least 50% compared to the coagulant activity of FVIII-6rs, preferably, at least 60%, at least 70%, at least 80%, at least 90%, at least 100%, or even at least 150%.

The inventors found that specific substitutions tested were particularly advantageous with regard both to a reduced immunogenicity and maintenance of functional activity in coagulation. Accordingly, throughout the invention, the amino acid substitutions in the recombinant Factor VIII protein of the invention are preferably selected from the group consisting of Y748S, L171Q, S507E, N79S, 180T, 1105V, S112T, L160S, V184A, N233D, L235F, V257A, I265T, N299D, Y426H, Y430H, L505N, F555H, 1610T, N616E, I632T, L706N, N754D, K1837E, R1936Q, S2030A, S2037G, N2038D, S2077G, M2123K, S2125G, F2215H, K2226Q, K2258Q, V2313A, S2315T, V2333A and Q2335H.

The Factor VIII protein of the invention may e.g. comprise 3-38, 3-25, 4-25, 5-24, 6-23, 7-22, 8-21, 9-20, 10-19, 11-18, 12-17, 13-16 or 14-15 of said substitutions. Preferably, the recombinant Factor VIII protein of the invention comprises 3-25 of said substitutions, and the substitutions are located within different immunogenic clusters. An immunogenic cluster is a peptide identified in a protein, which binds to a plurality of HLA-DR supertypes with a high affinity. In other words, immunogenic clusters are clusters of T-cell epitopes for different HLA supertypes identified in a protein, e.g., as described in more detail in the Examples below. Immunogenic clusters of FVIII are defined in SEQ ID NO: 16-50 and 54 (Table 2). Optionally, there is only one of the recited substitutions per immunogenic cluster. Most preferably, the recombinant Factor VIII protein of the invention comprises 15-19 of said substitutions.

The recombinant Factor VIII protein of the invention comprising at least three substitutions located within different immunogenic clusters preferably comprises at least three amino acid substitutions at positions selected from the group consisting of Y748, L171, S507, N79, S112, L160, V184, N233, 1265, N299, Y426, F555, N616, I632, L706, K1837, R1936, N2038, S2077, S2125, F2215, K2226, K2258, S2315, and V2333. The at least three amino acid substitutions are preferably selected from the group consisting of Y748S, L171Q, S507E, N79S, S112T, L160S, V184A, N233D, I265T, N299D, Y426H, F555H, N616E, I632T, L706N, K1837E, R1936Q, N2038D, S2077G, S2125G, F2215H, K2226Q, K2258Q, S2315T and V2333A.

Preferred FVIII proteins incorporate substitutions at four positions in the A1 region and/or 7 positions in A1 and/or 3 positions in A1A2 and/or 5 positions in A2 and/or 6 positions in A3C1C2, which have more than 100% specific coagulant activity, e.g., according to the following list:

A1: N79, S112, N233, I265; especially N79S, S112T, N233D, I265T

A1: N79, S112, L160, L171, V184, N233, I265; especially N79S, S112T, L160S, L171Q, V184A, N233D, I265T A1A2: N299, Y426, S507; especially N299D, Y426H, S507E A2: F555, N616, I632, L706, Y748; especially F555H, N616E, I632T, L706N, Y748S A3C1C2: N2038, S2077, S2125, K2258, S2315, V2333; especially N2038D, S2077G, S2125G, K2258Q, S2315T, V2333A.

Further preferred FVIII proteins incorporate substitutions at 4 positions in A2 and/or 3 positions in A3C1C2 and/or 4 positions in A3C1C2 and/or 4 positions in A3C1C2 and/or 5 positions in A3C1C2:

A2: F555, N616, L706, Y748; especially F555H, N616E, L706N, Y748S

A3C1C2: S2077, S2315, V2333; especially S2077G, S2315T, V2333A

A3C1C2: N2038, S2077, S2315, V2333; especially N2038D, S2077G, S2315T, V2333A

A3C1C2: S2077, K2258, S2315, V2333; especially S2077G, K2258Q, S2315T, V2333A

A3C1C2: N2038, S2077, K2258, S2315, V2333; especially N2038D, S2077G, K2258Q, S2315T, V2333A.

Preferred combinations with especially good results in coagulant activity (chromogenic coagulant activity, clotting coagulant activity and specific coagulant activity) incorporate substitutions at the following positions:

FVIII-GOF1: L171; S507; Y748; V2333; especially L171Q; S507E; Y748S; V2333A

FVIII-GOF2: L171; N299; N616; V2333; especially L171Q; N299D; N616E; V2333A.

Further preferred combinations with especially good results in reducing cluster score, which accordingly are calculated to strongly reduce immunogenicity, are:

FVIII-LS1: S112; S507; Y748; K1837; N2038; especially S112T; S507E; Y748S; K1837E; N2038D FVIII-LS2: S112; Y426; N754; K1837; N2038; especially S112T; Y426H; N754D; K1837E; N2038D Preferred recombinant Factor VIII proteins of the invention comprise amino acid substitutions at least at positions a. N79S, S112T, N233D, and I265T; and/or
b. N79S, S112T, L160S, L171Q, V184A, N233D, and I265T; and/or
c. N299D, Y426H, and S507E; and/or
d. F555H, N616E, L706N, Y748S; and/or
e. F555H, N616E, I632T, L706N, and Y748S; and/or
f. S2077G, S2315T, and V2333A; and/or
g. N2038D, S2077G, S2315T, and V2333A; and/or
h. S2077G, K2258Q, S2315T, and V2333A; and/or
i. N2038D, S2077G, K2258Q, S2315T, and V2333A; and/or
j. N2038D, S2077G, S2125G, K2258Q, S2315T, and V2333A; and/or
k. L171Q, S507E, Y748S and V2333A; and/or
l. L171Q, N299D, N616E and V2333A; and/or
m. S112T, S507E, Y748S, K1837E and N2038D; and/or
n. S112T, Y426H, N754D, K1837E and N2038D.

Preferred proteins of the invention have the substitutions listed in FIG. 7 herein.

Especially preferred proteins combine at least the substitutions specified under b and c. As shown in FIG. 7, these substitutions in combination lead to high chromogenic and clotting coagulant activities as well as high specific coagulant activities. Further especially preferred proteins of the invention combine at least the substitutions specified under b and c and those specified under d or e and/or f, g, h, i or j and/or K1837E. A protein of the invention may, e.g., include the substitutions specified under b, c and d or e. Other advantageous proteins of the invention comprise the substitutions specified under b, c and d and f, g, h, i or j. Other advantageous proteins of the invention comprise the substitutions specified under b, c and e and f, g, h, i or j.

Optionally, the proteins further comprise K1837E. This substitution has a high effect on the immunogenic score, but appears to have a negative effect on coagulant activity of the protein.

Accordingly, it is also envisaged that proteins of the invention do not comprise a substitution at K1837, or do not comprise K1837E.

Optionally, proteins of the invention, e.g., comprising substitutions Y748S, L171Q, S507E, N79S, S112T, L160S, V184A, N233D, I265T, N299D, Y426H, F555H, I632T, L706N, K1837E, R1936Q, N2038D, S2077G, S2125G, F2215H, K2226Q, K2258Q, S2315T and V2333A do not comprise a substitution at N616 such as N616E. On the other hand, inclusion of this substitution further reduces the immunogenic score, and immunogenicity of the protein, so, in general, inclusion of the substitution is preferred.

In one combination, proteins of the invention comprise the substitutions Y748S, L171Q, N79S, S112T, L160S, V184A, I265T, N299D, Y426H, F555H, I632T, L706N, R1936Q, N2038D, S2077G, S2125G, F2215H, K2226Q, K2258Q, and, optionally, S507E.

The inventors could particularly show advantageous combinations of substitutions of recombinant Factor VIII proteins comprising at least amino acid substitutions at positions N79, S112, L160, L171, V184, N233, I265, N299, Y426, S507, F555, N616, L706, and Y748, wherein preferably the substitutions are N79S, S112T, L160S, L171Q, V184A, N233D, I265T, N299D, Y426H, S507E, F555H, N616E, L706N, and Y748S (e.g., FVIII-14M). Optionally, the protein further includes a substitution at K1837 such as K1837E, and it may comprise the amino acid sequence according to aa 20-1533 of SEQ ID NO: 7 (FVIII-15M), i.e., the mature protein does not comprise the 19 aa N-terminal signal sequence.

A preferred recombinant Factor VIII protein comprises at least 18 amino acid substitutions at positions N79, S112, L160, L171, V184, N233, I265, N299, Y426, S507, F555, N616, L706, Y748, N2038, S2077, S2315 and V2333, wherein preferably the 18 substitutions are N79S, S112T, 1160S, L171 Q, V184A, N233D, I265T, N299D, Y426H, S507E, F555H, N616E, L706N, Y748S, N2038D, S2077G, S2315T and V2333A. Optionally, the protein comprises the amino acid sequence according to aa 20-1533 of SEQ ID NO: 6 (FVIII-18M), i.e., the mature protein does not comprise the 19 aa N-terminal signal sequence.

Another preferred recombinant Factor VIII protein comprises at least 19 amino acid substitutions at positions N79, S112, L160, L171, V184, N233, I265, N299, Y426, S507, F555, N616, L706, Y748, K1837, N2038, S2077, S2315 and V2333, wherein preferably the 19 substitutions are N79S, S112T, L160S, L171Q, V184A, N233D, I265T, N299D, Y426H, S507E, F555H, N616E, L706N, Y748S, K1837E, N2038D, S2077G, S2315T and V2333A. Optionally, the protein comprises the amino acid sequence according to aa 20-1533 of SEQ ID NO: 5 (FVIII-19M), i.e., the mature protein does not comprise the 19 aa N-terminal signal sequence.

Sequences of further FVIII proteins of the invention are provided as SEQ ID NO: 8-15 or 51, wherein, while the sequences all comprise the 19 aa N-terminal signal sequence, the preferred mature FVIII proteins of the invention do not comprise the signal sequence any more. Accordingly, they correspond to aa 20-1533 of SEQ ID NO: 8-15 or 51, respectively.

Preferably, all amino acids selected for substitution in the specified positions reduce the cluster score of the relevant immunogenic cluster.

The recombinant Factor VIII proteins of the invention have a reduced immunogenicity compared to a Factor VIII protein consisting of SEQ ID NO: 2 (FVIII-6rs). Immunogenicity may be determined by an immunogenicity score, which may be calculated as described herein. The immunogenicity score of FVIII-6rs is 7.01, and the immunogenicity score of ReFacto AF® is 10.03. Preferably, Factor VIII proteins of the invention have an immunogenicity score, which is reduced by at least 3, by at least 5, by at least 7, by at least 10, by at least 12, by at least 13 or by at least 15 compared to the Factor VIII protein without the recited substitutions, e.g., compared to FVIII-6rs. For example FVIII-19M has an immunogenicity score of −10.55, i.e., the immunogenicity score is reduced by 17.56 compared to FVIII-6rs.

Preferably, immunogenicity may be determined by an assay comprising co-cultivating dendritic cells incubated with said protein and regulatory T-cell-depleted $CD4^+$ T cells of a donor and testing activation of said T cells. Such an assay, provided by the inventors, is described in further detail below. The T cells may be derived from a healthy donor or from a patient, e.g. from a Hemophilia A patient.

In all recombinant FVIII proteins of the invention, the positions are specified in relation to full length human Factor VIII molecule of SEQ ID NO: 1. In the state of the art, annotation of amino acids in the FVIII molecule differs between authors. This is mainly due to the 19 amino acid signal sequence, which can be included into the amino acid count or can be omitted. This variation of plus or minus 19 amino acids is in general the only difference in numeration for full-length FVIII sequences. For B-domain deleted FVIII sequences, the deletion may also lead to a shift in numeration. For the heavy chain the numeration correlates with the numeration of the full-length FVIII. From the B-domain deletion on the numeration of the light chain is either kept the same as for the full-length FVIII molecule (e.g. Q763 in front of the deletion is followed by D1582 after the deletion) or can be continued as if no deletion has occurred (e.g. Q763 is followed by D764 despite missing amino acids). The continued numeration complicates the comparison of amino acid sequences if it is not known how many amino acids were deleted. The continued numeration is rare and most authors keep the numeration of the full-length FVIII molecule despite B-domain deletion. In accordance with this, in the present invention, the positions of substitutions in the recombinant FVIII protein are specified in relation to full length human FVIII molecule of SEQ ID NO: 1. Nevertheless, the secreted recombinant FVIII protein does not comprise the signal sequence, and typically is a B-domain deleted variant.

It is known in the art that the B-domain is not required for proper coagulant function of FVIII, and therefore, various B-domain deleted FVIII proteins are well known. In the context of the present invention, a B-domain deleted FVIII protein may comprise full or partial deletion(s) of the B-domain. The B-domain deleted FVIII protein may still contain amino-terminal sequences of the B-domain which may e.g. be important for proteolytic processing of the translation product. Moreover, the B-domain deleted FVIII protein may contain one or more fragments of the B-domain in order to retain one or more N-linked glycosylation sites. Preferably, the FVIII protein does not contain any furin cleavage sites, resulting in a single chain protein in which light and heavy chains of the protein are covalently linked.

For example, the B-domain deleted FVIII protein may still comprise 0-200 residues, e.g., 1-100 residues, preferably 8 to 90 residues of the B-domain. The remaining residues of the B-domain may derive from the N-terminus and/or the C-terminus and/or from internal regions of the B-domain. For example, the remaining residues from the C-terminus of the B-domain may contain 1-100, preferably 20-90, more preferably 86 residues. In other embodiments the remaining residues from the C-terminus may contain 1-20 residues, e.g. 4 residues. For example, the remaining residues from the N-terminus of the B-domain may contain 1-100, preferably 2-20 residues, more preferably 2-10 residues, more preferably 4 residues. For example, the remaining residues from internal regions of the B-domain may contain 2-20, preferably 2-10, more preferably 4 to 8 residues. In a preferred embodiment, the FVIII protein comprises 86 C-terminal residues of the B-domain and 4 residues from the N-terminus of the B-domain, e.g., as in FVIII-19M.

Throughout the invention, the recombinant Factor VIII protein of the invention may have at least 90%, at least 95%, at least 96%, at least 97%, at least 98%, or at least 99% sequence identity to a mature (i.e., not including the signal sequence) FVIII-19M protein of SEQ ID NO: 5, wherein only the A1, a1, A2, a2, a3, A3, C1 and C2 domains (residues 20-759 and residues 1668-2351) are considered for determination of sequence identity. In other words, for determination of sequence identity, the B-domain (residues 760-1667 of the full length human sequence SE ID NO: 1, and the residues corresponding thereto in partially B-domain deleted proteins) and the signal sequence (residues 1-19) are not taken into account.

Accordingly, the % sequence identity of a mature full length human Factor VIII protein of SEQ ID NO: 1, or to a B-domain deleted variant thereof, e.g., according to SEQ ID NO: 3, to a FVIII protein of SEQ ID NO: 5 is the same, in particular, it is 98.67%. Preferred FVIII proteins of the invention have a sequence identity to SEQ ID NO: 5 of at least 98.74%.

For example, for a mature B-domain deleted FVIII protein with only one of the recited substitutions, the % sequence identity to mature FVIII-19M protein of SEQ ID NO: 5 is determined over the A1, a1, A2, a2, a3, A3, C1 and C2 domains, i.e. 18 of 1424 amino acids are substituted, and the protein accordingly has at least 98.74% sequence identity to FVIII-19M protein of SEQ ID NO: 5. For a mature B-domain deleted FVIII protein with 3 of the recited substitutions also occurring in FVIII-19M, the % sequence identity to mature FVIII-19M protein of SEQ ID NO: 5, is determined over the A1, a1, A2, a2, a3, A3, C1 and C2 domains, i.e. 16 of 1424 amino acids are substituted, and the protein accordingly has 98.88% sequence identity to FVIII-19M protein of SEQ ID NO: 5. A mature B-domain deleted FVIII protein of the invention with 4 of the recited substitutions also occurring in FVIII-19M has 15 of 1424 amino acids substituted, and thus has 98.95% sequence identity. A mature B-domain deleted FVIII protein incorporating all 38 recited substitutions has 19 additional substitutions compared to in FVIII-19M, and thus has 98.67% sequence identity to FVIII-19M.

Sequence identity is furthermore determined for the Factor VIII part (as defined, based on the A1, a1, A2, a2, a3, A3, C1 and C2 domains) of the molecule only, i.e., if the protein is a fusion protein (for example, contains insertions of any size), fused or inserted parts, protein domains or regions (e.g., as further described herein) are not taken into account. Thus, for the determination of sequence identity, if present, fusion partners are ignored, and the % sequence identity to A1, a1, A2, a2, a3, A3, C1 and C2 domains is then calculated. Sequence identity can be calculated as known in the art, e.g., using the Needleman-Wunsch algorithm or, preferably, the Smith-Waterman algorithm (Smith et al., 1981. Identification of Common Molecular Subseqences, J Mol Biol. 147: 195-197).

In one embodiment, all residues of the FVIII protein, in particular, with regard to the A1, a1, A2, a2, a3, A3, C1 and C2 domains, except for the substitutions specified herein, correspond to (i.e., are identical to) residues of human Factor VIII protein of SEQ ID NO: 1. Optionally, this may also apply for the B-domain or those parts of the B-domain which are present.

In another embodiment, the FVIII protein of the invention incorporates further mutations, e.g., mutations known in the art to reduce immunogenicity either with regard to further T cell epitopes and/or B cell epitopes, and/or mutations known in the art to improve serum half-life of the protein and/or mutations facilitating purification of the protein, e.g., leading to a single chain protein.

Preferably, the FVIII protein of the invention is a fusion protein, e.g., a fusion protein of a recombinant Factor VIII protein having at least 90%, at least 95%, at least 96%, at least 97%, at least 98% or at least 99% sequence identity to a FVIII-19M as specified in SEQ ID NO: 5, wherein only the A1, a1, A2, a2, a3, A3, C1 and C2 domains are considered for calculation of sequence identity.

The fusion partner preferably extends the in vivo serum half-life of the FVIII protein of the invention. The fusion partner may be selected from the group comprising an Fc region, albumin, an albumin binding sequence, PAS polypeptides, HAP polypeptides, the C-terminal peptide of the beta subunit of chorionic gonadotropin, albumin-binding small molecules, and combinations thereof. The FVIII protein may alternatively or additionally be covalently linked to non-protein fusion partners such as PEG (polyethylenglycol) and/or HES (hydroxyethyl starch). PAS polypeptides or PAS sequences are polypeptides comprising an amino acid sequence comprising mainly alanine and serine residues or comprising mainly alanine, proline and serine residues, the PAS sequences forming a random coil conformation under physiological conditions, as defined in WO 2015/023894. HAP polypeptides or sequences are homo-amino acid polymer (HAP), comprising e.g., repetitive sequences of Glycine or Glycine and Serine, as defined in WO 2015/023894. Potential fusions, fusion partners and combinations thereof are described in more detail e.g., in WO 2015/023894.

Preferably, for therapeutic applications, the recombinant FVIII protein is at least fused to an Fc region. Fusion proteins of FVIII to Fc regions are known in the state of the art to reduce immunogenicity (Krishnamoorthy et al., Recombinant factor VIII Fc (rFVIIIFc) fusion protein reduces immunogenicity and induces tolerance in hemophilia A mice, Cell. Immunol. 2016, http://dx.doi.org/10.1016/j.cellimm.2015.12.2008; Carcao et al., Recombinant factor VIII Fc fusion protein for immune tolerance induction in patients with severe haemophilia A with inhibitors—A retrospective analysis. Haemophilia 2018:1-8).

Fusion partners may e.g., be linked to the N-terminus or the C-terminus of the FVIII protein of the invention, but they may also be inserted within the FVIII sequence, as long as the FVIII protein remains functional as defined herein. As described above, for determination of sequence identity, insertions of, e.g., one, two, three, four, five, six, seven, eight, nine or ten fusion partners, as defined herein, are not considered to reduce sequence identity.

The inventors found that a high proportion of the FVIII protein of the invention was produced as a single chain protein in the cell lines selected for production. Production of FVIII as a single chain protein is not believed to reduce coagulant activity, but may be beneficial for purification. To simplify purification, the FVIII protein of the invention may be a single chain protein or at least have a proportion of at least 40%, at least 50%, at least 60%, at least 70%, at least 80%, at least 90% or at least 95% single chain protein. Alternatively, the FVIII protein of the invention may be produced as a heterodimeric FVIII protein. Preferably, the FVIII protein of the invention is a single chain B-domain deleted Factor VIII protein.

Recombinant single chain FVIII proteins are known in the art, wherein, e.g., at least part of the B-domain and 4 amino acids of the adjacent acidic a3 domain (e.g., residues 784-1671 of full length FVIII) are removed, in particular, removing the furin cleavage-site (EMA/CHMP/699390/2016-Assessment report AFSTYLA). An exemplary single chain FVIII protein is provided as SEQ ID NO: 4. An exemplary FVIII single chain protein based on SEQ ID NO: 4 which incorporates 19 mutations as specified herein, e.g., the same 19 mutations incorporated in FVIII-19M, lacks 4 amino acids of the a3 domains of FVIII-19M, i.e., it has 99.72% (at least 99% sequence identity) to SEQ ID NO: 5. Said protein may be B-domain deleted, and it may be a fusion protein, e.g., as described above.

The protein may further be glycosylated and/or sulfated. Preferably, post-translational modifications such as glycosylation and/or sulfation of the protein occur in a human cell.

In one embodiment of the invention, the protein is capable of association with vWF. For example, the binding potency of the FVIII protein of the invention to vWF is 0%-100%, 10%-90%, 20-80%, 30-70%, 40-60% or 50-60% of the binding potency of ReFacto AF® to vWF, which can be determined by an ELISA-based method, e.g., as described herein. As shown herein, the binding capacity of a FVIII protein of the invention comprising several of the recited mutations may be reduced compared to ReFacto AF®, e.g., to less than 60%.

The protein of the invention is preferably stable in human plasma in vitro and in vivo, so that it can be pharmaceutically used. The inventors could show that about 83% of chromogenic coagulant activity of FVIII-19M were maintained after in vitro incubation in human plasma at 37° C. for 24 hours. For FVIII-6rs, under the same conditions, about 91% coagulant activity were maintained, for ReFacto AF® and NUWIQ®, it was 97%.

Preferably, in vivo, the half-life of the FVIII protein of the invention in human serum (in a patient without inhibitors) is about at least 6 hours, preferably, at least 12 hours, at least 18 hours, at least 24 hours, or at least to 30 hours. As defined herein, the FVIII protein may be a FVIII protein without fusion partner, or it may be a fusion protein as defined herein. Optionally, the specified half-life is already obtained without fusion partners. In case of the presence of further partners the half-life of the FVIII protein may be the same, or even longer.

The invention also provides a nucleic acid encoding the recombinant Factor VIII protein of the invention. The nucleic acid preferably encodes the FVIII with an N-terminal signal sequence, e.g., the 19 aa signal sequence of SEQ ID NO: 1. Preferred nucleic acids of the invention thus encode SEQ ID NO: 5-15 or 51. The nucleic acids of the invention may be DNA molecules or RNA molecules. The nucleic acids may be optimized for expression in the host cell, e.g., in a human cell. A nucleic acid encoding FVIII-19M is provided as SEQ ID NO: 52. For comparison, the nucleic acid sequence of FVIII-6rs is provided as SEQ ID NO: 53.

The nucleic acid preferably is an expression vector, e.g., suitable for expression of said recombinant Factor VIII protein in a bacterial, yeast, plant or animal cell, e.g., preferably, a mammalian or in particular, a human cell, or in another cell line suitable for production of a therapeutic FVIII protein, e.g., a CHO cell. The expression vector comprises the sequence encoding the FVIII protein, preferably, in codon-optimized form, under the functional control of a suitable promoter, which may be a constitutive or an inducible promoter. The promoter may be a promoter not associated with expression of FVIII in nature, e.g., EF-1□ or a heterologous promoter, e.g., CMV or SV40.

Alternatively, the nucleic acid may be a vector suitable for gene therapy, e.g., for gene therapy of a human patient. Vectors suitable for gene therapy are known in the art, e.g., virus-based vectors e.g., based on adenovirus or adeno-associated virus or based on retrovirus, such as lentiviral vectors etc. or non virus-based vectors such as but not limited to small plasmids and minicircles or transposon-based vectors. An AAV-based vector of the invention may e.g., be packaged in AAV particles for gene therapy of Hemophilia A patients.

The invention further relates to a host cell comprising the nucleic acid of the invention. The host cell may be a bacterial or yeast cell, but typically, it is a mammalian cell, preferably, a human cell. The host cell preferably is a human cell comprising an expression vector suitable for expression of said recombinant Factor VIII protein in said human cell. The cell may be transiently or stably transfected with the nucleic acid of the invention. The cell may be a cell line, a primary cell or a stem cell. For production of the protein, the cell typically is a cell line such as a HEK cell, such as a HEK-293 cell, a CHO cell, a BHK cell, a human embryonic retinal cell such as Crucell's Per.C6 or a human amniocyte cell such as CAP.

The cell may be an autologous cell of a Hemophilia A patient suitable for producing FVIII in the patient after transfection and reintroduction into the patient's body. The cell may be a stem cell, e.g., a hematopoietic stem cell, but preferably it is not an embryonic stem cell, in particular when the patient is a human. The cell may also be hepatocyte, a liver sinusoidal endothelial cell or a thrombocyte.

Cell lines expressing the protein of the invention may also be used in a method of preparing the protein of the invention, comprising cultivating said cells under conditions suitable for expression of the FVIII protein and purifying said protein, e.g., using a plurality of methods, e.g., as described herein.

The invention thus provides a pharmaceutical composition comprising the recombinant Factor VIII protein of the invention, the nucleic acid of the invention or the host cell of the invention. Such pharmaceutical compositions may comprise suitable excipients, e.g., a buffer, a stabilizing agent, a bulking agent, a preservative, another (e.g., recombinant) protein or combinations thereof. A suitable buffer for formulation may e.g. contain 205 mM NaCl, 5.3 mM $CaCl_2$, 6.7 mM L-Histidine, 1.3% Sucrose and 0.013% Tween 20 in distilled water and have a pH of 7.0. In the context of the invention, if not explicitly stated otherwise, "a" is understood to mean one or more.

The pharmaceutical composition may be formulated, e.g., for intravenous or subcutaneous application. Generally, it is for administration as slow IV push bolus injection. Continuous infusion is indicated e.g., for patients requiring admission for severe bleeds or surgical procedures. Oral application, which may contribute to tolerance induction, is also possible, e.g., after expression in plants.

Pharmaceutical compositions comprising FVIII can be lyophilized. Dosages and treatment schemes may be chosen as appropriate, e.g., for prophylaxis of bleeding or with intermittent, on-demand therapy for bleeding events.

The invention also provides a pharmaceutical composition comprising the FVIII protein of the invention in combination with an immunosuppressive agent (e.g., methylprednisolone, prednisolone, dexamethasone, cyclophosphamide, rituximab, and/or cyclosporin), and/or it may be for administration at substantially the same time with (e.g. within minutes to 12 hours) with such an agent.

The pharmaceutical composition, e.g., comprising the protein of the invention, may be for use in treating a patient in need thereof, in particular, a Hemophilia A patient, e.g., a patient with acquired hemophilia involving an autoimmune response to FVIII or a congenital Hemophilia A patient. Mammals such as mice may be treated with the pharmaceutical composition of the invention, but the patient typically is a human patient.

It is particularly advantageous in settings wherein a reduced immunogenicity is desired, e.g., for use in treating a patient with Hemophilia A not previously treated with any recombinant or plasmatic Factor VIII protein. According to the invention, the incidence and/or severity of generation of antibodies including inhibiting antibodies in the patient is thus reduced compared to treatment with conventional FVIII, or preferably, the generation of antibodies including inhibiting antibodies is prevented. The pharmaceutical composition of the invention may also be used for treatment of a patient previously treated with a recombinant and/or plasmatic Factor VIII protein. In a patient who has an antibody including an inhibitory antibody response to a recombinant and/or plasmatic Factor VIII protein, the pharmaceutical compositions may e.g., be used for immune tolerance induction (ITI) treatment, as it is desired to use a FVIII protein having a low immunogenicity or even tolerogenic characteristics (Carcao et al., Recombinant factor VIII Fc fusion protein for immune tolerance induction in patients with severe haemophilia A with inhibitors—A retrospective analysis. Haemophilia 2018:1-8). The compositions of the invention may thus also be used for rescue ITI. The pharmaceutical compositions may also be advantageously used in a patient who has had an antibody response including an inhibitory antibody response to a recombinant and/or plasmatic Factor VIII protein who has been treated by ITI. Moreover, the pharmaceutical compositions of the invention may be used as bypassing agent in patients with inhibitory antibodies.

The combination of substitutions described herein reduces the immunogenicity score for all subjects having at least one of the analyzed HLA-DR supertype alleles (DRB1*0101, DRB1*0301, DRB1*0401, DRB1*0701, DRB1*0801, DRB1*1101, DRB1*1301, DRB1*1501). These subtypes are present in more than 90% of the population (cf. Southwood et al., J. Immunol. 1998; 160; 3363-3373). FVIII of the invention can thus advantageously be used for treatment of all patients in need thereof, in particular those having one of the HLA-DR supertype alleles. Table 1 shows, for the Example of FVIII-19M, that immunogenicity is differently reduced for patients with different alleles.

TABLE 1

A-C: Individual T cell Epitope Measure (ITEM) scores indicating the immunogenicity for FVIII-6rs (A) and FVIII-19M (B) for different HLA-DR supertypes, and absolute reduction of the Immunogenicity for FVIII-19M compared to FVIII-6rs for different HLA-DR supertypes (C). The ITEM Score is based on the number and intensity of the EpiMatrix Hits (method see below) for a pair of alleles normalized for the length of the protein. A low ITEM score in Table 1A or B reflects a low immunogenicity. A high reduction in the ITEM score in Table 1C, i.e., a high positive value in said table, reflects a high benefit from the substitutions introduced.

| | DRB1* 0101 | DRB1* 0301 | DRB1* 0401 | DRB1* 0701 | DRB1* 0801 | DRB1* 1101 | DRB1* 1301 | DRB1* 1501 |
|---|---|---|---|---|---|---|---|---|
| A: FVIII-6rs | | | | | | | | |
| DRB1*0101 | 1.26 | | | | | | | |
| DRB1*0301 | 0.54 | −0.18 | | | | | | |
| DRB1*0401 | 9.49 | 8.77 | 17.73 | | | | | |
| DRB1*0701 | 12.25 | 11.54 | 20.49 | 23.25 | | | | |
| DRB1*0801 | 8.63 | 7.91 | 16.86 | 19.62 | 16 | | | |
| DRB1*1101 | 0.3 | −0.42 | 8.53 | 11.29 | 7.67 | −0.66 | | |
| DRB1*1301 | −0.09 | −0.81 | 8.14 | 10.9 | 7.28 | −1.05 | −1.44 | |
| DRB1*1501 | 0.71 | 0 | 8.95 | 11.71 | 8.08 | −0.25 | −0.64 | 0.17 |
| B: FVIII-19M | | | | | | | | |
| DRB1*0101 | −15.51 | | | | | | | |
| DRB1*0301 | −15.64 | −15.77 | | | | | | |
| DRB1*0401 | −6.51 | −6.64 | 2.48 | | | | | |
| DRB1*0701 | −5.64 | −5.77 | 3.35 | 4.23 | | | | |
| DRB1*0801 | −8.86 | −8.99 | 0.14 | 1.01 | −2.21 | | | |
| DRB1*1101 | −19.4 | −19.53 | −10.41 | −9.54 | −12.75 | −23.3 | | |

TABLE 1-continued

A-C: Individual T cell Epitope Measure (ITEM) scores indicating the immunogenicity for FVIII-6rs (A) and FVIII-19M (B) for different HLA-DR supertypes, and absolute reduction of the Immunogenicity for FVIII-19M compared to FVIII-6rs for different HLA-DR supertypes (C). The ITEM Score is based on the number and intensity of the EpiMatrix Hits (method see below) for a pair of alleles normalized for the length of the protein. A low ITEM score in Table 1A or B reflects a low immunogenicity. A high reduction in the ITEM score in Table 1C, i.e., a high positive value in said table, reflects a high benefit from the substitutions introduced.

| | DRB1* 0101 | DRB1* 0301 | DRB1* 0401 | DRB1* 0701 | DRB1* 0801 | DRB1* 1101 | DRB1* 1301 | DRB1* 1501 |
|---|---|---|---|---|---|---|---|---|
| DRB1*1301 | −15.07 | −15.2 | −6.07 | 5.2 | −8.42 | −18.96 | −14.63 | |
| DRB1*1501 | −17.6 | −17.73 | −8.61 | −7.74 | −10.96 | −21.5 | −17.16 | −19.7 |
| C: Absolute reduction of the immunogenicity score for FVIII-19M compared to FVIII-6rs | | | | | | | | |
| DRB1*0101 | 16.77 | | | | | | | |
| DRB1*0301 | 16.18 | 15.59 | | | | | | |
| DRB1*0401 | 16 | 15.41 | 15.25 | | | | | |
| DRB1*0701 | 17.89 | 17.31 | 17.14 | 19.02 | | | | |
| DRB1*0801 | 17.49 | 16.9 | 16.72 | 18.61 | 18.21 | | | |
| DRB1*1101 | 19.7 | 19.11 | 18.94 | 20.83 | 20.42 | 22.64 | | |
| DRB1*1301 | 14.98 | 14.39 | 14.21 | 16.1 | 15.7 | 17.91 | 13.19 | |
| DRB1*1501 | 18.31 | 17.73 | 17.56 | 19.45 | 19.04 | 21.25 | 16.52 | 19.87 |

For all alleles analyzed, there is a reduction in the immunogenicity score, in particular, the reduction in immunogenicity score is more than 13. A particularly high reduction in the immunogenicity score of more than 17 shows that patients having one of the following combination of HLA types can particularly benefit from treatment with the pharmaceutical composition of the invention:

DRB1*0701 in combination with DRB1*0101, DRB1*0301, DRB1*0401, DRB1*0701, DRB1*0801, DRB1*1101, or DRB1*1501;

DRB1*0801 in combination with DRB1*0101, DRB1*0701, DRB1*0801, DRB1*1101, or DRB1*1501;

DRB1*1101 in combination with DRB1*0101, DRB1*0301, DRB1*0401, DRB1*0701, DRB1*0801, DRB1*1101, DRB1*1301, or DRB1*1501;

DRB*1301 in combination with DRB1*1101;

DRB1*1501 in combination with DRB1*0101, DRB1*0301, DRB1*0401, DRB1*0701, DRB1*0801, DRB1*1101, DRB1*1501

A still higher reduction in the immunogenicity score of more than 20 shows that patients having one of the following combination of HLA types can even more particularly benefit from treatment with the pharmaceutical composition of the invention: DRB1*1101 in combination with DRB1*0701, DRB1*0801, DRB1*1101, or DRB1*1501. Treatment of patients having a particularly high reduction in immunogenic score is preferred.

The invention provides an in vitro method for preparing a FVIII protein of the invention, comprising culturing a host cell of the invention expressing said FVIII protein under suitable conditions, and isolating said FVIII protein, wherein the protein is optionally formulated as a pharmaceutical composition. As described herein, the host cell preferably is a human cell.

In one embodiment, the in vitro method for preparing the FVIII protein of the invention further includes steps for analyzing a FVIII protein for the presence of T cell epitopes for identifying amino acid substitutions in a position that eliminates one or more of the T cell epitopes and testing the amino acid substitutions for coagulant activity of corresponding mutants before culturing the host cell expressing the resulting FVIII protein of the invention. Thus, the invention also provides an in vitro method for preparing a protein, e.g., a Factor VIII protein of the invention, having reduced immunogenicity, comprising a) analyzing a Factor VIII protein, e.g., a wildtype Factor VIII protein, for the presence of T-cell epitopes relevant for a significant proportion of humans;

b) preparing a plurality of mutants of said protein comprising at least one amino acid substitution, preferably, only one amino acid substitution in a position that eliminates one of the T cell epitopes identified in step a, and analyzing coagulant activity of said mutants;

c) preparing a plurality of mutants of said protein each comprising at least three of the substitutions identified in step b as leading to a protein having at least 50% of the coagulant activity of a Factor VIII protein of SEQ ID NO: 2 or a FVIII protein having 80-120%, preferably 90-110%, of the coagulant activity of the Factor VIII protein of SEQ ID NO: 2, wherein the substitutions are located within different immunogenic clusters, and wherein each of said mutants comprises substitutions identified in all immunogenic clusters of a contiguous region of said protein, and analyzing coagulant activity of said mutants;

d) if any of the mutants of step c have a coagulant activity of less than 50% of the coagulant activity of a Factor VIII protein of SEQ ID NO: 2 or a FVIII protein having 80-120%, preferably 90-110%, of the coagulant activity of the Factor VIII protein of SEQ ID NO: 2, repeating preparing a plurality of mutants of said protein each comprising at least three of the substitutions identified in step b as leading to a protein having at least 50% of the coagulant activity of a Factor VIII protein of SEQ ID NO: 2 or a FVIII protein having 80-120%, preferably 90-110%, of the coagulant activity of the Factor VIII protein of SEQ ID NO: 2, wherein the substitutions are located within different immunogenic clusters, and wherein different combinations of substitutions identified in said contiguous region of said protein are prepared, and analyzing coagulant activity of said mutants;

e) preparing a Factor VIII protein comprising at least three, preferably, at least 10, at least 14, at least 15, at least 16, at least 18 or at least 19 substitutions found not to reduce coagulant activity of said protein to less than 50% of the coagulant activity of a Factor VIII protein of SEQ ID NO: 2 or a FVIII protein having 80-120%, preferably 90-110%, of the coagulant activity of the Factor VIII protein of SEQ ID NO: 2 in combination with other substitutions included; and optionally f) formulating said protein as a pharmaceutical composition.

The analysis in step a is preferably done in silico, e.g., by analyzing the protein for the presence of immunogenic clusters as described herein. Accordingly, step b then eliminates one of the immunogenic clusters identified. Alternatively, the analysis for T cell epitopes can be performed in vitro, e.g., by eluting peptides from MHC class II of humans.

Preferably, the coagulant activity in steps c, d, and e is at least 80% or at least 100% of the coagulant activity of a Factor VIII protein of SEQ ID NO: 2 or a FVIII protein having 80-120%, preferably 90-110%, of the coagulant activity of the Factor VIII protein of SEQ ID NO: 2. FVIII proteins having 80-120%, preferably 90-110%, of the coagulant activity of the Factor VIII protein of SEQ ID NO: 2 can e.g., be wt human FVIII or a B-domain deleted variant thereof such as ReFacto AF®.

Optionally, the protein of step e may be modified to comprise further mutations, in particular, it may be expressed as a fusion protein, e.g., with one, two or more of the fusion partners disclosed therein, preferably, as a fusion protein with an Fc region.

In a method for preparing a Factor VIII protein having reduced immunogenicity, the positions for amino acid substitutions identified after in silico analysis are Y748, L171, S507, N79, I80, I105, S112, L160, V184, N233, L235, V257, I265, N299, Y426, Y430, L505, F555, I610, N616, I632, L706, N754, K1837, R1936, S2030, S2037, N2038, S2077, M2123, S2125, F2215, K2226, K2258, V2313, S2315, V2333 and Q2335. Preferably, substitutions of N are independently selected from the group consisting of D, H, S and E; substitution of I are independently selected from the group consisting of T and V; substitutions of S are independently selected from the group consisting of A, N, G, T and E; substitutions of L are independently selected from the group consisting of N, Q, F and S; substitutions of V are independently selected from the group consisting of A and T; substitutions of Y are independently selected from the group consisting of N, H and S; substitutions of F are independently selected from the group consisting of H and S; substitutions of K are independently selected from the group consisting of N, D, E, Q, S and T; substitutions of R are independently selected from the group consisting of Q, H and S; substitutions of M are selected from the group consisting of R, Q, K and T; and/or substitutions of Q are selected from the group consisting of R, D, E, H and K.

The present invention further provides an assay for determining immunogenicity of a protein, e.g., a FVIII protein of the invention, comprising co-cultivating dendritic cells incubated with said protein and regulatory T-cell-depleted CD4+ T cells of a donor (e.g., a healthy human or a patient, e.g., with Hemophilia A) and testing activation of said T cells. For such an assay, monocytes may be purified, e.g., from PBMCs, differentiated to immature DCs (iDCs) (e.g., in the presence of IL-4 and GM-CSF) and finally stimulated to become mature DCs (mDCs) (e.g., using LPS or a mixture of cytokines such as IL-1 beta, IL-6 and TNF-alpha) and, at the same time, incubated with the antigen, i.e., the protein of interest. CD4+CD25-T cells are purified from PBMCs of the same donor, preferably, from the same batch of PBMC, labeled with CFSE (Carboxyfluorescein diacetate succinimidyl ester) for later detection of proliferation and cultivated prior to co-cultivation, e.g., to provide time for recovery of the cells and removal of not steadily bound CFSE. After co-culture with the DC, which preferably takes place at a ratio of DC:T cells of at least 1:10, e.g., for about 12 h to about 2 weeks, for 1 day to 9 days or 2 days to 7 days, the T cells are analyzed for activation and/or proliferation by flow cytometry. Alternatively or additionally, the supernatant may be analyzed for cytokines. Preferable conditions for the assay are described in the examples below. This assay has the advantage that it allows for assessment of both primary and secondary T-cell-mediated immune responses in the absence of regulatory CD25+ T cells, which facilitates detection of immune responses. The results are expected to correlate with immunogenicity of the protein in vivo.

For the de-immunized FVIII protein FVIII-19M, the assay confirmed that, in the majority of subjects analyzed, there was a reduced T cell proliferation in response to FVIII-19M. It can be concluded that a low immunogenicity score correlated with a low immunogenicity of the protein in the in vitro assay, i.e., the substitutions in the epitopes identified in silico translates into a reduced immunogenicity.

All publications cited herein are fully incorporated herewith. The invention is further illustrated by the following examples, which are not to be understood as limiting the scope of the invention.

EXAMPLES

An initial in silico analysis of peptides in human FVIII binding to the MHC class II (T cell epitopes) was performed with the EPIMATRIX tools (Epivax, Providence, RI, USA), which predicts the binding potential with respect to a panel of eight common Class II supertype alleles (DRB1*0101, DRB1*0301, DRB1*0401, DRB1*0701, DRB1*0801, DRB1*1110, DRB1*1301, DRB1*1501), covering the majority of the human population (>90%) and the ClustiMer algorithm to identify putative T cell epitope clusters (designated immunogenic clusters). The analysis was run for the FVIII sequence of SEQ ID NO: 2 (FVIII-6rs), comprising 1514 amino acids, excluding the 19 amino acids of the signal sequence and 818 amino acids of the B domain. The excluded amino acids of the B domain did not interfere with either the furin or the thrombin cleavage sites. The in silico tools revealed a total of 52 immunogenic peptide clusters, with cluster scores ranging between 4 and 34, indicating a very high binding affinity at high values and a lower affinity at low values. The clusters comprised between 14 and 22 amino acids and some clusters were overlapping by a few amino acids.

For 12 of the 52 clusters, amino acid mutations were excluded, either due to interference with regions important for activity, binding or stability or due to the lack of possible exchanges. In order to de-immunize the remaining 40 clusters, 74 mutations were selected. The exchanged amino acids were preferably based on changes naturally occurring in other species. If no natural changes were available, amino acid exchanges were selected from point accepted mutation (PAM) matrices which contain mutations that occurred by natural selection. In particular, based on PAM matrices, substitutions of N are independently selected from the group consisting of D, H, S; wherein substitution of I is T; wherein substitutions of S are independently selected from the group consisting of A, N, G, T; wherein substitutions of L are independently selected from the group consisting of N and Q; wherein substitutions of V are independently selected from the group consisting of A and T; wherein substitutions of Y are independently selected from the group consisting of N and H; wherein substitutions of F are independently selected from the group consisting of H and S; wherein substitutions of K are independently selected from the group consisting of N, D, E, Q, S and T; wherein substitutions of R are independently selected from the group consisting of Q, H and S; wherein substitutions of M are selected from the group consisting of R, Q, K and T; and/or wherein substitutions of Q are selected from the group consisting of R, D, E, H and K.

For some clusters up to three mutations were indicated, all leading to a strong reduction in the cluster score. In these cases, all mutations were selected for the incorporation. In case an additional mutation only led to a low reduction in the score, this mutation was set aside. Additionally, mutations in live clusters were completely set aside, as the total score of the cluster was already low and the predicted improvement by the mutations was marginal. These exclusion criteria led to the reduction from 74 to 57 mutations for the incorporation into B-domain deleted (BDD)-FVIII:

N79S, I80T, I105V, L107N, S112T, L160S, L171 Q, V184A, F214H, N233D, L235F, V257A, I265T, N299D, I1310T, F312S, Y426H, Y430H, L481 N, F484S, L505N, S507E, L548N, F555H, I610T, N616E, F627H, I632T, Y657D, M701K, L706N, Y748S, N754D, F1710H, F1794H, K1837E, R1936Q, F1937H, L1963Q, S2030A, S2037G, N2038D, S2077G, M2123K, S2125G, Y2134H, Y2167N, F2215H, K2226Q, F2253H, K2258Q, V2276A, F2279H, V2313A, S2315T, V2333A, Q2335H.

TABLE 2

Immunogenic clusters identified in FVIII

| SEQ ID NO: | Cluster | Mutation | Initial cluster score | Cluster score with mutation | Notes |
|---|---|---|---|---|---|
| 16 | DHLFNIAKPRPPWMG | N79S | 7.95 | -5.77 | |
| | | I80T | 7.95 | -5.77 | |
| 17 | YDTVVITLKNMASHPVSL | I105V | 30.62 | 2.57 | |
| | | L107N | 30.62 | 2.57 | |
| | | S112T | 30.62 | 2.57 | |
| 18 | VWQVLKENGPMASDPL | L160S | 7.03 | -3.12 | |
| 19 | SDPLCLTYSYLSHVDLVK | L171Q | 9.95 | -1.25 | |
| 20 | HVDLVKDLNSGLIGAL | V184A | 12.53 | 3.48 | |
| 21 | TQTLHKFILLFAVFDEGK | F214H | 13.64 | -0.24 | |
| 22 | GKSWHSETKNSLMQD | N233D | 7.29 | -3.96 | |
| | | L235F | 7.29 | -3.96 | |
| 23 | MHTVNGYVNRSLPGLIG | V257A | 13.7 | -1.99 | |
| | | I265T | 13.7 | -1.99 | |
| 24 | GHTFLVRNHRQASLEIS | N299D | 14.01 | -0.37 | |
| 25 | ISPITFLTAQTLLMDLG | I310T | 25.2 | 12.74 | |
| | | F312S | 25.2 | -2.07 | Score in combination with I310T |
| 26 | DRSYKSQYLNNGPQRIGRK | Y426H | 14.68 | -5.13 | |
| | | Y430H | 14.68 | -5.13 | |
| 27 | GDTLLIIFKNQASRPYNIY | L481N | 30.49 | 4.94 | |
| | | F484S | 30.49 | 4.94 | |
| 28 | ITDVRPLYSRRLPKGVKHL | L505N | 16.09 | -4.74 | |
| | | S507E | 16.09 | -4.74 | |
| 29 | PRCLTRYYSSFVNMERDLASGL | L548N | 19.1 | -0.74 | |
| | | F555H | 19.1 | -0.74 | |
| 30 | TENIQRFLPNPAGVQLED | I610T | 17.73 | -6.49 | |
| | | N616E | 17.73 | -6.49 | |
| 31 | PEFQASNIMHSINGYVFDS | F627H | 12.7 | -3.78 | |
| | | I632T | 12.7 | -3.78 | |
| 32 | EVAYWYILSIGAQTDFL | Y657D | 17.4 | -3.84 | |
| 33 | ETVFMSMENPGLWIL | M701K | 16 | 0.45 | |
| | | L706N | 16 | 0.45 | |
| 34 | ISAYLLSKNNAIEPRS | Y748S | 24.24 | -2.62 | |
| | | N754D | 24.24 | -2.62 | |
| 35 | PRSFQKKTRHYFIAA | F1710H | 6.3 | -2.28 | |

TABLE 2-continued

Immunogenic clusters identified in FVIII

| SEQ ID NO: | Cluster | Mutation | Initial cluster score | Cluster score with mutation | Notes |
|---|---|---|---|---|---|
| 36 | MVTFRNQASRPYSFYS | F1794H | 13.23 | -4.73 | |
| 37 | KTYFWKVQHHMAPTKD | K1837E | 8.59 | -1.3 | |
| 38 | DPTFKENYRFHAINGYIMDTL | R1936Q | 17.3 | 7.72 | |
| | | F1937H | 17.3 | -7.05 | Score in combination with R1936Q |
| 39 | DQRIRWYLLSMGSNENIHS | L1963Q | 18.81 | 1.99 | |
| 54 | GEHLHAGMSTLFLVYS | S2030A | -0.9 | -4.6 | |
| 40 | MSTLFLVYSNKCQTPL | S2037G | 14.83 | -4.83 | |
| | | N2038D | 14.83 | -4.83 | |
| 41 | PKLARLHYSGSINAWSTKE | S2077G | 11.91 | -3.34 | |
| 42 | SSLYISQFIIMYSLDGKKW | M2123K | 16.48 | 0.93 | |
| | | S2125G | 16.48 | 0.93 | |
| 43 | GKKWQTYRGNSTGTLMVF | Y2134H | 13.52 | -0.14 | |
| 44 | IARYIRLHPTHYSIRST | Y2167N | 9.4 | 1.07 | |
| 45 | SSYFTNMFATWSPSK | F2215H | 4.91 | -5.77 | |
| 46 | KARLHLQGRSNAWRPQV | K2226Q | 6.51 | -2.05 | |
| 47 | WLQVDFQKTMKVTGVTT | F2253H | 6.29 | -0.57 | |
| | | K2258Q | 6.29 | -5.68 | |
| 48 | TSMYVKEFLISSSQDGHQW | V2276A | 16.48 | -3.59 | Score in combination with F2279H |
| | | F2279H | 16.48 | 2.33 | |
| 49 | QDSFTPVVNSLDPPLLTRY | V2313A | 8.19 | -5.41 | |
| | | S2315T | 8.19 | -3.3 | |
| 50 | PQSWVHQIALRMEVL | V2333A | 9.56 | -1.52 | |
| | | Q2335H | 9.56 | -1.52 | |

The incorporation of the mutations was performed in three rounds. Whereas in the first round, only single mutations were incorporated, the second and third round comprised the combination of the successfully incorporated single mutations from the first round. For each round, the most important readout was the coagulant activity of the mutated FVIII variants in comparison to the non-mutated control FVIII. The approach is laid out in FIG. 1.

The DNA sequence for all FVIII variants was synthesized and cloned into a vector backbone under the control of an EF-1□ promoter. In order to reduce the size of the synthesized fragments, three additional restriction sites were integrated into the FVIII sequence by silent mutations. The sequence already had a restriction site at the beginning (HindIII) and at the end (XbaI) of the FVIII sequence, for cloning into the backbone. One additional restriction site (BamHI) occurred naturally after the removal of the B domain sequence. This led, in combination with the three restriction sites additionally incorporated (Kpnl, XmaI and EcoRI), to a FVIII molecule with six unique restriction sites. As a result, not only the sequences to be synthesized were shortened, but also a modular system that made the combination of mutations easier was made available. The FVIII molecule, derived from the sequence with the six restriction sites, was the reference molecule for all experiments performed and was called FVIII-6rs. The amino acid sequence is shown in SEQ ID NO: 2. The selection of base triplets for the new amino acids was based on a human codon usage table. The base triplet most frequently used in the human genome for an amino acid was chosen.

All mutations were tested to see if the single substitutions still lead to functional FVIII molecules. The FVIII variants containing the single mutations were produced in small-scale HEK293-F culture. The HEK293-F cells were transfected in duplicates for each FVIII construct in Nucleocuvettes. The transfected cells were cultured for 4 days. After cultivation, the supernatant, containing the FVIII, was harvested by centrifugation. The FVIII coagulant activity in the supernatant was analyzed with the chromogenic method in duplicates, as described herein. The remaining supernatant was frozen until an FVIII antigen ELISA was performed. In order to compare the coagulant activity results for different constructs from different transfection days, HEK293-F cells were additionally transfected with the reference vector, coding for FVIII-6rs. The FVIII coagulant activity for each variant was therefore not indicated in U/ml, but the relative coagulant activity was calculated, indicating the coagulant activity of the variant in relation to the FVIII-6rs of the same transfection day.

In FIG. 2, the relative coagulant activities of the single mutation variants are shown, allocated to the domains of FVIII. The analyses revealed that only eight mutations led to a total loss of FVIII coagulant activity in the cell culture supernatant. One of these, L1963Q, was a control mutation known to lead to severe Hemophilia A. Eleven mutations led to a FVIII coagulant activity in the supernatant which was below 50% of the coagulant activity of the control. Thus, in total 19 mutations were excluded from further experiments, due to low or absent FVIII coagulant activity. Nevertheless, although the 19 excluded mutations were spread over 16 immunogenic clusters, only ten immunogenic clusters had to be excluded, as further mutations were successfully incorporated in the other six clusters. The remaining 38 mutations led to FVIII variants with coagulant activities, which were at least equivalent to half of the coagulant activity of the FVIII-6rs. In addition to the coagulant activity, the antigen values of the FVIII variants and the resulting specific coagulant activities were determined (FIG. 3). As the specific coagulant activity is the ratio of FVIII chromogenic coagulant activity to FVIII antigen, 100% indicated that the amount of FVIII coagulant activity was equivalent to the amount of FVIII antigen. However, most values were above 100%. Higher values may indicate an improvement of the coagulant activity of the variants. Of the 38 active FVIII variants, 35 had specific coagulant activities of at least 100%. The three remaining variants had a specific coagulant activity below 100% but above 70%, indicating that a fraction of the produced FVIII was inactive. Five of the excluded FVIII variants revealed specific coagulant activities below 70%, whereof three had values even below 25%, indicating that most of the secreted FVIII was inactive. In contrast to that, six of the excluded variants had high specific coagulant activities above 100%, hinting towards active FVIII but a reduced secretion. All eight variants with no FVIII coagulant activity, which led to a specific coagulant activity of 0%, also revealed no FVIII antigen. This indicated that the incorporated mutations led either to no production or to no secretion of the FVIII variants.

In this first round of screening, 38 single substitutions (N79S, 180T, 1105V, S112T, L160S, L171Q, V184A, N233D, L235F, V257A, I265T, N299D, Y426H, Y430H, L505N, S507E, F555H, 161 OT, N616E, 1632T, L706N, Y748S, N754D, K1837E, R1936Q, S2030A, S2037G, N2038D, S2077G, M2123K, S2125G, F2215H, K2226Q, K2258Q, V2313A, S2315T, V2333A, Q2335H) led to a functional FVIII molecule with substantial coagulant activity (at least equivalent to half of the coagulant activity of the FVIII-6rs).

Five additional single mutations were tested (S660G, 1658T, N1796D, N2137H, 12168T). These mutations were proposed for four of the immunogenic clusters that had to be excluded in the first screening round due to non-functional mutational variants. These five mutations were originally not tested, as they had a lower calculated influence on the reduction of immunogenicity. However, analyses of the variants revealed only low or no FVIII coagulant activity in the supernatant, although the specific coagulant activities were around 100% for three of the variants. Nevertheless, the mutations were not transferred to the second round of screening, as the coagulant activities were quite low, only exceeding the 50% limit by about 10% for 1658T and N2137H.

Although all of the 38 successfully incorporated single mutations had the characteristics to be transferred to the second screening round, only one mutation for each immunogenic cluster was chosen, in order to keep the combination of the single mutations feasible. Hence, the mutation resulting in a lower FVIII coagulant activity was excluded. Additionally, mutation S2030A was found not to be part of the cluster comprising S2037G and N2038D but of a preceding cluster. As the calculated score of this cluster was already very low without the mutation, S2030A was also excluded. This led to 25 mutations, which were transferred to the second round of screening.

In a second screening round 25 out of the 38 mutations have been chosen (N79S, S112T, L160S, L171Q, V184A, N233D, I265T, N299D, Y426H, S507E, F555H, N616E, I632T, L706N, Y748S, K1837E, R1936Q, N2038D, S2077G, S2125G, F2215H, K2226Q, K2258Q, S2315T, V2333A).

In silico modelling of FVIII variants incorporating mutations was attempted, but was not successful due to lack of a complete crystal structure of FVIII having a sufficiently high resolution. The inventors chose to combine the functional single mutations in small groups to keep identify mutations, which lead to inactive protein in combination with others. For every section (defined by the restriction sites), one vector was designed containing all mutations, which led to FVIII variants with relative coagulant activities above 50%. Additionally, one vector was designed containing only the mutations that led to relative coagulant activities above 80% and reduced the immunogenicity score for the cluster by at least 15 points. For section A1A2 and A2, only one vector was constructed, as all mutations had relative coagulant activities above 80% and reduced the score by more than 15 points. Based on this, FVIII variants comprising substitutions at the following positions were produced as shown in Table 3.

TABLE 3

| Section | Number of mutations | Relative coagulant activity of single mutations | Mutations |
|---|---|---|---|
| A1 | 4 | >80% | N79S, S112T, N233D, I265T |
| A1 | 7 | >50% | N79S, S112T, L160S, L171Q, V184A, N233D, I265T |
| A1A2 | 3 | >80% | N299D, Y426H, S507E |
| A2 | 5 | >80% | F555H, N616E, I632T, L706N, Y748S |
| A3C1C2 | 6 | >80% | N2038D, S2077G, S2125G, K2258Q, S2315T, V2333A |
| A3C1C2 | 9 | >50% | R1936Q, N2038D, S2077G, S2125G, F2215H, K2226Q, K2258Q, S2315T, V2333A |

Figure 4A:
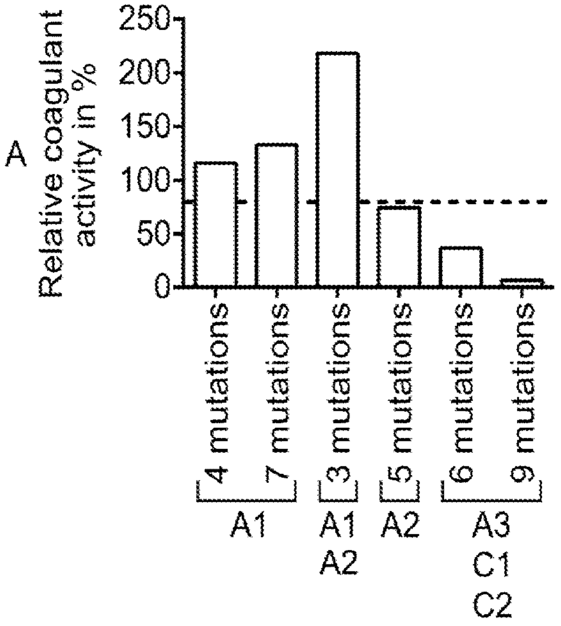
Figure 4B:
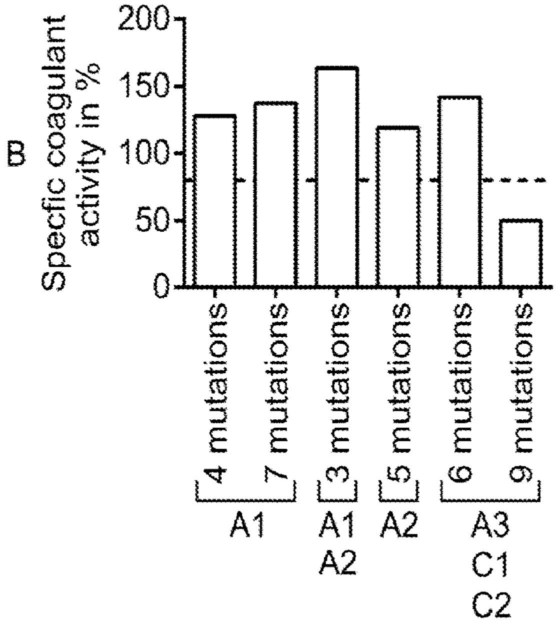

The production of the FVIII variants occurred as described for the first round. After four days of production, the FVIII coagulant activity in the cell culture supernatant was determined. Coagulant activities comparable to or even better than the control FVIII-6rs were achieved in the sections A1 and A1A2 (FIG. 4A). In particular, the combination of the three mutations in section A1A2 seemed to have a positive effect on production and/or secretion of the FVIII variant, leading to more than twice the amount of secreted, active FVIII-6rs. Due to the good coagulant activities, the seven mutations in A1 and the three mutations in A1A2 were taken to the third round. In section A2, the coagulant activity of the FVIII variant was below 80% and the two variants of the A3C1C2 section revealed coagulant activities below 40%. Due to these results, the mutations combined in A2 and A3C1C2 had to be further analyzed. The specific coagulant activities for all combinations were above 100%, indicating that the produced FVIII variants were functional, except for the variant with nine mutations in the A3C1C2 section (FIG. 4B). The low specific coagulant activity of this variant indicated that mainly inactive FVIII was secreted.

Figure 5A:
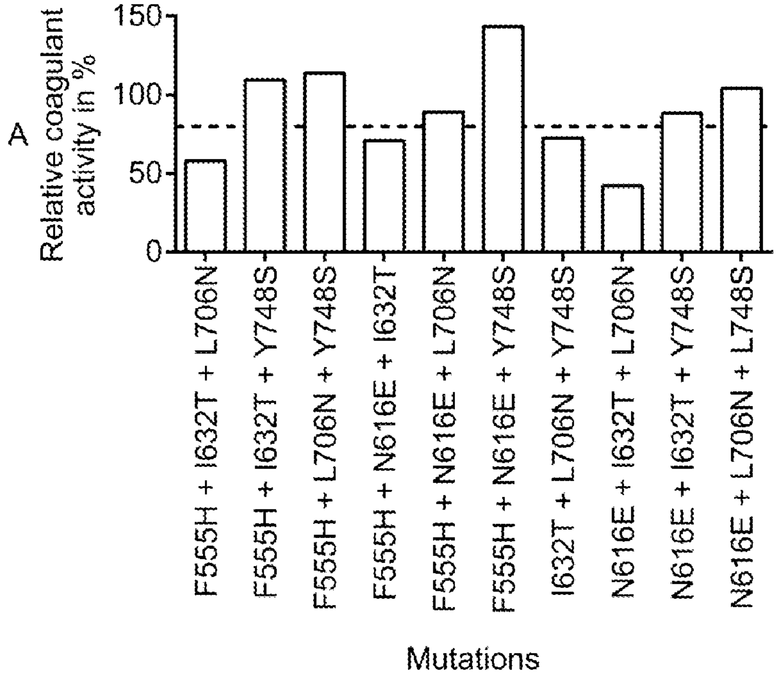
Figure 5B:
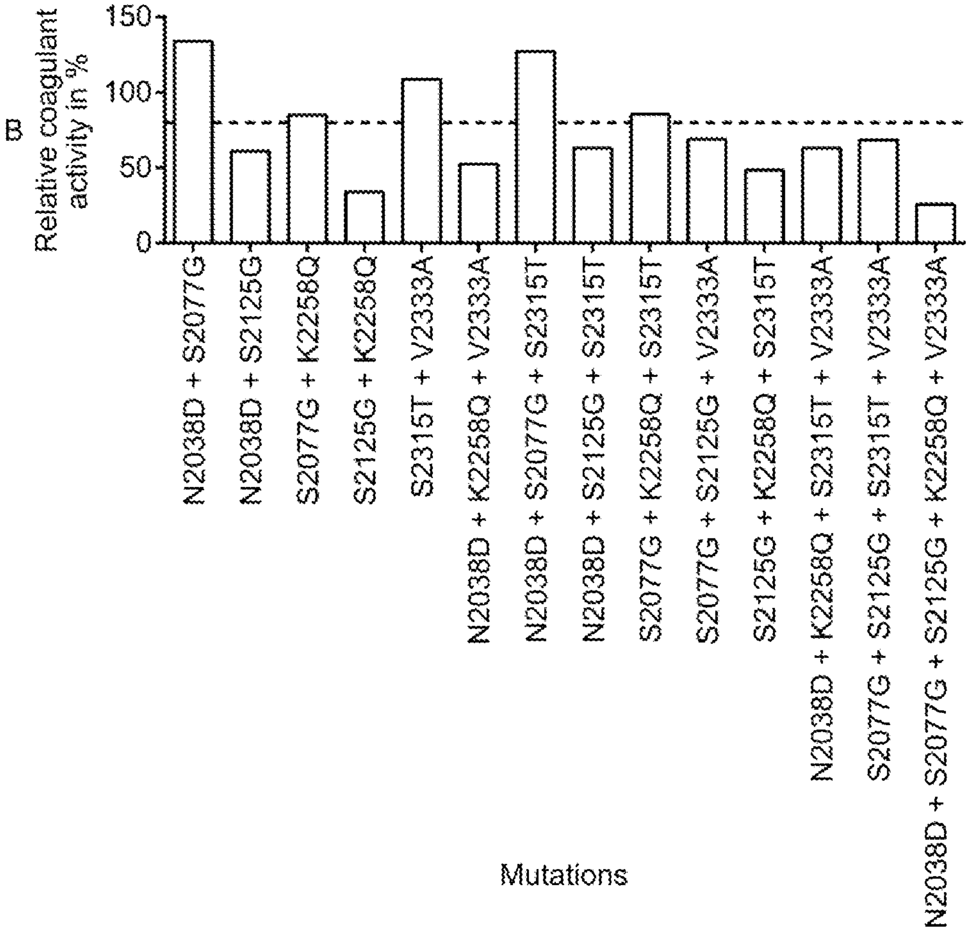

In order to detect the mutations in the A2 and A3C1C2 section which interfered with the coagulant activity of the FVIII variant, two design-of-experiment (DOE) matrices were generated. To avoid synthesis of vectors with every possible combination of the mutations, the five mutations in the A2 section were modelled in a half factorial design, whereas the six mutations in the A3C1C2 section were analyzed in an $8^{th}$ fraction fractional design. Setting aside the variants which had already been tested (single-mutant, full-mutant and naïve variant), ten vectors were designed for the A2 section and 14 vectors were designed for the A3C1C2 section. As before, the variants were produced in HEK293-F cells and the FVIII coagulant activity in the supernatant was determined. The analysis revealed that mutation 1632T in the A2 section probably was responsible for the reduced coagulant activity, as it was incorporated in all variants with coagulant activities below 100% (FIG. 5A). Said mutant is preferably not included in proteins of the invention. In the A3C1C2 section three mutations, N2038D, S2125G and K2258Q, seemed to decrease the FVIII coagulant activity (FIG. 5B). However, an obvious influence on a decreased coagulant activity was only detectable for mutation S2125G, which is preferably not included in proteins of the invention. For N2038D and K2258Q it was not clearly identifiable whether their influence might only have occurred in combination with each other or S2125G.

The specific coagulant activities of all variants in the A2 and the A3C1C2 section were at least around 100% (data not shown). This revealed that the reduced FVIII coagulant activities compared to FVIII-6rs were probably due to production or secretion problems and not due to inactive FVIII.

Based on the results from the DOE matrices one vector for the A2 section and four vectors for the A3C1C2 section were designed. The four A3C1C2 vectors omitted either only mutation S2125G, or mutation S2125G in combination with K2258Q or N2038D, or all three mutations. The incorporated mutations in the five vectors are shown in Table 4 below.

TABLE 4

| Section | Number of mutations | mutations |
|---|---|---|
| A2 | 4 | F555H, N616E, L706N, Y748S |
| A3C1C2 | 3 | S2077G, S2315T, V2333A |
| A3C1C2 | 4 (without K2258Q) | N2038D, S2077G, S2315T, V2333A |
| A3C1C2 | 4 (without N2038D) | S2077G, K2258Q, S2315T, V2333A |
| A3C1C2 | 5 | N2038D, S2077G, K2258Q, S2315T, V2333A |

The measurement of the FVIII coagulant activity in the supernatant of the HEK293-F cells, transfected with the different vectors, revealed that the coagulant activity of the variant with four mutations in the A2 section was comparable to the coagulant activity of FVIII-6rs (FIG. 6A). In contrast to that, although all four A3C1C2 variants were active, the coagulant activity of the variants comprising five mutations and four mutations without mutation N2038D revealed a reduced coagulant activity compared to FVIII-6rs. This indicates that the exclusion of mutation N2038D alone had no influence on the production or secretion of FVIII, as the coagulant activity remained low. In contrast to that, the exclusion of K2258Q led to an increase in FVIII coagulant activity. However, although not effective as a single deletion, removal of N2038D in combination with K2258Q had an additive effect and further improved the FVIII coagulant activity of the variant. Nevertheless, the combination of four mutations, still containing the N2038D, was transferred to the third round. This was due to the aim to incorporate many mutations, and accordingly, reduce immunogenicity as much as possible. Additionally, the coagulant activity results for this variant were around 100% and similar to the results for combinations in other sections. The specific coagulant activity for all variants was at least 100%, indicating that only active FVIII was present.

Finally, the second screening round led to 19 mutations, which could be combined in five sections. For section A1 and A1A2, the combination of all mutations from the first round could be included. This was not possible for the sections A2 and A3C1C2. Based on a DOE matrix one mutation had to be excluded in the A2 section, and five mutations had to be excluded in the A3C1C2 section.

Accordingly, in the second round, six additional mutations have been set aside. The last round of screening comprised a single FVIII molecule containing all 19 mutations (N79S; S112T; L160S; L171Q; V184A; N233D; I265T; N299D; Y426H; S507E; F555H; N616E; L706N; Y748S; K1837E; N2038D; S2077G; S2315T; V2333A) remaining from screening round 1 and 2. This mutated FVIII variant was shown to be functional in coagulation, and comprises a high number of single substitutions which renders the molecule less immunogenic.

Due to the incorporation of the 19 mutations into the FVIII sequence, the initial immunogenicity score of FVIII-6rs of 7.01 was reduced to −10.55 for FVIII-19M. The immunogenicity score indicates the immunogenicity of the protein of interest in relation to a protein with a random sequence. The immunogenicity score of the random protein is set to 0. In order to be able to compare the scores for different proteins of different length, the score is given per 1000 of the 9-mers to which a protein is split for in silico analysis. Exemplary immunogenicity scores of other proteins are about 23 for Tetanus Toxin, 10.03 for Refacto AF®, about −10 for albumin, or about −42 for an IgG Fc region.

As the A3C1C2 section revealed to be mostly influenced by the incorporation of mutations, an additional vector was designed with no mutations in section A3C1C2 (FVIII-15M), in order to compare the coagulant activities. This led to two proteins comprising in total 15 (FVIII-15M, SEQ ID NO: 7) and 19 mutations (FVIII-19M, SEQ ID NO: 5). For both vectors, the analysis of the FVIII coagulant activity in the supernatant revealed coagulant activities at least comparable to FVIII-6rs. The variant with the 15 mutations was secreted in a higher concentration of active FVIII compared to the one with the 19 mutations. The specific coagulant activities were nearly 100% for the FVIII-15M and above 100% for FVIII-19M.

A further variant does not comprise a substitution at position K1837 such as the K1837E substitution, which appears to reduce coagulant activity, but comprises the other substitutions of FVIII-19M. This variant is designated FVIII-18M. It has about the same specific coagulant activity as FVIII-19M, but a higher chromogenic coagulant activity when measured in the supernatant. It can be concluded that the K1837E substitution may reduce production, folding or secretion of FVIII to a certain extent. However, the coagulant activity of FVIII-18M with regard to the clotting assay is also improved, so the substitution may also otherwise reduce coagulant activity. Nevertheless, further assays described below show that FVIII-19M can be therapeutically used.

Further advantageous variants were produced, e.g., a FVIII protein FVIII-GOF1 with the substitutions L171Q, S507E, Y748S and V2333A; and FVIII-GOF2 with the substitutions L171Q, N299D, N616E and V2333A. These variants incorporate substitutions in the different regions showing the best results regarding coagulant activity and specific coagulant activity. The following variants incorporate the substitutions with the best results regarding reduction of the immunogenicity score: FVIII-LS1 with the substitutions S112T, S507E, Y748S, K1837E and N2038D; and FVIII-LS2 with the substitutions S112T, Y426H, N754D, K1837E and N2038D. Of note, the substitutions S507E and Y748S are highly advantageous with regard to both aspects. Preferred proteins of the invention thus at least comprise said substitutions, as well as optionally, L171Q and V2333A. It is further optimal for reducing immunogenicity to incorporate all seven preferred substitutions in the A1 region.

FIG. 7 summarizes chromogenic coagulant activity, clotting coagulant activity and specific coagulant activity of different Factor VIII proteins according to the invention, wherein all constructs have been produced in HEK293-F cells, with the analysis performed in the supernatant of the cells. The measured relative coagulant activities are given in percentage based on the coagulant activity of FVIII-6rs, which was always produced and tested in parallel. Specific coagulant activities are based on the ratio of chromogenic coagulant activity detected to antigen detected in the supernatant by an ELISA as described below.

For further experiments, the constructs FVIII-19M and FVIII-6rs have been produced in CAP-T cells, resulting in higher protein masses. Further on, FVIII-19M and FVIII-6rs were purified from the cell culture supernatant.

Different analyses of the FVIII-19M in comparison to FVIII-6rs, ReFacto AF® and NUWIQ® were performed using SDS-PAGE and Western Blot. The blot revealed that FVIII-19M and FVIII-6rs were mainly produced as single chain proteins, in comparison to the two commercially available products, which are mainly double chain FVIII. This difference may be due to the different cell lines used for production. Two additional Western Blots revealed that FVIII-19M and FVIII-6rs are glycosylated and sulfated, confirming that the post-translational modifications took place in the CAP-T cells. However, no detailed conclusion could be drawn on whether all six tyrosines were sulfated and which glycosylation patterns were added.

The clotting time for the different FVIII products was determined using the ROTEM method. During this analysis, the clotting time of plasma is analyzed depending on the amount and the functionality of the applied FVIII. The FVIII products were added to FVIII-deficient plasma and the clotting was initiated via the intrinsic pathway. The time until a clot was starting to form was measured. By adding different concentrations of FVIII, an increase of the clotting time was detected in correlation to decreasing concentrations of FVIII. When comparing the different products, ReFacto AF® (Pfizer Inc., produced in CHO cells) and NUWIQ® (Octapharma AG, produced in HEK cells), which are both B-domain deleted, revealed very similar clotting times, whereas the clotting times were slightly prolonged for FVIII-6rs and even more for FVIII-19M (FIG. 8). However, all clotting times only varied between 120 seconds and 160 seconds at 1 U/ml FVIII, which was still in the normal clotting time range of 100-240 seconds in healthy people.

In a thrombin generation assay (FIG. 9), FVIII-6rs resembled ReFacto AF® and NUWIQ® regarding the amount of generated peak thrombin and the time to peak thrombin generation but showed a slightly reduced area under the curve. FVIII-19M revealed significantly lower results for generated peak thrombin, area under the curve and time needed to reach peak thrombin generation, especially compared to ReFacto AF® and NUWIQ®. However, these results were comparable with the ROTEM results, revealing a slightly prolonged clotting time for FVIII-19M.

The binding potency of FVIII-19M and FVIII-6rs to vWF was determined in an ELISA based approach. ReFacto AF® was used as a reference, and the potency of the binding of ReFacto AF® to vWF was set to 1. All other potencies were calculated in relation to ReFacto AF®. The data revealed that the vWF binding was similar for ReFacto AF® and NUWIQ® but impaired for FVIII-6rs and FVIII-19M (FIG. 10). However, the only significant difference could be detected between NUWIQ® and FVIII-19M. The reduced binding, also of FVIII-6rs, might be due to different post-translational modifications made by the CAP-T cells. This could be correlated with the reduced sulfation detected in the heavy and light chain in the Western Blot. Missing sulfation might have influenced vWF binding, as especially the sulfation at Y1683 is important for the binding of vWF. However, decreased sulfation cannot be the only reason for the reduced vWF-binding, as ReFacto AF® revealed nearly no sulfation on the Western Blot, but good vWF-binding. The reduction in the potency of FVIII-19M in comparison to FVIII-6rs might thus be due to additional structural changes, derived from incorporated mutations, influencing the vWF binding.

The slightly lower coagulant activity of FVIII-19M in the experiments done with regard to clotting time, thrombin generation and binding to vWF may at least in part be explained by the lower coagulant activity as measured in the clotting assay compared to the chromogenic assay, as the chromogenic assay may particularly overestimate the coagulant activity of FVIII-19M (FIG. 11).

Immunogenicity of proteins of the invention was analyzed with two different approaches:

Immunogenicity Score

The reduced immunogenicity of the FVIII molecule with 19 single point mutations was evaluated by an in silico method of calculation. The initial immunogenicity score of the molecule without mutations of about 7 was reduced to about −11 for the FVIII molecule with 19 single point mutations. The immunogenicity scores were calculated in relation to a protein with a randomized sequence of the same length as the analyzed FVIII.

The immunogenicity score, which indicates the immunogenic potential of a protein, was calculated using EpiVax's EPIMATRIX System. In order to be able to compare the immunogenicity score of the protein of interest to the scores of other proteins, it is correlated to the score of a protein with a randomized amino acid sequence. The immunogenicity score of this "average" protein is set to zero. Additionally, the immunogenicity score is indicated per 1000 peptides, each peptide comprising nine amino acids. Due to this, proteins of various length can be compared. Immunogenicity scores above zero indicate the presence of excess MHC class II ligands and denote a higher potential for immunogenicity while scores below zero indicate the presence of fewer potential MHC class II ligands than in a random protein and a lower potential for immunogenicity. Proteins scoring above +20 are considered to have a significant immunogenic potential.

In Vitro Immunogenicity Assay

An in vitro T cell assay for analyzing the immunogenicity of a protein of interest, such as FVIII, was established, which is based on dendritic cells (DC) and regulatory T-cell-depleted $CD4^+$ T cells of healthy donors and stimulation with the protein of interest.

The recombinant molecule FVIII-19M according to the invention was shown to be less immunogenic by the in vitro immunogenicity T cell assay compared to the FVIII molecule without mutations.

The in vitro assay is able to determine whether less T cells become activated, due to a reduced presentation of FVIII-19M peptides on the surface of DCs. The assay includes DCs, derived from monocytes, and $CD4^+CD25^-$ T cells. The $CD4^+CD25^+$ T cells were depleted prior to co-cultivation, as this subpopulation mainly comprises regulatory T cells. This was important, because the T cell population derived from healthy donors as well as tolerant Hemophilia A patients was expected to contain regulatory T cells suppressing the FVIII-specific T cells which were not depleted during ontogeny (Kamate, C., Lenting, P. J., van den Berg, H. M. & Mutis, T. Depletion of CD4+/CD25 high regulatory T cells may enhance or uncover factor VIII-specific T-cell responses in healthy individuals. *Journal of Thrombosis and Haemostasis* 5, 611-613 (2007)). As the aim of the assay was to stimulate the FVIII-specific T cells, the regulatory T cells were depleted. The approach of using DCs as APCs was chosen due to two reasons. On the one hand, the focus was on the activation of $CD4^+$ T cells based on the interaction with the presented FVIII epitopes. Influences due to interaction with other immune cells might have distorted the results. On the other hand, the assay may also be performed with cells derived from Hemophilia A patients. These patients, especially previously untreated Hemophilia A patients, may still have naïve T cells, and the activation of naïve T cells primarily occurs by DCs.

As illustrated in FIG. 13, monocytes were purified from thawed PBMCs and differentiated to immature DCs (iDCs) using IL-4 and GM-CSF, e.g., in 5 days. The cells were stimulated, e.g., for 1 day with cytokines (e.g., an IL-Mix as defined below) and antigen, e.g., the FVIII of interest, in order to obtain mature DCs (mDCs). The $CD4^+CD25^-$ T cells were purified from PBMCs two days prior to the co-cultivation with the mDCs. After the purification, the $CD4^+CD25^-$ T cells were labelled with CFSE (Carboxyfluorescein diacetate succinimidyl ester) and cultured for 2 days in presence of IL-2, in order to recover from the purification and labeling process. mDCs and labelled $CD4^+CD25^-$ T cells were co-cultivated, e.g., for 9 days. The T cells were harvested and analyzed by flow cytometry.

The DC-T cell assay was performed with the FVIII-19M and FVIII-6rs. The cells were purified from PBMCs of healthy donors. The DCs were stimulated after differentiation either with the previously determined IL-Mix alone or with the IL-Mix and additional protein. The additional protein was ReFacto AF® as a positive control for FVIII-specific T cell proliferation and FVIII-6rs and FVIII-19M as the proteins of interest. The concentration of the FVIII products was 15 U/ml, in order to ensure that enough FVIII was present. The co-cultivation was done in 48-well plates, leading to a DC:T cell ratio of at least 1:10. All cells were analyzed by flow cytometry after their purification, in order to ensure purity, and the T cells were analyzed prior to co-cultivation, in order to exclude pre-activation, and after 9 days of co-cultivation. The results from the flow cytometric analyses of the T cells after 9 days of co-cultivation were further analyzed. The proliferation of all $CD4^+$ T cells was determined for every approach.

In total, 23 different healthy donors were analyzed. For the final analysis donors revealing a higher T cell response to DCs only treated with the IL-Mix than with the IL-Mix and FVIII, and donors showing a markedly varying viability of T cells when stimulated with different FVIII proteins were excluded. As not all healthy people possess T cells against FVIII, it was expected that not all healthy donors react to FVIII. Based on this selection, the results of 10 healthy donors were analyzed.

FIG. 14 displays the difference between the $CD4^+$ T cell proliferation to DCs stimulated with IL-Mix plus FVIII-19M and the $CD4^+$ T cell proliferation to DCs stimulated with IL-Mix plus FVIII-6rs. Results below 0 indicate a reduced T cell response to FVIII-19M compared to FVIII-6rs. This reduced response was detected in most donors. However, results above 0 were detected in a minority of donors. Even though, the differences in proliferation were below 10% for these donors, whereas higher differences were detected in the group of donors showing a reduced response to FVIII-19M. Altogether, the amount of donors revealing a reduced response to FVIII-19M was larger, leading to a significant reduction in $CD4^+$ T cell proliferation to DCs stimulated with IL-Mix and FVIII-19M. These results from the in vitro DC-T cell assay confirmed a reduced $CD4^+$ T cell proliferation in response to the de-immunized FVIII variant containing the 19 amino acid mutations.

In Vitro Stability

The recombinant FVIII protein of the invention was incubated in FVIII-deficient plasma at 37° C., and coagulant activity was analyzed after different time periods, in comparison to ReFacto AF®, NUWIQ® and FVIII-6rs. As shown in Table 5, the loss of coagulant activity was acceptable for all analyzed proteins.

TABLE 5

Chromogenic coagulant activity of FVIII proteins incubated in FVIII-deficient plasma at 37° C.

| FVIII product | Hours | Chromogenic coagulant activity in U/ml |
|---|---|---|
| ReFacto AF ® | 0 | 1.01 |
| | 4 | 1.06 |
| | 8 | 1.02 |
| | 24 | 0.98 |
| NUWIQ ® | 0 | 1.10 |
| | 4 | 1.14 |
| | 8 | 1.14 |
| | 24 | 1.07 |
| FVIII-19M | 0 | 1.04 |
| | 4 | 0.92 |
| | 8 | 0.91 |
| | 24 | 0.87 |
| FVIII-6rs | 0 | 1.09 |
| | 4 | 1.04 |
| | 8 | 1.00 |
| | 24 | 0.99 |

Methods

In Silico Analyses

In silico T cell epitope-modelling (EPIMATRIX tools) was applied in order to identify MHC class 11-binding peptides, cluster the results, to compare the clusters to other proteins and to predict amino acid exchanges.

The modelling tools used for the in silico analyses are commercially available from EpiVax (Providence, RI, USA). The tools analyze protein sequences, in order to find peptides binding to the MHC class II. These peptides are further analyzed regarding potential amino acid exchanges, in order to reduce this binding.

The FVIII molecule used for the modelling process was a B domain deleted Factor VIII molecule (BDD FVIII) in which 818 amino acids of the B domain are deleted (FVIII-6rs, SEQ ID NO: 2). The modelling process comprised four steps. In the first step, the EPIMATRIX tool split the protein into peptides, consisting of nine amino acids, so-called 9-mers. This is due to the fact that the core binding region of the MHC class II comprises nine amino acids. The sequence of a 9-mer and its following 9-mer overlap by eight amino acids. By building these highly overlapping 9-mers, no potential binding peptides were lost. The binding capacity of all 9-mers was tested against eight common HLA class II supertype alleles (DRB1*0101, DRB1*0301, DRB1*0401, DRB1*0701, DRB1*0801, DRB1*1101, DRB1*1301, DRB1*1501), covering over 90% of the human population (De Groot, A S, MCMURRY, J. & MOISE, L. Prediction of immunogenicity: in silico paradigms, ex vivo and in vivo correlates. *Current Opinion in Pharmacology* 8, 620-626 (2008); Moise, L. et al. Effect of HLA DR epitope de-immunization of Factor VIII in vitro and in vivo. *Clinical Immunology* 142, 320-331 (2012)). The potential of each 9-mer to bind a HLA allele was indicated by a "Z score". This score indicated the strength of binding, normalized to the frequency of the given allele in the population (De Groot, Anne S. & Martin, W. Reducing risk, improving outcomes: Bioengineering less immunogenic protein therapeutics. *Clinical Immunology* 131, 189-201 (2009)). A 9-mer with a high Z-score for at least four HLA alleles was regarded as highly immunogenic and called an EpiBar (Weber, C. A. et al. T cell epitope: Friend or Foe? Immunogenicity of biologics in context. *Advanced Drug Delivery Reviews* 61, 965-976 (2009)).

In the following step, overlapping EpiBars were clustered using the program ClustiMer (Moise, L. et al. Effect of HLA DR epitope de-immunization of Factor VIII in vitro and in vivo. *Clinical Immunology* 142, 320-331 (2012)). This analysis led to EpiBar clusters of up to 25 amino acids, binding to class II MHCs derived from multiple HLA alleles. Previous to the optimization of these clusters, an analysis regarding similarity with other endogenous proteins was performed using the program JanusMatrix. A sequence overlap with at least two other endogenous proteins led to the exclusion of the cluster from further modification, because central tolerance is very likely established to common endogenous peptides. In addition to that, clusters comprising cleavage sites, activation sites or other sites important for the activity of FVIII were set aside and were not altered. In the last step, amino acid exchanges were calculated using OptiMatrix. This tool evaluated the contribution of each amino acid of an identified cluster to the binding to the MHC class II (Moise, L. et al. Effect of HLA DR epitope de-immunization of Factor VIII in vitro and in vivo. *Clinical Immunology* 142, 320-331 (2012)). Afterwards, OptiMatrix calculated which amino acid substitutions reduced the binding affinity to the MHC class II (De Groot, Anne S. & Moise, L. Prediction of immunogenicity for therapeutic proteins: State of the art. *Current Opinion in Drug Discovery & Development* 10, 1-9 (2007)). These optimizations were based on the principles that the amino acid exchanges had to be conservative, preferably occurred in other species and were not registered in the database comprising all known FVIII mutations leading to Hemophilia A (Kemball-Cook, G., Tuddenham, Edward G. D. & Wacey, A. I. The Factor VIII Structure and Mutation Resource Site: HAMSTeRS Version 4. *Nucleic Acids Research* 26, 216-219 (1998)).

Analysis of Mutations

By in silico results recommended amino acid exchanges were incorporated into the FVIII sequence. Each mutation of the factor VIII molecule was screened for FVIII coagulant activity. In the first round single mutations were incorporated. The second and third round comprised the combination of the successfully incorporated single mutations from the first round. Reference molecule was FVIII-6rs with six unique restriction sites. The single mutations (first round) and the combinations of mutations (second and third round) have been analyzed after production (transient transfection) in human cell lines (HEK293-F), wherein the produced and secreted protein was analyzed in the cell culture supernatant. FVIII coagulant activity was analyzed by chromogenic and clotting methods. Antigen values were analyzed by FVIII antigen ELISA. The specific coagulant activities were calculated as the relation of coagulant activity to antigen.

In the first round, from 57 recommended mutations, 19 mutations were excluded due to low or absent FVIII coagulant activity. The remaining 38 mutations led to FVIII variants with coagulant activities of at least equivalent to half of the coagulant activity of the reference molecule. For the second round, 25 mutations were chosen, only one mutation for each immunogenic cluster. Combinations of mutations combined in sections (defined by restriction sites) were analyzed (relative and specific coagulant activity). Further analysis was done based on DOE matrices.

Large scale production of the recombinant proteins was done in CAP-T cells by transient transfection and subsequent purification (SAEx—strong anion exchange chromatography—alternatively TFF—tangential flow filtration, AC—FVIII affinity chromatography, buffer exchange via SEC—size exclusion chromatography).

Further analysis was done regarding posttranslational modifications and functionality (Western Blots detecting FVIII heavy and light chain, thrombin cleavage, glycosylation and sulfation, 2D-DIGE and functional assays ROTEM, TGA and vWF-FVIII ELISA).

The reduced immunogenicity of the recombinant proteins according to the invention was confirmed in silico and in vitro (DC-T cell assay).

Transfection

For transient transfection, eukaryotic cell systems, namely CAP-T cells and HEK cells, were used. CAP cells are an immortalized cell line based on primary human amniocytes and grow in suspension. CAP-T cells are based on the original CAP cells and additionally express the large T antigen of simian virus 40. CAP-T cells are especially useful for transient transfection. Moreover, the HEK 293-F cell line was used for transient transfection. The HEK 293-F cell line is derived from the original HEK 293 cell line and is adapted to suspension growth in serum-free medium. The HEK cells were used for the small scale production of various mutated FVIII variants.

Transient transfection was done by electroporation using the commercially available 4D-Nucleofector system (Lonza Group Ltd., Basel). Electroporation was performed with $7 \cdot 10^6$ HEK293-F cells and 7 μg FVIII plasmid in a volume of 100 μl. $1 \cdot 10^7$ CAP-T cells were used for transfection with 5 μg FVIII plasmid in a volume of 100 μl. After transfection, the cells were incubated for 4 days. The cells and the supernatant were used for further analysis.

Protein Purification

FVIII-6rs and FVIII-19M was produced in CAP-T cells in up to 800 ml scales. Purification occurred directly from the cell culture supernatant by FPLC. The first step was either a tangential flow filtration or an ion exchange chromatography, using the strong anion exchange columns HiTrap Capto Q (GE Healthcare Europe GmbH, Freiburg). In this step the sample was concentrated, host cell proteins were lost and the buffer was exchanged. The fractions containing the eluted protein were determined according to the chromatogram. The second step was an affinity chromatography, using a column packed with the commercially available VIIISelect resin (GE Healthcare Europe GmbH, Freiburg). The fractions containing the eluted FVIII were determined according to the chromatogram. The last step was a buffer exchange to FVIII Formulation Buffer by size exclusion chromatography, using the HiTrap Desalting columns (GE Healthcare Europe GmbH, Freiburg). The fractions containing FVIII were determined according to a high UV peak and a stable conductivity peak in the chromatogram. After purification, the FVIII products were concentrated via spin columns (Merck Millipore, Darmstadt) with a molecular weight cut-off of 10 kDa. All columns were run under the conditions specified by the manufacturer.

Analytics

Chromogenic and Clotting Assays

FVIII coagulant activity was either determined with the chromogenic or the clotting method. In the chromogenic assay, the FVIII sample is added to FVIII-deficient plasma. Additionally the preparation contains FIXa, FX, phospholipids and calcium chloride. FVIIIa, FIXa and FX form the tenase complex and FX is activated to FXa. The rate of FX activation is dependent on the amount of active FVIII. Afterwards, a substrate is added which is hydrolyzed by FXa. The hydrolyzed substrate is chromogenic and absorbance is measured at 405 nm. Based on a standard curve, the amount of active FVIII can be determined. In contrast to the chromogenic method in which only a part of the clotting cascade takes place, the whole clotting cascade takes place in the clotting method, starting from the activation of FXI to the generation of a clot. The preparation contains the FVIII sample in FVIII-deficient plasma, calcium chloride and an activator. The time needed to form a clot is measured. Based on a standard curve, the amount of active FVIII can be determined.

Both tests were performed fully automatically by the BCS XP (Siemens Healthineers, Erlangen) according to the manufacturer's instructions. The reagents for the chromogenic method were derived from the Coatest SP FVIII Kit (Chromgenix, Haemochrom Diagnotica GmbH, Essen). Additionally, a Tris-BSA (TBSA) Buffer, containing 25 mM Tris, 150 mM sodium chloride (NaCl) and 1% Bovine serum albumin (BSA), and water were needed for dilution. All reagents and the sample were put into the BCS XP. The activator Actin FSL for the initiation of the clotting assay is commercially available from Siemens (Siemens Healthineers, Erlangen). Additionally, this test requires calcium chloride (Siemens Healthineers, Erlangen) and the TBSA buffer. As for the chromogenic assay, all reagents and samples were put into the BCS XP (Siemens Healthineers, Erlangen). For both assays, all required pipetting, diluting, incubation and measurement steps were performed by the BCS XP. The samples for both assays were at least diluted 1:2 in FVIII-deficient plasma (Siemens Healthineers, Erlangen). The standard curves for the tests were generated with a biological reference preparation (BRP) (edqm. Straβbourg). The activity of the BRP is indicated in IU/ml. However, 1 U/ml can be assumed to be equivalent to 1 IU/ml.

ELISA

The FVIII antigen amount was determined using the commercially available Asserachrom VIII:Ag ELISA Kit (Stago, Dusseldorf). In this kit, an anti-FVIII F(ab') is coated to the wells. The sample is added to the wells and is detected after binding by an anti-FVIII IgG coupled to a peroxidase. Using TMB and sulfuric acid a color reaction takes place due to the reaction between the peroxidase and the TMB. The absorbance can be measured at 450 nm. FVIII samples were diluted, based on their coagulant activity, to concentrations fitting to the calibration curve. The ELISA was performed according to the manufacturer's protocol and the absorbance was measured using a plate reader.

For the detection of the binding of the FVIII constructs to vWF, another ELISA was performed. In this case, vWF was coated to the wells of a 96-well plate at a concentration of 0.1 U/ml. Afterwards the FVIII variants were applied at a concentration of 0.25 U/ml. ReFacto AF® was used as a reference. Each sample was further on diluted 1:2 in buffer. A total of 7 serial dilutions were performed. In order to detect bound FVIII, the reagents from the Coatest SP FVIII Kit (Chromgenix, Haemochrom Diagnotica GmbH, Essen), also used for the chromogenic coagulant activity measurement, were used. At first, FIXa, FX and phospholipids were added to the wells. After an incubation time of 5 minutes, calcium chloride was added. This was incubated again for 5 minutes. In the last step, the chromogenic substrate was added. After addition of the substrate, the plate was immediately put into a plate reader and the development of the chromogenic substrate was measured at 405 nm for 490 seconds. The generated curves were analyzed using the PLA 3.0 software. Potencies of vWF-binding of the different FVIII products were calculated in relation to ReFacto AF®.

Western Blots

For Western Blotting, protein samples were separated via reducing SDS-PAGE with Bis-Tris gels in a MOPS Buffer system. The applied FVIII solutions had a maximum concentration of 10 U/ml based on FVIII coagulant activity. The proteins from the gel were blotted onto nitrocellulose membranes. The membranes were blocked overnight at 4° C. The primary antibodies for detection of FVIII were either a polyclonal sheep anti-human Factor VIII antibody detecting heavy and light chain (Cedarlane, Burlington) or a monoclonal rabbit anti-human FVIII antibody detecting only the heavy chain (Sino Biological Inc., Wayne) and a monoclonal mouse anti-human FVIII antibody detecting the light chain (Merck Millipore, Darmstadt). The secondary antibodies were either coupled to IRDye 800CW (LI-COR Biotechnology GmbH, Bad Homburg), IRDye 680RD (LI-COR Biotechnology GmbH, Bad Homburg) or CF680 (Biotium Inc., Fremont), leading to fluorescence signals detectable with the Odyssey scanner. Primary and secondary antibodies were incubated for one hour each, on a shaking platform at room temperature.

For the detection of sulfotyrosines, a mouse anti-human sulfotyrosine antibody (Merck Millipore, Darmstadt) was used. The secondary antibody was a donkey anti-mouse antibody coupled to IRDye 800CW. Preparation was performed as described above.

In order to determine whether the FVIII variants can be activated by thrombin, the samples were incubated with 10 U/ml thrombin for 8 minutes at 37° C. prior to the SDS-PAGE and Western Blot. SDS-PAGE and Western Blot were performed as described above. The primary antibody for the detection of FVIII in the Western Blot was the polyclonal sheep anti-human Factor VIII antibody (Cedarlane, Burlington) detecting heavy and light chain and a secondary donkey anti-sheep antibody coupled to IRDye 8000W (LI-COR Biotechnology GmbH, Bad Homburg).

Functional Assays

In the Thrombin Generation Assay (TGA), the amount of generated thrombin is measured. The clotting cascade takes place, started via the extrinsic pathway by tissue factor. The thrombin finally generated cleaves a fluorogenic substrate which can be measured at 460 nm. The assay was performed with FVIII diluted in FVIII-deficient plasma. FVIII concentrations up to 0.25 U/ml were analyzed. TGA reagent C low and TGA substrate, both commercially available by Technoclone (Vienna), were added to each sample well referring to the manufacturer's protocol. TGA reagent low consist of low concentrations of phospholipid micelles containing recombinant human tissue factor, in order to initiate the clotting cascade. The substrate is the fluorogenic substrate finally cleaved by the generated thrombin. The reaction was performed at 37° C. in a plate reader and the development of the fluorogenic substrate was measured for two hours. In addition to the samples, a calibration curve was measured using the TGA Cal Set, also available by Technoclone (Vienna). The amount of generated thrombin was calculated based on the calibration curve. Additionally, the area under the curve and the time to maximum thrombin generation was calculated based on the first deviation of the generated curve.

The Thromboelastometry (TEM), using the ROTEM system (Tem International GmbH, Munich), was also used to determine the functionality of the FVIII variants. In this method, the sample is applied to a cup and a pin is set into the middle of the cup. The sample lies in the space between cup and pin. The pin rotates and its rotation is monitored by a light beam, which is reflected from the pin onto a detector. Upon the onset of coagulation, the generated clot restricts the movement of the pin up to a maximum when the final clot is formed. In contrast to the TGA, the clotting was initiated via the intrinsic pathway in the ROTEM system, using the in-tem reagents, commercially available by Tem International GmbH (Munich). FVIII concentrations between 1 U/ml and 0.01 U/ml, based on the chromogenic coagulant activity, were analyzed. The reagents were used as described in the manufacturer's protocol. The measurement and calculations were performed fully automated by the ROTEM system. Finally, clotting times were determined.

In Vitro DC-T Cell Assay

The DCs and T cells for the in vitro assay were derived from PBMCs of healthy donors. The PBMCs were purified from either leukapheresis products or whole blood donations of healthy donors via a den-sity gradient using Lymphoflot (Bio-Rad Laboratories GmbH, München). The PBMCs were cryopreser-ved at −150° C. until used for the assay. Monocytes as well as $CD4^+CD25^-$ T cells were purified with the MACS technology commercially available from Miltenyi Biotec (Miltenyi Biotec GmbH, Bergisch Gladbach). For the monocyte purification CD14 MicroBeads were used, whereas the $CD4^+CD25^+$ Regulatory T Cell Isolation Kit (Miltenyi Biotec GmbH, Bergisch Gladbach) was used for the T cell purification. For monocytes, purification occurred according to the manufacturer's protocols.

For the purification of the $CD4^+CD25^-$ T cells, the two-step purification process recommended in the manufacturer's protocol was combined in one step performing the negative selection of $CD4^+$ T cells and the positive selection of $CD25^+$ cells in parallel and using only one purification column. Used amount of antibodies were according to the protocol and incubation times according to the negative selection step. Monocytes were the first cells to be purified during the assay. After purification, the monocytes were plated at $1 \cdot 10^6$ cells/ml in X-VIVO 15 medium (Lonza Group Ltd., Basel). In order to differentiate the monocytes to DCs, a final concentration of 4000 U/ml Granulocyte-macrophage colony-stimulating factor (GM-CSF) and 1250 U/ml Interleukin (IL)-4 (PeproTech, Hamburg) were added to each well. The monocytes were cultured for five days at 37° C. After 4 days the purification of the CD4+CD25− T cells took place. After purification the T cells were labeled with CFSE (BioLegend, Koblenz) according to Quah et al., Nature Protocols, 2007. Afterwards the purified T cells were plated in a final concentration of $2 \cdot 10^6$ cells/ml in X-VIVO-15. IL-2 (PeproTech, Hamburg) was added to the cell suspension in a final concentration of 20 U/ml. The T cells were cultured at 37° C. for 2 days. 24 hours before starting the co-cultivation of DCs and $CD4^+CD25^-$ T cells, the DCs were stimulated with an IL-Mix consisting of 10 ng/ml IL-1β, 10 ng/ml IL-6 and 10 ng/ml Tumor necrosis factor (TNF)-α (Miltenyi Biotec GmbH, Bergisch Gladbach) with or without 15 U/ml FVIII. The next day, the T cells were harvested and the cell count was determined. The T cell concentration was set to $2 \cdot 10^6$ cells/ml in fresh X-VIVO 15. The supernatant in the wells containing the DCs was carefully removed in order not to disturb the DCs. T cell suspension was applied to the DC wells, in order to reach a DC:T cell ratio of at least 1:10. The amount of T cell suspension added was dependent on the size of the well in which the DCs were originally plated. No additional cytokines were added to the medium. The cells were co-cultivated for 9 days at 37° C. Afterwards the T cells were harvested and analyzed by flow cytometry regarding proliferation.

The invention claimed is:

1. A recombinant Factor VIII protein comprising at least three amino acid substitutions at positions selected from the group consisting of Y748, L171, S507, N79, I80, I105, S112, L160, V184, N233, L235, V257, I265, N299, Y426, Y430, L505, F555, I610, N616, I632, L706, N754, K1837, R1936, S2030, S2037, N2038, S2077, M2123, S2125, F2215, K2226, K2258, V2313, S2315, V2333 and Q2335;

wherein substitutions of N are independently selected from the group consisting of D, H, S and E; wherein substitution of I are independently selected from the group consisting of T and V; wherein substitutions of S are independently selected from the group consisting of A, N, G, T and E; wherein substitutions of L are independently selected from the group consisting of N, Q, F and S; wherein substitutions of V are independently selected from the group consisting of A and T; wherein substitutions of Y are independently selected from the group consisting of N, H and S; wherein substitutions of F are independently selected from the group consisting of H and S; wherein substitutions of K are independently selected from the group consisting of N, D, E, Q, S and T; wherein substitutions of R are independently selected from the group consisting of Q, H and S; wherein substitutions of M are selected from the group consisting of R, Q, K and T; and/or wherein substitutions of Q are selected from the group consisting of R, D, E, H and K;

wherein the positions are specified in relation to full length human Factor VIII molecule of SEQ ID NO: 1;

and wherein the recombinant Factor VIII protein retains at least 50% coagulant activity, as determined in a chromogenic assay, compared to a Factor VIII protein consisting of SEQ ID NO: 2, or a fusion protein of said recombinant Factor VIII protein.

2. The recombinant Factor VIII protein of claim 1, wherein the amino acid substitutions are selected from the group consisting of Y748S, L171Q, S507E, N79S, 180T, I105V, S112T, L160S, V184A, N233D, L235F, V257A, I265T, N299D, Y426H, Y430H, L505N, F555H, I610T, N616E, I632T, L706N, N754D, K1837E, R1936Q, S2030A, S2037G, N2038D, S2077G, M2123K, S2125G, F2215H, K2226Q, K2258Q, V2313A, S2315T, V2333A and Q2335H.

3. The recombinant Factor VIII protein of claim 1, wherein the recombinant Factor VIII protein comprises 3-25 of said substitutions and the substitutions are located within different immunogenic clusters.

4. The recombinant Factor VIII protein of claim 1, comprising at least three amino acid substitutions at positions selected from the group consisting of Y748, L171, S507, N79, S112, L160, V184, N233, I265, N299, Y426, F555, N616, I632, L706, K1837, R1936, N2038, S2077, S2125, F2215, K2226, K2258, S2315, and V2333.

5. The recombinant Factor VIII protein of claim 1, comprising amino acid substitutions at least at positions a) N79S, S112T, N233D, and I265T; and/or
b) N79S, S112T, L160S, L171Q, V184A, N233D, and I265T; and/or
c) N299D, Y426H, and S507E; and/or
d) F555H, N616E, L706N, Y748S; and/or
e) F555H, N616E, I632T, L706N, and Y748S; and/or
f) S2077G, S2315T, and V2333A; and/or
g) N2038D, S2077G, S2315T, and V2333A; and/or
h) S2077G, K2258Q, S2315T, and V2333A; and/or
i) N2038D, S2077G, K2258Q, S2315T, and V2333A; and/or
j) N2038D, S2077G, S2125G, K2258Q, S2315T, and V2333A; and/or
k) L171Q, S507E, Y748S and V2333A; and/or
l) L171Q, N299D, N616E and V2333A; and/or
m) S112T, S507E, Y748S, K1837E and N2038D; and/or
n) S112T, Y426H, N754D, K1837E and N2038D.

6. The recombinant Factor VIII protein of claim 1 comprising at least amino acid substitutions at positions N79, S112, L160, L171, V184, N233, I265, N299, Y426, S507, F555, N616, L706, and Y748.

7. The recombinant Factor VIII protein of claim 1 comprising at least amino acid substitutions at positions N79, S112, L160, L171, V184, N233, I265, N299, Y426, S507, F555, N616, L706, Y748, N2038, S2077, S2315 and V2333.

8. The recombinant Factor VIII protein of claim 1 comprising at least the amino acid substitution at position K1837.

9. The recombinant Factor VIII protein of claim 1 having a reduced immunogenicity compared to a Factor VIII protein consisting of SEQ ID NO: 2.

10. The recombinant Factor VIII protein of claim 1 having at least 90% sequence identity to a Factor VIII protein of SEQ ID NO: 5, wherein only the A1, a1, A2, a2, a3, A3, C1 and C2 domains are considered for determination of sequence identity, or a fusion protein of said recombinant Factor VIII protein.

11. The recombinant Factor VIII protein of claim 1 that is a single chain Factor VIII protein or a heterodimeric Factor VIII protein.

12. The recombinant Factor VIII protein of claim 1 that is a fusion protein, wherein the fusion partner is selected from the group comprising an Fc region, albumin, an albumin binding sequence, PAS polypeptides, HAP polypeptides, the C-terminal peptide of the beta subunit of chorionic gonadotropin, albumin-binding small molecules, polyethylenglycol, hydroxyethyl starch, and combinations thereof.

13. A nucleic acid encoding the recombinant Factor VIII protein of claim 1.

14. A host cell comprising the nucleic acid of claim 13.

15. A pharmaceutical composition comprising the recombinant Factor VIII protein of claim 1.

16. An in vitro method for preparing a Factor VIII protein of claim 1, comprising culturing a host cell of claim 14 expressing said FVIII protein under suitable conditions and isolating said FVIII protein.

17. An in vitro method for analyzing the immunogenicity of a protein, comprising co-cultivating dendritic cells incubated with the protein of claim 1 and regulatory T-cell-depleted $CD4^+$ T cells of a donor and testing activation of said T cells.

18. The recombinant Factor VIII protein of claim 4, wherein the at least three amino acid substitutions are selected from the group consisting of Y748S, L171Q, S507E, N79S, S112T, L160S, V184A, N233D, I265T, N299D, Y426H, F555H, N616E, I632T, L706N, K1837E, R1936Q, N2038D, S2077G, S2125G, F2215H, K2226Q, K2258Q, S2315T and V2333A.

19. The recombinant Factor VIII protein of claim 6, wherein the substitutions are N79S, S112T, L160S, L171Q, V184A, N233D, I265T, N299D, Y426H, S507E, F555H, N616E, L706N, and Y748S.

20. The recombinant Factor VIII protein of claim 19, wherein the protein further includes K1837E and comprises the amino acid sequence according to aa 20-1533 of SEQ ID NO: 7.

21. The recombinant Factor VIII protein of claim 7, comprising amino acid substitutions N79S, S112T, L160S, L171Q, V184A, N233D, I265T, N299D, Y426H, S507E, F555H, N616E, L706N, Y748S, N2038D, S2077G, S2315T and V2333A.

22. The recombinant Factor VIII protein of claim 21, wherein the protein comprises the amino acid sequence according to aa 20-1533 of SEQ ID NO: 6.

23. The recombinant Factor VIII protein of claim 8, wherein said substitution is K1837E.

24. The recombinant Factor VIII protein of claim 9, wherein said immunogenicity is determined by an immunogenicity score or an assay comprising co-cultivating dendritic cells incubated with said protein and regulatory T-cell-depleted $CD4^+$ T cells of a donor and testing activation of said T cells.

25. The recombinant Factor VIII protein of claim 11, that is a single chain B-domain deleted Factor VIII protein.

26. The nucleic acid of claim 13, wherein the nucleic acid is an expression vector suitable for expression of said recombinant Factor VIII protein in a mammalian cell selected from the group comprising a human cell.

27. The host cell of claim 14, wherein the host cell is a mammalian cell comprising an expression vector suitable for expression of said recombinant Factor VIII protein in said cell.

28. The pharmaceutical of claim 15, further comprising an immunosuppressive agent selected from the group comprising methylprednisolone, prednisolone, cyclophosphamide, rituximab, and/or cyclosporin.

29. A method for treating a patient with Hemophilia A comprising administering to the patient the pharmaceutical composition of claim 15, wherein the patient is selected from the group comprising a patient not previously treated with any Factor VIII protein, a patient previously treated with a Factor VIII protein, a patient who has an antibody response including an inhibitory antibody response to a Factor VIII protein, and a patient who has had an antibody response including an inhibitory antibody response to a Factor VIII protein who has been treated by ITI.

* * * * *